United States Patent
DeRosa et al.

(10) Patent No.: US 11,884,692 B2
(45) Date of Patent: Jan. 30, 2024

(54) METHODS FOR PURIFICATION OF MESSENGER RNA

(71) Applicant: Translate Bio, Inc., Waltham, MA (US)

(72) Inventors: Frank DeRosa, Cambridge, MA (US); Anusha Dias, Cambridge, MA (US); Michael Heartlein, Cambridge, MA (US); Shrirang Karve, Cambridge, MA (US)

(73) Assignee: TRANSLATE BIO, INC., Waltham, MA (US)

( * ) Notice: Subject to any disclaimer, the term of this patent is extended or adjusted under 35 U.S.C. 154(b) by 0 days.

(21) Appl. No.: 17/811,022

(22) Filed: Jul. 6, 2022

(65) Prior Publication Data

US 2022/0402958 A1  Dec. 22, 2022

Related U.S. Application Data

(63) Continuation of application No. 17/344,535, filed on Jun. 10, 2021, which is a continuation of application No. 16/196,664, filed on Nov. 20, 2018, now Pat. No. 11,059,841, which is a continuation of application No. 15/831,252, filed on Dec. 4, 2017, now Pat. No. 10,155,785, which is a continuation of application No. 14/696,140, filed on Apr. 24, 2015, now Pat. No. 9,850,269.

(60) Provisional application No. 61/984,503, filed on Apr. 25, 2014.

(51) Int. Cl.
*C07H 1/06* (2006.01)
*C07H 21/00* (2006.01)
*C12N 15/10* (2006.01)
*C07H 21/02* (2006.01)

(52) U.S. Cl.
CPC .............. *C07H 1/06* (2013.01); *C07H 21/00* (2013.01); *C07H 21/02* (2013.01); *C12N 15/1017* (2013.01)

(58) Field of Classification Search
CPC ......... C12N 15/00; C12N 15/17; C07H 21/00
See application file for complete search history.

(56) References Cited

U.S. PATENT DOCUMENTS

| | | |
|---|---|---|
| 2,647,121 A | 7/1953 | Jacoby |
| 2,717,909 A | 9/1955 | Kosmin |
| 2,819,718 A | 1/1958 | Goldman |
| 2,844,629 A | 7/1958 | William et al. |
| 3,096,560 A | 7/1963 | Liebig |
| 3,535,289 A | 10/1970 | Yoshihara et al. |
| 3,614,954 A | 10/1971 | Mirowski et al. |
| 3,614,955 A | 10/1971 | Mirowski |
| 3,656,185 A | 4/1972 | Carpentier |
| 3,805,301 A | 4/1974 | Liebig |
| 3,945,052 A | 3/1976 | Liebig |
| 3,995,623 A | 12/1976 | Blake et al. |
| 4,013,507 A | 3/1977 | Rembaum |
| 4,072,146 A | 2/1978 | Howes |
| 4,096,860 A | 6/1978 | Mclaughlin |
| 4,099,528 A | 7/1978 | Sorenson et al. |
| 4,106,129 A | 8/1978 | Carpentier et al. |
| 4,134,402 A | 1/1979 | Mahurkar |
| 4,140,126 A | 2/1979 | Choudhury |
| 4,180,068 A | 12/1979 | Jacobsen et al. |
| 4,182,833 A | 1/1980 | Hicks |
| 4,227,533 A | 10/1980 | Godfrey |
| 4,284,459 A | 8/1981 | Patel et al. |
| 4,308,085 A | 12/1981 | Horhold et al. |
| 4,323,525 A | 4/1982 | Bornat |
| 4,335,723 A | 6/1982 | Patel |
| 4,339,369 A | 7/1982 | Hicks et al. |
| 4,355,426 A | 10/1982 | MacGregor |
| 4,375,817 A | 3/1983 | Engle et al. |
| 4,385,631 A | 5/1983 | Uthmann |
| 4,401,472 A | 8/1983 | Gerber |
| 4,406,656 A | 9/1983 | Hattler et al. |
| 4,475,972 A | 10/1984 | Wong |
| 4,530,113 A | 7/1985 | Matterson |
| 4,550,447 A | 11/1985 | Seiler, Jr. et al. |
| 4,562,596 A | 1/1986 | Kornberg |

(Continued)

FOREIGN PATENT DOCUMENTS

| CA | 2518132 A1 | 3/2006 |
|---|---|---|
| CA | 2807552 A1 | 2/2012 |

(Continued)

OTHER PUBLICATIONS

Goss et al., J. of Chromatography 588:157 (Year: 1991).*

(Continued)

*Primary Examiner* — Ethan C Whisenant
(74) *Attorney, Agent, or Firm* — LATHROP GPM LLP; James H. Velema, Esq.

(57) ABSTRACT

The present invention provides, among other things, methods of purifying messenger RNA (mRNA) including the steps of (a) precipitating mRNA from an impure preparation; (b) subjecting the impure preparation comprising precipitated mRNA to a purification process involving membrane filtration such that the precipitated mRNA is captured by a membrane; and (c) eluting the captured precipitated mRNA from the membrane by re-solubilizing the mRNA, thereby resulting in a purified mRNA solution. In some embodiments, a purification process involving membrane filtration suitable for the present invention is tangential flow filtration.

16 Claims, 22 Drawing Sheets

Specification includes a Sequence Listing.

(56) References Cited

U.S. PATENT DOCUMENTS

| | | |
|---|---|---|
| 4,568,329 A | 2/1986 | Mahurkar |
| 4,571,241 A | 2/1986 | Christopher |
| 4,601,718 A | 7/1986 | Possis et al. |
| 4,647,416 A | 3/1987 | Seiler, Jr. et al. |
| 4,662,382 A | 5/1987 | Sluetz et al. |
| 4,701,162 A | 10/1987 | Rosenberg |
| 4,710,169 A | 12/1987 | Christopher |
| 4,720,517 A | 1/1988 | Ravichandran et al. |
| 4,737,323 A | 4/1988 | Martin et al. |
| 4,762,915 A | 8/1988 | Kung et al. |
| 4,782,836 A | 11/1988 | Alt |
| 4,843,155 A | 6/1989 | Chomczynski |
| 4,856,521 A | 8/1989 | Irnich |
| 4,860,751 A | 8/1989 | Callaghan |
| 4,878,908 A | 11/1989 | Martin et al. |
| 4,892,540 A | 1/1990 | Vallana |
| 4,897,355 A | 1/1990 | Eppstein et al. |
| 4,920,016 A | 4/1990 | Allen et al. |
| 4,946,683 A | 8/1990 | Forssen |
| 4,946,857 A | 8/1990 | Kanehira et al. |
| 4,960,409 A | 10/1990 | Catalano |
| 4,966,945 A | 10/1990 | Drawert et al. |
| 5,024,671 A | 6/1991 | Tu et al. |
| 5,025,005 A | 6/1991 | Nomura et al. |
| 5,047,540 A | 9/1991 | Kamata et al. |
| 5,101,824 A | 4/1992 | Lekholm |
| 5,104,399 A | 4/1992 | Lazarus |
| 5,116,360 A | 5/1992 | Pinchuk et al. |
| 5,138,067 A | 8/1992 | Kamata et al. |
| 5,151,105 A | 9/1992 | Kwan-Gett |
| 5,171,678 A | 12/1992 | Behr et al. |
| 5,176,661 A | 1/1993 | Evard et al. |
| 5,194,654 A | 3/1993 | Hostetler et al. |
| 5,200,395 A | 4/1993 | Eto et al. |
| 5,223,263 A | 6/1993 | Hostetler et al. |
| 5,256,294 A * | 10/1993 | van Reis ............... C12M 47/02 210/641 |
| 5,261,419 A | 11/1993 | Osypka |
| 5,264,618 A | 11/1993 | Felgner et al. |
| 5,279,833 A | 1/1994 | Rose |
| 5,282,824 A | 2/1994 | Gianturco |
| 5,284,491 A | 2/1994 | Sutton et al. |
| 5,300,022 A | 4/1994 | Klapper et al. |
| 5,314,430 A | 5/1994 | Bardy |
| 5,330,768 A | 7/1994 | Park et al. |
| 5,334,761 A | 8/1994 | Gebeyehu et al. |
| 5,395,619 A | 3/1995 | Zalipsky et al. |
| 5,405,363 A | 4/1995 | Kroll et al. |
| 5,405,379 A | 4/1995 | Lane |
| 5,455,352 A | 10/1995 | Huellmann et al. |
| 5,464,924 A | 11/1995 | Silvis et al. |
| 5,503,852 A | 4/1996 | Steiner et al. |
| 5,528,023 A | 6/1996 | Butturini et al. |
| 5,552,155 A | 9/1996 | Bailey et al. |
| 5,595,756 A | 1/1997 | Bally et al. |
| 5,607,385 A | 3/1997 | Francischelli et al. |
| 5,609,624 A | 3/1997 | Kalis |
| 5,610,283 A | 3/1997 | Buechler |
| 5,614,548 A | 3/1997 | Piantadosi et al. |
| 5,626,869 A | 5/1997 | Nyqvist et al. |
| 5,631,018 A | 5/1997 | Zalipsky et al. |
| 5,677,124 A | 10/1997 | DuBois et al. |
| 5,693,088 A | 12/1997 | Lazarus |
| 5,697,953 A | 12/1997 | Kroll et al. |
| 5,700,437 A | 12/1997 | Fujii et al. |
| 5,705,188 A | 1/1998 | Junichi et al. |
| 5,705,385 A | 1/1998 | Bally et al. |
| 5,736,573 A | 4/1998 | Galat |
| 5,744,335 A | 4/1998 | Wolff et al. |
| 5,772,694 A | 6/1998 | Bokros et al. |
| 5,776,165 A | 7/1998 | Ripart |
| 5,776,747 A | 7/1998 | Schinstine et al. |
| 5,783,383 A | 7/1998 | Kondo et al. |
| 5,844,107 A | 12/1998 | Hanson et al. |
| 5,863,770 A | 1/1999 | Tsui et al. |
| 5,874,105 A | 2/1999 | Watkins et al. |
| 5,885,613 A | 3/1999 | Holland et al. |
| 5,910,168 A | 6/1999 | Myers et al. |
| 5,916,208 A | 6/1999 | Luther et al. |
| 5,965,434 A | 10/1999 | Wolff et al. |
| 5,976,567 A | 11/1999 | Wheeler et al. |
| 5,976,569 A | 11/1999 | Milstein |
| 5,981,501 A | 11/1999 | Wheeler et al. |
| 6,055,454 A | 4/2000 | Heemels |
| 6,067,471 A | 5/2000 | Warren |
| 6,090,384 A | 7/2000 | Ra et al. |
| 6,096,070 A | 8/2000 | Ragheb et al. |
| 6,096,075 A | 8/2000 | Bokros et al. |
| 6,120,799 A | 9/2000 | McDonald et al. |
| 6,147,055 A | 11/2000 | Hobart et al. |
| 6,152,955 A | 11/2000 | KenKnight et al. |
| 6,165,763 A | 12/2000 | Brown et al. |
| 6,169,923 B1 | 1/2001 | Kroll |
| 6,176,877 B1 | 1/2001 | Buchanan et al. |
| 6,180,778 B1 | 1/2001 | Bastian et al. |
| 6,204,297 B1 | 3/2001 | Tracy et al. |
| 6,210,892 B1 | 4/2001 | Bennett et al. |
| 6,214,804 B1 | 4/2001 | Felgner et al. |
| 6,271,208 B1 | 8/2001 | Bischoff |
| 6,271,209 B1 | 8/2001 | Smith et al. |
| 6,287,591 B1 | 9/2001 | Semple et al. |
| 6,299,604 B1 | 10/2001 | Ragheb et al. |
| 6,335,199 B1 | 1/2002 | Bischoff et al. |
| 6,358,278 B1 | 3/2002 | Brendzel et al. |
| 6,370,434 B1 | 4/2002 | Zhang et al. |
| 6,371,983 B1 | 4/2002 | Lane |
| 6,383,393 B1 | 5/2002 | Colpan et al. |
| 6,417,326 B1 | 7/2002 | Cullis et al. |
| 6,485,726 B1 | 11/2002 | Blumberg et al. |
| 6,534,484 B1 | 3/2003 | Wheeler et al. |
| 6,585,410 B1 | 7/2003 | Ryan |
| 6,586,410 B1 | 7/2003 | Wheeler et al. |
| 6,670,178 B1 | 12/2003 | Selden et al. |
| 6,696,424 B1 | 2/2004 | Wheeler |
| 6,733,777 B2 | 5/2004 | Erbacher et al. |
| 6,743,823 B1 | 6/2004 | Summar et al. |
| 6,756,055 B2 | 6/2004 | McDonald et al. |
| 6,790,838 B2 | 9/2004 | Alison et al. |
| 6,815,432 B2 | 11/2004 | Wheeler et al. |
| 6,821,530 B2 | 11/2004 | Koob et al. |
| 6,835,395 B1 | 12/2004 | Semple et al. |
| 6,858,224 B2 | 2/2005 | Wheeler et al. |
| 6,858,225 B2 | 2/2005 | Semple et al. |
| 6,887,665 B2 | 5/2005 | Trulson et al. |
| 6,986,902 B1 | 1/2006 | Chen et al. |
| 6,998,115 B2 | 2/2006 | Langer et al. |
| 7,022,214 B2 | 4/2006 | Olech |
| 7,067,697 B2 | 6/2006 | Gao |
| 7,084,303 B2 | 8/2006 | Watanabe et al. |
| 7,341,738 B2 | 3/2008 | Semple et al. |
| 7,422,902 B1 | 9/2008 | Wheeler et al. |
| 7,427,394 B2 | 9/2008 | Anderson et al. |
| 7,507,859 B2 | 3/2009 | Grinstaff et al. |
| 7,556,684 B2 | 7/2009 | Bury et al. |
| 7,745,651 B2 | 6/2010 | Heyes et al. |
| 7,767,399 B2 | 8/2010 | Murphy |
| 7,799,565 B2 | 9/2010 | MacLachlan et al. |
| 7,803,397 B2 | 9/2010 | Heyes et al. |
| 7,901,708 B2 | 3/2011 | MacLachlan et al. |
| 7,972,435 B2 | 7/2011 | Bury et al. |
| 8,021,686 B2 | 9/2011 | Semple et al. |
| 8,071,082 B2 | 12/2011 | Zugates et al. |
| 8,075,780 B2 | 12/2011 | Pearce |
| 8,101,741 B2 | 1/2012 | MacLachlan et al. |
| 8,106,022 B2 | 1/2012 | Manoharan et al. |
| 8,158,601 B2 | 4/2012 | Chen et al. |
| 8,188,263 B2 | 5/2012 | MacLachlan et al. |
| RE43,612 E | 8/2012 | Anderson et al. |
| 8,236,943 B2 | 8/2012 | Lee et al. |
| 8,278,036 B2 | 10/2012 | Kariko et al. |
| 8,287,849 B2 | 10/2012 | Langer et al. |
| 8,329,070 B2 | 12/2012 | MacLachlan et al. |
| 8,450,298 B2 | 5/2013 | Mahon et al. |
| 8,450,467 B2 | 5/2013 | Manoharan et al. |

(56) References Cited

U.S. PATENT DOCUMENTS

| | | |
|---|---|---|
| 8,470,585 B2 | 6/2013 | De Vocht et al. |
| 8,513,403 B2 | 8/2013 | MacLachlan et al. |
| 8,557,231 B2 | 10/2013 | Langer et al. |
| 8,562,966 B2 | 10/2013 | Zugates et al. |
| 8,569,256 B2 | 10/2013 | Heyes et al. |
| 8,652,512 B2 | 2/2014 | Schmehl et al. |
| 8,691,966 B2 | 4/2014 | Kariko et al. |
| 8,710,200 B2 | 4/2014 | Schrum et al. |
| 8,748,089 B2 | 6/2014 | Kariko et al. |
| 8,802,644 B2 | 8/2014 | Chen et al. |
| 8,808,681 B2 | 8/2014 | Anderson et al. |
| 8,808,982 B2 | 8/2014 | Dahl et al. |
| 8,822,663 B2 | 9/2014 | Schrum et al. |
| 8,828,956 B2 | 9/2014 | Manoharan et al. |
| 8,835,108 B2 | 9/2014 | Kariko et al. |
| 8,846,348 B2 | 9/2014 | Jendrisak et al. |
| 8,853,377 B2 | 10/2014 | Guild et al. |
| 8,859,229 B2 | 10/2014 | Rabinovich et al. |
| 8,883,202 B2 | 11/2014 | Manoharan et al. |
| 8,936,942 B2 | 1/2015 | Heyes et al. |
| 8,969,353 B2 | 3/2015 | Mahon et al. |
| 8,980,864 B2 | 3/2015 | Hoge et al. |
| 8,999,351 B2 | 4/2015 | Manoharan et al. |
| 8,999,950 B2 | 4/2015 | MacLachlan et al. |
| 9,012,219 B2 | 4/2015 | Kariko et al. |
| 9,012,498 B2 | 4/2015 | Manoharan et al. |
| 9,018,187 B2 | 4/2015 | Heyes et al. |
| 9,051,567 B2 | 6/2015 | Fitzgerald et al. |
| 9,061,059 B2 | 6/2015 | Chakraborty et al. |
| 9,074,208 B2 | 7/2015 | MacLachlan et al. |
| 9,089,604 B2 | 7/2015 | Chakraborty et al. |
| 9,095,552 B2 | 8/2015 | Chakraborty et al. |
| 9,107,886 B2 | 8/2015 | Chakraborty et al. |
| 9,114,113 B2 | 8/2015 | Chakraborty et al. |
| 9,181,319 B2 | 11/2015 | Schrum et al. |
| 9,181,321 B2 | 11/2015 | Heartlein et al. |
| 9,186,325 B2 | 11/2015 | Manoharan et al. |
| 9,186,372 B2 | 11/2015 | de Fougerolles et al. |
| 9,187,748 B2 | 11/2015 | Geisbert et al. |
| 9,192,651 B2 | 11/2015 | Chakraborty et al. |
| 9,220,755 B2 | 12/2015 | Chakraborty et al. |
| 9,220,792 B2 | 12/2015 | Chakraborty et al. |
| 9,233,141 B2 | 1/2016 | Chakraborty et al. |
| 9,254,311 B2 | 2/2016 | Bancel et al. |
| 9,295,689 B2 | 3/2016 | de Fougerolles et al. |
| 9,301,993 B2 | 4/2016 | Chakraborty et al. |
| 9,303,079 B2 | 4/2016 | Chakraborty et al. |
| 9,334,328 B2 | 5/2016 | Schrum et al. |
| 9,345,780 B2 | 5/2016 | Manoharan et al. |
| 9,352,042 B2 | 5/2016 | Heyes et al. |
| 9,352,048 B2 | 5/2016 | Manoharan et al. |
| 9,364,435 B2 | 6/2016 | Yaworski et al. |
| 9,394,234 B2 | 7/2016 | Chen et al. |
| 9,404,127 B2 | 8/2016 | Yaworski et al. |
| 9,428,751 B2 | 8/2016 | MacDonald et al. |
| 9,464,124 B2 | 10/2016 | Bancel et al. |
| 9,492,386 B2 | 11/2016 | MacLachlan et al. |
| 9,504,734 B2 | 11/2016 | Bancel et al. |
| 9,518,272 B2 | 12/2016 | Yaworski et al. |
| 9,580,734 B2 | 2/2017 | Shankar et al. |
| 9,713,626 B2 | 7/2017 | Heartlein et al. |
| 9,850,269 B2 * | 12/2017 | DeRosa ............ C07H 21/02 |
| 10,155,785 B2 | 12/2018 | DeRosa et al. |
| 2001/0047091 A1 | 11/2001 | Miki et al. |
| 2002/0022721 A1 | 2/2002 | Trulson et al. |
| 2002/0094528 A1 | 7/2002 | Salafsky |
| 2002/0192651 A1 | 12/2002 | Wheeler et al. |
| 2002/0192721 A1 | 12/2002 | Rizzuto et al. |
| 2002/0193622 A1 | 12/2002 | Watanabe et al. |
| 2003/0044771 A1 | 3/2003 | Anderson et al. |
| 2003/0064951 A1 | 4/2003 | Bussey et al. |
| 2003/0082154 A1 | 5/2003 | Leamon |
| 2003/0083272 A1 | 5/2003 | Wiederholt et al. |
| 2003/0104044 A1 | 6/2003 | Semple et al. |
| 2003/0170637 A1 | 9/2003 | Pirrung et al. |
| 2003/0181410 A1 | 9/2003 | Wheeler et al. |
| 2003/0001890 A1 | 10/2003 | Ginsberg et al. |
| 2003/0186237 A1 | 10/2003 | Ginsberg et al. |
| 2003/0215395 A1 | 11/2003 | Yu et al. |
| 2004/0110709 A1 | 6/2004 | Li et al. |
| 2004/0132683 A1 | 7/2004 | Felgner et al. |
| 2004/0142025 A1 | 7/2004 | MacLachlan et al. |
| 2004/0219534 A1 | 11/2004 | Belly et al. |
| 2004/0224912 A1 | 11/2004 | Dobie et al. |
| 2004/0235982 A1 | 11/2004 | Rabasco et al. |
| 2005/0004058 A1 | 1/2005 | Benoit et al. |
| 2005/0008689 A1 | 1/2005 | Semple et al. |
| 2005/0032730 A1 | 2/2005 | Von Der Mulbe et al. |
| 2005/0054026 A1 | 3/2005 | Atsushi et al. |
| 2005/0059005 A1 | 3/2005 | Tuschl et al. |
| 2005/0059024 A1 | 3/2005 | Conrad |
| 2005/0059624 A1 | 3/2005 | Hoerr et al. |
| 2005/0065107 A1 | 3/2005 | Hobart et al. |
| 2005/0069590 A1 | 3/2005 | Buehler et al. |
| 2005/0079212 A1 | 4/2005 | Wheeler et al. |
| 2005/0089999 A1 | 4/2005 | Zhang et al. |
| 2005/0112755 A1 | 5/2005 | Pearce |
| 2005/0143332 A1 | 6/2005 | Monahan et al. |
| 2005/0148786 A1 | 7/2005 | Ikeda et al. |
| 2005/0158302 A1 | 7/2005 | Faustman et al. |
| 2005/0226847 A1 | 10/2005 | Coffin |
| 2005/0244882 A1 | 11/2005 | Gauch et al. |
| 2005/0244961 A1 | 11/2005 | Short et al. |
| 2005/0250723 A1 | 11/2005 | Hoerr et al. |
| 2006/0008910 A1 | 1/2006 | MacLachlan et al. |
| 2006/0051771 A1 | 3/2006 | Murphy et al. |
| 2006/0059576 A1 | 3/2006 | Pasinetti et al. |
| 2006/0069225 A1 | 3/2006 | Wintermantel et al. |
| 2006/0083780 A1 | 4/2006 | Heyes et al. |
| 2006/0099605 A1 | 5/2006 | Hall, Jr. et al. |
| 2006/0172003 A1 | 8/2006 | Meers et al. |
| 2006/0204566 A1 | 9/2006 | Smyth-Templeton et al. |
| 2006/0216343 A1 | 9/2006 | Panzner et al. |
| 2006/0223939 A1 | 10/2006 | Lange et al. |
| 2006/0228404 A1 | 10/2006 | Anderson et al. |
| 2006/0241071 A1 | 10/2006 | Grinstaff et al. |
| 2006/0246434 A1 | 11/2006 | Erlander et al. |
| 2007/0135372 A1 | 6/2007 | MacLachlan et al. |
| 2007/0142628 A1 | 6/2007 | Ghoshal et al. |
| 2007/0172950 A1 | 7/2007 | Wheeler et al. |
| 2007/0252295 A1 | 11/2007 | Panzner et al. |
| 2007/0275923 A1 | 11/2007 | Chen et al. |
| 2007/0281336 A1 | 12/2007 | Jendrisak et al. |
| 2008/0113357 A1 | 5/2008 | Baggino et al. |
| 2008/0138886 A1 | 6/2008 | Murphy et al. |
| 2008/0145338 A1 | 6/2008 | Anderson et al. |
| 2008/0160048 A1 | 7/2008 | Fuller |
| 2008/0242626 A1 | 10/2008 | Zugates et al. |
| 2008/0248559 A1 | 10/2008 | Inomata et al. |
| 2008/0260706 A1 | 10/2008 | Rabinovich et al. |
| 2009/0023673 A1 | 1/2009 | Manoharan et al. |
| 2009/0093433 A1 | 4/2009 | Woolf et al. |
| 2009/0163705 A1 | 6/2009 | Manoharan et al. |
| 2009/0186805 A1 | 7/2009 | Tabor et al. |
| 2009/0221684 A1 | 9/2009 | Grinstaff et al. |
| 2009/0263407 A1 | 10/2009 | Dande et al. |
| 2009/0270481 A1 | 10/2009 | MacLachlan et al. |
| 2009/0275637 A1 | 11/2009 | Townshend et al. |
| 2009/0286852 A1 | 11/2009 | Kariko et al. |
| 2009/0326051 A1 | 12/2009 | Corey et al. |
| 2010/0028943 A1 | 2/2010 | Thomas et al. |
| 2010/0029501 A1 | 2/2010 | Samal et al. |
| 2010/0035249 A1 | 2/2010 | Hayashizaki et al. |
| 2010/0036084 A1 | 2/2010 | Langer et al. |
| 2010/0041152 A1 | 2/2010 | Wheeler et al. |
| 2010/0047261 A1 | 2/2010 | Hoerr et al. |
| 2010/0092572 A1 | 4/2010 | Kaeuper et al. |
| 2010/0120129 A1 | 5/2010 | Amshey et al. |
| 2010/0178699 A1 | 7/2010 | Gao et al. |
| 2010/0189729 A1 | 7/2010 | Hoerr et al. |
| 2010/0218264 A1 | 8/2010 | Cui et al. |
| 2010/0267806 A1 | 10/2010 | Bumcrot et al. |
| 2010/0331234 A1 | 12/2010 | Mahon et al. |
| 2011/0009641 A1 | 1/2011 | Anderson et al. |

(56) References Cited

U.S. PATENT DOCUMENTS

| | | |
|---|---|---|
| 2011/0038941 A1 | 2/2011 | Lee et al. |
| 2011/0092739 A1 | 4/2011 | Chen et al. |
| 2011/0143397 A1 | 6/2011 | Kariko et al. |
| 2011/0159550 A1 | 6/2011 | Sanders et al. |
| 2011/0200582 A1 | 8/2011 | Baryza et al. |
| 2011/0236391 A1 | 9/2011 | Mahler et al. |
| 2011/0244026 A1 | 10/2011 | Guild et al. |
| 2011/0256175 A1 | 10/2011 | Hope et al. |
| 2011/0287951 A1 | 11/2011 | Emmert-Buck et al. |
| 2011/0293703 A1 | 12/2011 | Mahon et al. |
| 2011/0311583 A1 | 12/2011 | Manoharan et al. |
| 2012/0007803 A1 | 1/2012 | Takatsuka |
| 2012/0009222 A1 | 1/2012 | Nguyen et al. |
| 2012/0065252 A1 | 3/2012 | Schrum et al. |
| 2012/0065358 A1 | 3/2012 | Langer et al. |
| 2012/0114831 A1 | 5/2012 | Semple et al. |
| 2012/0128760 A1 | 5/2012 | Manoharan et al. |
| 2012/0129910 A1 | 5/2012 | Thompson et al. |
| 2012/0142756 A1 | 6/2012 | Guild et al. |
| 2012/0174256 A1 | 7/2012 | Kato et al. |
| 2012/0195936 A1 | 8/2012 | Rudolph et al. |
| 2012/0202871 A1 | 8/2012 | Heyes et al. |
| 2012/0237975 A1 | 9/2012 | Schrum et al. |
| 2012/0251560 A1 | 10/2012 | Dahlman et al. |
| 2012/0251618 A1 | 10/2012 | Schrum et al. |
| 2012/0328668 A1 | 12/2012 | MacLachlan et al. |
| 2013/0004992 A1 | 1/2013 | Lin et al. |
| 2013/0017223 A1 | 1/2013 | Hope et al. |
| 2013/0034563 A1* | 2/2013 | Nishioka ............... A61P 19/02 424/143.1 |
| 2013/0158021 A1 | 6/2013 | Dong et al. |
| 2013/0195967 A1 | 8/2013 | Guild et al. |
| 2013/0224730 A1* | 8/2013 | Johnston ............ G01N 33/6845 435/5 |
| 2013/0224824 A1 | 8/2013 | Shingemori et al. |
| 2013/0237594 A1 | 9/2013 | de Fougerolles et al. |
| 2013/0259923 A1 | 10/2013 | Bancel et al. |
| 2013/0259924 A1 | 10/2013 | Bancel et al. |
| 2013/0266640 A1 | 10/2013 | de Fougerolles et al. |
| 2013/0302401 A1 | 11/2013 | Ma et al. |
| 2013/0337045 A1 | 12/2013 | Bredehorst et al. |
| 2013/0337528 A1 | 12/2013 | Thompson et al. |
| 2013/0337579 A1 | 12/2013 | Lee et al. |
| 2014/0010861 A1 | 1/2014 | Bancel et al. |
| 2014/0044772 A1 | 2/2014 | MacLachlan et al. |
| 2014/0093952 A1 | 4/2014 | Serway |
| 2014/0094399 A1 | 4/2014 | Langer et al. |
| 2014/0105964 A1 | 4/2014 | Bancel et al. |
| 2014/0105965 A1 | 4/2014 | Bancel et al. |
| 2014/0147432 A1 | 5/2014 | Bancel et al. |
| 2014/0147454 A1 | 5/2014 | Chakraborty et al. |
| 2014/0148502 A1 | 5/2014 | Bancel et al. |
| 2014/0155472 A1 | 6/2014 | Bancel et al. |
| 2014/0155473 A1 | 6/2014 | Bancel et al. |
| 2014/0155474 A1 | 6/2014 | Bancel et al. |
| 2014/0155475 A1 | 6/2014 | Bancel et al. |
| 2014/0161830 A1 | 6/2014 | Anderson et al. |
| 2014/0162897 A1 | 6/2014 | Grunenwald et al. |
| 2014/0171485 A1 | 6/2014 | Bancel et al. |
| 2014/0179756 A1 | 6/2014 | MacLachlan et al. |
| 2014/0179771 A1 | 6/2014 | Bancel et al. |
| 2014/0186432 A1 | 7/2014 | Bancel et al. |
| 2014/0193482 A1 | 7/2014 | Bancel et al. |
| 2014/0194494 A1 | 7/2014 | Bancel et al. |
| 2014/0199371 A1 | 7/2014 | Bancel et al. |
| 2014/0200163 A1 | 7/2014 | Mikkelsen et al. |
| 2014/0200261 A1 | 7/2014 | Hoge et al. |
| 2014/0200262 A1 | 7/2014 | Bancel et al. |
| 2014/0200263 A1 | 7/2014 | Bancel et al. |
| 2014/0200264 A1 | 7/2014 | Bancel et al. |
| 2014/0206752 A1 | 7/2014 | Afeyan et al. |
| 2014/0206753 A1 | 7/2014 | Guild et al. |
| 2014/0206755 A1 | 7/2014 | Bancel et al. |
| 2014/0206852 A1 | 7/2014 | Hoge et al. |
| 2014/0221248 A1 | 8/2014 | Jendrisak et al. |
| 2014/0221465 A1 | 8/2014 | Bancel et al. |
| 2014/0227300 A1 | 8/2014 | Chin et al. |
| 2014/0243399 A1 | 8/2014 | Schrum et al. |
| 2014/0249208 A1 | 9/2014 | Bancel et al. |
| 2014/0255467 A1 | 9/2014 | Bancel et al. |
| 2014/0255468 A1 | 9/2014 | Bancel et al. |
| 2014/0275227 A1 | 9/2014 | Hoge et al. |
| 2014/0275229 A1 | 9/2014 | Bancel et al. |
| 2014/0288160 A1 | 9/2014 | Guild et al. |
| 2014/0294937 A1 | 10/2014 | MacLachlan et al. |
| 2014/0294938 A1 | 10/2014 | Guild et al. |
| 2014/0294939 A1 | 10/2014 | Guild et al. |
| 2014/0294940 A1 | 10/2014 | Guild et al. |
| 2014/0329884 A1 | 11/2014 | Dong et al. |
| 2014/0343129 A1 | 11/2014 | de Fougerolles et al. |
| 2014/0363876 A1 | 12/2014 | Jendrisak et al. |
| 2015/0004217 A1 | 1/2015 | Guild et al. |
| 2015/0005372 A1 | 1/2015 | Hoge et al. |
| 2015/0011615 A1 | 1/2015 | Manoharan et al. |
| 2015/0011633 A1 | 1/2015 | Shorr et al. |
| 2015/0017211 A1 | 1/2015 | de Fougerolles et al. |
| 2015/0038556 A1 | 2/2015 | Heartlein et al. |
| 2015/0038558 A1 | 2/2015 | Kariko et al. |
| 2015/0044277 A1 | 2/2015 | Bancel et al. |
| 2015/0050354 A1 | 2/2015 | Bouchon et al. |
| 2015/0051268 A1 | 2/2015 | Bancel et al. |
| 2015/0056253 A1 | 2/2015 | Bancel et al. |
| 2015/0064235 A1 | 3/2015 | Bancel et al. |
| 2015/0064236 A1 | 3/2015 | Bancel et al. |
| 2015/0064242 A1 | 3/2015 | Heyes et al. |
| 2015/0064725 A1 | 3/2015 | Schrum et al. |
| 2015/0086614 A1 | 3/2015 | Bancel et al. |
| 2015/0110857 A1 | 4/2015 | DeRosa et al. |
| 2015/0110858 A1 | 4/2015 | DeRosa et al. |
| 2015/0110859 A1 | 4/2015 | Heartlein et al. |
| 2015/0111248 A1 | 4/2015 | Bancel et al. |
| 2015/0111945 A1 | 4/2015 | Geisbert et al. |
| 2015/0119444 A1 | 4/2015 | Manoharan et al. |
| 2015/0119445 A1 | 4/2015 | Manoharan et al. |
| 2015/0157565 A1 | 6/2015 | Heartlein et al. |
| 2015/0166465 A1 | 6/2015 | Chen et al. |
| 2015/0190515 A1 | 7/2015 | Manoharan et al. |
| 2015/0265708 A1 | 9/2015 | Manoharan et al. |
| 2015/0315541 A1 | 11/2015 | Bancel et al. |
| 2015/0315584 A1 | 11/2015 | MacDonald et al. |
| 2015/0366997 A1 | 12/2015 | Guild et al. |
| 2015/0376220 A1 | 12/2015 | DeRosa et al. |
| 2016/0024139 A1 | 1/2016 | Scorza et al. |
| 2016/0024547 A1* | 1/2016 | Bancel ............... C12Q 1/6865 435/91.3 |
| 2016/0046955 A1* | 2/2016 | Wilkerson ......... C12N 15/8218 800/320.2 |
| 2016/0095924 A1 | 4/2016 | Hope et al. |
| 2016/0114011 A1 | 4/2016 | Bancel et al. |
| 2016/0115477 A1 | 4/2016 | MacLachlan et al. |
| 2016/0115483 A1 | 4/2016 | MacLachlan et al. |
| 2016/0136236 A1 | 5/2016 | Hoge et al. |
| 2016/0151284 A1 | 6/2016 | Heyes et al. |
| 2016/0158385 A1 | 6/2016 | Bancel et al. |
| 2016/0193299 A1 | 7/2016 | de Fougerolles et al. |
| 2016/0194368 A1 | 7/2016 | Hoge et al. |
| 2016/0194625 A1 | 7/2016 | Hoge et al. |
| 2016/0199485 A1 | 7/2016 | Manoharan et al. |
| 2016/0213785 A1 | 7/2016 | Manoharan et al. |
| 2016/0237108 A1 | 8/2016 | Fraley et al. |
| 2016/0237134 A1 | 8/2016 | Hoge et al. |
| 2016/0250354 A1 | 9/2016 | Manoharan et al. |
| 2016/0251681 A1 | 9/2016 | Yaworski et al. |
| 2016/0256567 A1 | 9/2016 | Heyes et al. |
| 2016/0256568 A1 | 9/2016 | Heyes et al. |
| 2016/0256573 A1 | 9/2016 | de Fougerolles et al. |
| 2016/0264971 A1 | 9/2016 | Geisbert et al. |
| 2016/0264975 A1 | 9/2016 | Schrum et al. |
| 2016/0274089 A1 | 9/2016 | Ciufolini et al. |
| 2016/0304552 A1 | 10/2016 | Roy et al. |
| 2016/0317458 A1* | 11/2016 | Brito .................. A61K 9/1272 |
| 2016/0317647 A1 | 11/2016 | Ciaramella et al. |
| 2016/0317676 A1 | 11/2016 | Hope et al. |
| 2016/0331828 A1 | 11/2016 | Ciaramella et al. |

(56) References Cited

U.S. PATENT DOCUMENTS

| | | |
|---|---|---|
| 2016/0348099 A1 | 12/2016 | Roy et al. |
| 2016/0354490 A1 | 12/2016 | Roy et al. |
| 2016/0354491 A1 | 12/2016 | Roy et al. |
| 2016/0354492 A1 | 12/2016 | Roy et al. |
| 2016/0354493 A1 | 12/2016 | Roy et al. |
| 2016/0367687 A1 | 12/2016 | Manoharan et al. |
| 2016/0367702 A1 | 12/2016 | Hoge et al. |
| 2016/0375134 A1 | 12/2016 | Bancel et al. |
| 2016/0375137 A9 | 12/2016 | Manoharan et al. |
| 2017/0002060 A1 | 1/2017 | Bolen et al. |
| 2017/0007702 A1 | 1/2017 | Heyes et al. |
| 2018/0009866 A1 | 1/2018 | Hoge et al. |

FOREIGN PATENT DOCUMENTS

| | | |
|---|---|---|
| CN | 1399561 | 2/2003 |
| CN | 100569877 C | 12/2009 |
| CN | 101863544 A | 10/2010 |
| DE | 24 30 998 A1 | 1/1975 |
| DE | 2520814 A1 | 11/1976 |
| DE | 3728917 A1 | 3/1989 |
| EP | 673637 A1 | 9/1995 |
| EP | 0783297 A1 | 7/1997 |
| EP | 0853123 A1 | 7/1998 |
| EP | 0959092 A1 | 11/1999 |
| EP | 1519714 B1 | 4/2005 |
| EP | 1979364 A2 | 10/2008 |
| EP | 1177281 B1 | 1/2009 |
| EP | 2045251 A1 | 4/2009 |
| EP | 2322613 B1 | 5/2011 |
| EP | 2338478 B1 | 6/2011 |
| EP | 2449106 A1 | 5/2012 |
| EP | 2532649 A1 | 12/2012 |
| EP | 2578685 A2 | 4/2013 |
| EP | 2607482 B1 | 6/2013 |
| EP | 2823809 A1 | 1/2015 |
| EP | 3134506 B1 | 8/2019 |
| FR | 1378382 A | 11/1964 |
| FR | 2235112 A1 | 1/1975 |
| GB | 1072118 A | 6/1967 |
| GB | 1602085 A | 11/1981 |
| JP | H07-053535 | 2/1955 |
| JP | S48-022365 | 3/1973 |
| JP | S49-127908 A | 12/1974 |
| JP | S51-023537 | 2/1976 |
| JP | 51-125144 | 11/1976 |
| JP | S52-010847 | 1/1977 |
| JP | S63125144 A | 5/1988 |
| JP | 63-154788 | 6/1988 |
| JP | H09-505593 A | 6/1997 |
| JP | H10-197978 A | 7/1998 |
| JP | 11-005786 A | 1/1999 |
| JP | 11-080142 | 3/1999 |
| JP | 2001-523215 A | 11/2001 |
| JP | 2002-167368 A | 6/2002 |
| JP | 2003-519199 A | 6/2003 |
| JP | 4-108173 B2 | 6/2008 |
| JP | 2008-247749 A | 10/2008 |
| JP | 2010-053108 A | 3/2011 |
| JP | 50-24216 B2 | 9/2012 |
| KR | 10-0148693 B1 | 8/1998 |
| WO | WO-1993/18229 A1 | 9/1993 |
| WO | WO-1993/18754 A1 | 9/1993 |
| WO | WO-1995/11004 A1 | 4/1995 |
| WO | WO-1995/14651 A1 | 6/1995 |
| WO | WO-1995/27478 A1 | 10/1995 |
| WO | WO-1996/18372 A2 | 6/1996 |
| WO | WO-1996/26179 A1 | 8/1996 |
| WO | WO-1996/37211 A1 | 11/1996 |
| WO | WO-1996/40964 A2 | 12/1996 |
| WO | WO-1997/46223 A1 | 12/1997 |
| WO | WO 1998/03142 A1 | 2/1998 |
| WO | WO 1998/03739 A1 | 2/1998 |
| WO | WO 1998/05673 A1 | 2/1998 |
| WO | WO-1998/10748 A1 | 3/1998 |
| WO | WO-1998/16202 A2 | 4/1998 |
| WO | WO-1998/51278 A2 | 11/1998 |
| WO | WO-1998/059076 A1 | 12/1998 |
| WO | WO 1999/02688 | 1/1999 |
| WO | WO-1999/029840 A1 | 6/1999 |
| WO | WO-2000/03044 A1 | 1/2000 |
| WO | WO-2000/62813 A2 | 10/2000 |
| WO | WO-2000/64484 A2 | 11/2000 |
| WO | WO-2000/69913 A1 | 11/2000 |
| WO | WO-2001/05375 A1 | 1/2001 |
| WO | WO-2001/07599 A1 | 2/2001 |
| WO | WO-2002/22709 A1 | 3/2002 |
| WO | WO-2002/31025 A2 | 4/2002 |
| WO | WO-2002/34236 A2 | 5/2002 |
| WO | WO-2002/42317 A2 | 5/2002 |
| WO | WO 2003/033739 A1 | 4/2003 |
| WO | WO-2003/040288 A2 | 5/2003 |
| WO | WO-2003/070735 A2 | 8/2003 |
| WO | WO-2003/082892 A1 | 10/2003 |
| WO | WO-2004/043588 A2 | 5/2004 |
| WO | WO-2004/048345 A2 | 6/2004 |
| WO | WO-2004/106411 A2 | 12/2004 |
| WO | WO-2005/012523 A1 | 2/2005 |
| WO | WO-2005/026372 A1 | 3/2005 |
| WO | WO-2005/028619 A2 | 3/2005 |
| WO | WO-2005/037226 A2 | 4/2005 |
| WO | WO-2005/058933 A1 | 6/2005 |
| WO | WO 2005/075642 A1 | 8/2005 |
| WO | WO-2005/121348 A1 | 12/2005 |
| WO | WO-2006/000448 A1 | 1/2006 |
| WO | WO-2006/016097 A2 | 2/2006 |
| WO | WO-2006/082088 A1 | 8/2006 |
| WO | WO-2006/083721 A2 | 8/2006 |
| WO | WO-2006/105043 A2 | 10/2006 |
| WO | WO-2006/138380 A2 | 12/2006 |
| WO | WO-2007/024708 A2 | 3/2007 |
| WO | WO-2007/031091 A2 | 3/2007 |
| WO | WO-2007/120863 A2 | 10/2007 |
| WO | WO-2007/126386 A1 | 11/2007 |
| WO | WO-2007/143659 A2 | 12/2007 |
| WO | WO-2008/011561 A2 | 1/2008 |
| WO | WO-2008/042973 A2 | 4/2008 |
| WO | WO-2008/083949 A2 | 7/2008 |
| WO | WO-2008/113364 A1 | 9/2008 |
| WO | WO-2009/046220 A2 | 4/2009 |
| WO | WO-2009/093142 A1 | 7/2009 |
| WO | WO-2009/127060 A1 | 10/2009 |
| WO | WO-2009/127230 A1 | 10/2009 |
| WO | WO-2010/042877 A1 | 4/2010 |
| WO | WO-2010/045512 A2 | 4/2010 |
| WO | WO-2010/053572 A2 | 5/2010 |
| WO | WO-2010/054401 A1 | 5/2010 |
| WO | WO-2010/054405 A1 | 5/2010 |
| WO | WO-2010/056403 A1 | 5/2010 |
| WO | WO-2010/099387 A1 | 9/2010 |
| WO | WO-2010/114789 A1 | 10/2010 |
| WO | WO-2010/119256 A1 | 10/2010 |
| WO | WO-2010/129709 A1 | 11/2010 |
| WO | WO-2010/144740 A1 | 12/2010 |
| WO | WO-2010/147992 A1 | 12/2010 |
| WO | WO-2010/148013 A2 | 12/2010 |
| WO | WO-2011/012746 A2 | 2/2011 |
| WO | WO-2011/039144 A1 | 4/2011 |
| WO | WO-2011/068810 A1 | 6/2011 |
| WO | WO-2011/075656 A1 | 6/2011 |
| WO | WO-2011/141705 A1 | 11/2011 |
| WO | WO-2012/019168 A2 | 2/2012 |
| WO | WO-2012/019630 A1 | 2/2012 |
| WO | WO-2012/019780 A1 | 2/2012 |
| WO | WO-2012/027675 A2 | 3/2012 |
| WO | WO-2012/045075 A1 | 4/2012 |
| WO | WO-2012/045082 A2 | 4/2012 |
| WO | WO-2012/075040 A2 | 6/2012 |
| WO | WO-2012/077080 A1 | 6/2012 |
| WO | WO-2012/133737 A1 | 10/2012 |
| WO | WO-2012/135025 A2 | 10/2012 |
| WO | WO-2012/135805 A2 | 10/2012 |
| WO | WO-2012/170889 A1 | 12/2012 |
| WO | WO-2012/170930 A1 | 12/2012 |

(56) References Cited

FOREIGN PATENT DOCUMENTS

| | | |
|---|---|---|
| WO | WO-2013/039857 A1 | 3/2013 |
| WO | WO-2013/039861 A2 | 3/2013 |
| WO | WO-2013/063468 A1 | 5/2013 |
| WO | WO-2013/090186 | 6/2013 |
| WO | WO-2013/101690 A1 | 7/2013 |
| WO | WO-2013/102203 A1 | 7/2013 |
| WO | WO-2013/126803 A1 | 8/2013 |
| WO | WO-2013/130161 | 9/2013 |
| WO | WO-2013/149140 A1 | 10/2013 |
| WO | WO-2013/149141 A1 | 10/2013 |
| WO | WO-2013/151663 A1 | 10/2013 |
| WO | WO-2013/151664 A1 | 10/2013 |
| WO | WO-2013/151666 A2 | 10/2013 |
| WO | WO-2013/151667 A1 | 10/2013 |
| WO | WO-2013/151668 A2 | 10/2013 |
| WO | WO-2013/151670 A2 | 10/2013 |
| WO | WO-2013/151671 A1 | 10/2013 |
| WO | WO-2013/151672 A2 | 10/2013 |
| WO | WO-2013/151736 A2 | 10/2013 |
| WO | WO-2013/182683 | 12/2013 |
| WO | WO-2013/185067 A1 | 12/2013 |
| WO | WO-2013/185069 A1 | 12/2013 |
| WO | WO-2014/028487 A1 | 2/2014 |
| WO | WO-2014/036391 A1 | 3/2014 |
| WO | WO-2014/089486 A1 | 6/2014 |
| WO | WO-2014/113089 A2 | 7/2014 |
| WO | WO-2014/140211 A1 | 9/2014 |
| WO | WO-2014/144039 A1 | 9/2014 |
| WO | WO-2014/144196 A1 | 9/2014 |
| WO | WO-2014/144711 A1 | 9/2014 |
| WO | WO-2014/144767 A1 | 9/2014 |
| WO | WO-2014/152027 A1 | 9/2014 |
| WO | WO-2014/152030 A1 | 9/2014 |
| WO | WO-2014/152031 A1 | 9/2014 |
| WO | WO-2014/152211 A1 | 9/2014 |
| WO | WO-2014/152513 A1 | 9/2014 |
| WO | WO-2014/152540 A1 | 9/2014 |
| WO | WO-2014/152659 A1 | 9/2014 |
| WO | WO-2014/152673 A1 | 9/2014 |
| WO | WO-2014/152774 A1 | 9/2014 |
| WO | WO-2014/152940 A1 | 9/2014 |
| WO | WO-2014/152966 A1 | 9/2014 |
| WO | WO-2014/153052 A2 | 9/2014 |
| WO | WO-2014/158795 A1 | 9/2014 |
| WO | WO-2014/159813 A1 | 9/2014 |
| WO | WO-2014/179562 A1 | 11/2014 |
| WO | WO-2014/210356 A1 | 12/2014 |
| WO | WO-2015/006747 A2 | 1/2015 |
| WO | WO-2015/011633 A1 | 1/2015 |
| WO | WO-2015/048744 A2 | 4/2015 |
| WO | WO-2015/051169 A2 | 4/2015 |
| WO | WO-2015/051173 A2 | 4/2015 |
| WO | WO-2015/058069 A1 | 4/2015 |
| WO | WO-2015/085318 | 6/2015 |
| WO | WO-2015/089511 | 6/2015 |
| WO | WO-2015/164773 A1 | 10/2015 |
| WO | WO-2016/054421 | 4/2016 |
| WO | WO-2016/071857 | 5/2016 |
| WO | WO-2016/077123 | 5/2016 |
| WO | WO-2016/077125 | 5/2016 |
| WO | WO-2016/118724 | 7/2016 |
| WO | WO-2016/118725 | 7/2016 |
| WO | WO-2016/193206 | 8/2016 |
| WO | WO-2016/154127 | 9/2016 |
| WO | WO-2016/164762 | 10/2016 |
| WO | WO-2016/183366 A2 | 11/2016 |
| WO | WO-2016/197132 A1 | 12/2016 |
| WO | WO-2016/197133 A1 | 12/2016 |
| WO | WO-2016/201377 A1 | 12/2016 |
| WO | WO 2017/149139 | 9/2017 |

OTHER PUBLICATIONS

Krieg and Melton Nucleic Acids Research 12(18) : 7057 (Year: 1984).*
Lockard et al. Cell 9:747(1976—part 2) (Year: 1976).*
Ganesh et al., "Detecting Virus-Like Particles from the Umgeni River, South Africa," Clean-Soil, Air, Water 2014, 42 (4), 393-407.
International Search Report and Written Opinion for PCT/US2015/027563, 13 pages (dated Sep. 18, 2015).
U.S. Appl. No. 60/083,294, filed Apr. 28, 1998, Chen et al.
U.S. Appl. No. 61/494,714, filed Jun. 8, 2011, Guild et al.
U.S. Appl. No. 61/494,745, filed Jun. 8, 2011, Guild et al.
U.S. Appl. No. 61/494,881, filed Jun. 8, 2011, Guild et al.
U.S. Appl. No. 61/494,882, filed Jun. 8, 2011, Zhang et al.
Adami, R.C. et al., An amino acid-based amphoteric liposomal delivery system for systemic administration of siRNA. Molecular Therapy 19(6):1141-1151 (2011).
Akinc, A. et al., A combinatorial library of lipid-like materials for delivery of RNAi therapeutics. Nature Biotechnology 26(5):561-569 (2008).
Akinc, A. et al., Development of lipidoid-siRNA formulations for systemic delivery to the liver. Molecular Therapy 17(5):872-879 (2009).
Alton, E.W.F.W. et al., Cationic Lipid-Mediated CFTR Gene Transfer to the Lungs and Nose of Patients with Cystic Fibrosis: a Double-Blind Placebo-Controlled Trial, Lancet, 353:947-954 (1999).
Anderson, D.G. et al., Structure/property studies of polymeric gene delivery using a library of poly(beta-amino esters). Molecular Therapy 11(3):426-434 (2005).
Anderson, D.M. et al., Stability of mRNA/Cationic Lipid Lipoplexes in Human and Rat Cerebrospinal Fluid: Methods and Evidence for Nonviral mRNA Gene Delivery to the Central Nervous System, Human Gene Therapy, 14:191-202 (2003).
Anderson, J. Biological Responses to Materials. Annual Review of Materials Research 31:81-110 (2001).
Anderson, W. French, Human gene therapy, Nature, 392, 25-30 (1998).
Andries, O. et al., Comparison of the Gene Transfer Efficiency of mRNA/GL67 and pDNA/GL67 Complexes in Respiratory Cells, Mol. Pharmaceut., 9: 2136-2145 (2012).
Anonymous, Ambion homepage archived on Jun. 4, 2004.
Anonymous, "DEPC," https://openwetware,org/wiki/DEPC (2007).
Anonymous, mirVana miRNA Isolation, Cat# 1560, Manual Version 0407 ( Jul. 2004).
Anonymous, Qiagen RNeasy Mini 1 Handbook. Fifth Edition, https://www.qiagen.com/ 1-80 Oct. 2013.
Anonymous, Qiagen Buffer RLT Material Safety Data Sheet acc. to ISO/DIS 11014,2013.
Anonymous, "RNeasy® Micro Handbook" (2003).
Anonymous, "RNeasy® Lipid Tissue Mini Handbook" (2003).
Anonymous, "RiboPure™—WBC" (2003).
Auffray, C. et al., Purification of Mouse Immunoglubulin Heavy-Chain Messenger RNAs from Total Myeloma Tumor RNA, European Journal of Biochemistry, 107(2):303-314 (1980).
Author Unknown, Blood Proteins, published by Wikipedia, San Francisco, CA, 2 pages, <http://en.wikipedia.org/wiki/Biood_proteins> downloaded May 17, 2015.
Baboo et al., "'Dark matter' worlds of unstable RNA and protein", Nucleus, 5:4 281-286 (2014).
Bahlke, M. A. et al., Progress towards in vivo use of siRNAs, Molecular Therapy, 13:644-670 (2006).
Bajaj, A. et al., Synthesis and gene transfection efficacies of PEI-cholesterol-based lipopolymers. Bioconjugate Chemistry 19(8):1640-516511 (2008).
Barreau, C. et al., Liposome-mediated RNA transfection should be used with caution, RNA, 12:1790-1793 (2006).
Behr, J. et al., Efficient Gene Transfer into Mammalian Primary Endocrine Cells with Lipo Polyamine-Coated DNA, Proc. Nat.'l Acad. Sci., 86: 6982-6986 (1989).
Bennett, J. Immune response following intraocular delivery of recombinant viral vectors, Gene Therapy, 10: 977-982 (2003).
Bhaduri, S. et al., Procedure for the Preparation of Milligram Quantities of Adenovirus Messenger Ribonucleic Acid, Journal of Virology, vol. 10, p. 1126-1129. (1972).

(56) References Cited

OTHER PUBLICATIONS

Bloomfield, V.A., Quasi-Elastic Light Scattering Applications in Biochemistry and Biology, Ann. Rev. Biophys. Bioeng. 10:421-450 (1981).
Boussif, O. et al., A versatile vector for gene and oligonucleotide transfer into cells in culture and in vivo: polyethylenimine. Proceedings of the National Academy of Sciences of the USA. 92(16):7297-7301 (1995).
Braun, C.S. et al., Structure/function relationships of polyamidoamine/DNA dendrimers as gene delivery vehicles. Journal of Pharmaceutical Sciences 94(2):423-436 (2005).
Breunig, M. et al., Breaking up the correlation between efficacy and toxicity for nonviral gene delivery. Proceedings of the National Academy of Sciences of the U S A. 104(36):14454-14459 (2007).
Breunig, M. et al., Mechanistic investigation of poly(ethylene imine)-based siRNA delivery: disulfide bonds boost intracellular release of the cargo. Journal of Controlled Release 130(1):57-63 (2008).
Brey, D.M. et al., Controlling poly(beta-amino ester) network properties through macromer branching. Acta Biomaterialia 4(2):207-217 (2008).
Brey, D.M. et al., Influence of macromer molecular weight and chemistry on poly(beta-amino ester) network properties and initial cell interactions. Journal of Biomedical Materials Research Part A 85(3):731-741 (2007).
Budker, V. et al., Protein/Amphipathic Polyamine Complexes Enable Highly Efficient Transfection with Minimal Toxicity, BioTechniques, 23: 139-147 (1997).
Burnett, J.C. et al., Current progress of siRNA/shRNA therapeutics in clinical trials. Biotechnology Journal 6(9):1130-1146 (2011).
Byk, G. et al., Synthesis, activity, and structure-activity relationship studies of novel cationic lipids for DNA transfer. Journal of Medical Chemistry 41(2):224-235 (1998).
Caplen, N.J. et al., In vitro liposome-mediated DNA transfection of epithelial cell lines using the cationic liposome DC-Chol/DOPE, Gene Therapy, 2:603-613 (1995).
Cassiman, D. Gene transfer for inborn errors of metabolism of the liver: the clinical perspective, Current Pharmaceutical Design, 17(24):2550-2557 (2011).
Castanotto, D. et al., The promises and pitfalls of RNA-interference-based therapeutics. Nature 457(7228):426-433 (2009).
Chakraborty, C. Potentiality of Small Interfering RNAs (siRNA) as Recent Therapeutic Targets for Gene-Silencing. Current Drug Targets 8(3):469-82 (2007).
Chandler, R. et al., Liver-directed adeno-associated virus serotype 8 gene transfer rescues a lethal murine model of citrullinemmia type 1, Gene Therapy, 20:1188-1191 (2013).
Chau, Y. et al., Investigation of targeting mechanism of new dextran-peptide-methotrexate conjugates using biodistribution study in matrix-metalloproteinase-overexpressing tumor xenograft model, J. Pharm. Sci., 95(3): 542-551 (2006).
Chen, D. et al., Rapid discovery of potent siRNA-containing lipid nanoparticles enabled by controlled microfluidic formulation. Journal of the American Chemical Society 134(16):6948-6951 (2012).
Chen, Y. and Huang, L., Tumor-targeted delivery of siRNA by non-viral vector: safe and effective cancer therapy. Expert Opinion on Drug Delivery 5(12):1301-1311 (2008).
Chiou, H.C. et al., Enhanced resistance to nuclease degradation of nucleic acids complexed to; asialoglycoprotein-polylysine carriers, Nucleic Acids Research, 22(24):5439-5446 (1994).
Christensen, U.B. et al., Intercalating nucleic acids containing insertions of 1-O-(1-pyrenylmethyl)glycerol: stabilisation of dsDNA and discrimination of DNA over RNA, Nucl. Acids. Res., 30(22): 4918-4925 (2002).
Chomczynski et al. "Single-Step Method of RNA Isolation by Acid Guanidinium Thiocyanate-Phenol-Chloroform Extraction", Analytical Biochemistry, 162: 156-9 (1987).
Communication of a notice of opposition for European Patent Application No. 15783316.1, dated May 13, 2020.
Conese, Ml et al., Gene and Cell Therapy for Cystic Fibrosis: From Bench to Bedside, J. Cyst. Fibros., 10 Suppl 2:S114-s128 (2011).
Cowan et al., "Urea and KCl have differential effects on enzyme activities in liver and muscle of estivating versus nonestivating species", Bichem. Cell Biol., 80: 745-55 (2002).
Cotten, M. et al., Receptor-mediated transport of DNA into eukaryotic cells. Methods in Enzymology 217 (H):618-644 (1993).
Cowling, V.H., Regulation of mRNA cap methylation, Biochemical Journal, 425:295-302 (2010).
Creusat, G. et al., Proton sponge trick for pH-sensitive disassembly of polyethylenimine-based siRNA delivery systems. Bioconjugate Chemistry 21(5):994-1002 (2010).
Crooke, S.T. Molecular mechanisms of action of antisense drugs. Biochimica et Biophysica Acta 1489(1):31-44. Review (1999).
Crystal, R.G. Transfer of genes to humans: early lessons and obstacles to success. Science 270(5235):404-410. Review (1995).
Damen, M. et al., Delivery of DNA and siRNA by novel gemini-like amphiphilic peptides. Journal of Controlled Release 145(1):33-39 (2010).
Dande, P. et al., Improving RNA interference in mammalian cells by 4'-thio-modified small interfering RNA (siRNA): effect on siRNA activity and nuclease stability when used in combination with 2'-0-alkyl modifications, Journal of Medicinal Chemistry, 49(5):1624-1634 (2006).
Davis, M. E., The first targeted delivery of siRNA in humans via a self-assembling, cyclodextrin polymer-based nanoparticle: from concept to clinic. Molecular Pharmacuetics 6(3):659-668 (2009).
Davis, M.E. et al., Evidence of RNAi in humans from systemically administered siRNA via targeted nanoparticles. Nature 464(7291):1067-1070 (2010).
Debus, H. et al., Delivery of Messenger RNA Using Poly(ethylene imine)-poly(ethylene glycol)-Copolymer Blends for Polyplex Formation: Biophysical Characterization and In Vitro Transfection Properties, J. Control. Rel., 148:334-343 (2010).
Decher, G. Fuzzy Nanoassemblies: Toward Layered Polymeric Multicomposites. Science 277: 1232-1237 (1997).
Demeshkina, N. et al., Interactions of the ribosome with mRNA and tRNA, Current Opinion in Structural Biology, 20(3):325-332 (2010).
Denardo, S.J. et al., Enhanced Therapeutic Index of Radioimmunotherapy (RIT) in Prostate Cancer Patients Comparison of Radiation Dosimetry for 1,4,7,10-Tetraazacyclododecane-N,N',N'',N'''-Tetraacetic Acid (DOTA)-Peptide versus 2IT-DOTA Monoclonal Antibody Linkage for RIT1, Clin. Cancer Res., 9: 3665s (2003).
Dern, R.J. et al., Toxicity studies of pyrimethamine (daraprim). The American Journal of Tropical Medicine and Hygiene 4(2):217-220 (1955).
Deshmukh, H. M and Huang, L., Liposome and polylysine mediated gene therapy. New Journal of Chemistry 21:113-124 (1997).
Discher, B.M. et al., Polymersomes: tough vesicles made from diblock copolymers. Science 284(5417):1143-1146 (1999).
Discher, D.E. and Eisenberg, A., Polymer vesicles. Science 297(5583):967-973. Review (2002).
Dong, Y. et al., Lipopeptide nanoparticles for potent and selective siRNA delivery in rodents and nonhuman primates, Proceedings of the National Academy of Sciences, 111(11): 3955-3960 (2014).
Drummond, D.C. et al., Optimizing Liposomes for Delivery of Chemotherapeutic Agents to Solid Tumors, Pharmacological Reviews, 51(4): 691-743 (1999).
Dwarki, V. et al., Cationic liposome-mediated RNA transfection, Methods in Enzymology, 217:644-654 (1993).
Elbashir, S.M. et al., RNA interference is mediated by 21- and 22-nucleotide RNAs. Genes & Development 15: 188-200 (2001).
Elton, C., The Next Next Big Thing, Boston Magazine, 106-118 (Mar. 2013).
Emlen, W. et al., Effect of DNA size and strandedness on the in vivo clearance and organ localization of DNA, Clinical & Experimental Immunology, 56:185-192 (1984).
Eon-Duval, A. et al., Removal of RNA impurities by tangential flow filtration in an RNase-free plasmid DNA purification process, Analytical Biochemistry, 316(1):66-73 (2003).
Ernst, N. et al., Interaction of Liposomal and Polycationic Transfection Complexes with Pulmonary Surfactant, J. Gene. Med., 1:331-340 (1999).

(56) References Cited

OTHER PUBLICATIONS

Estimated Number of Animal and Plant Species on Earth, http://www.factmonster.com/ipka/A0934288.html, 2000-2014, 3 pages, (Retrieved Aug. 2, 2014).
Ewert, K. et al., Cationic lipid-DNA complexes for gene therapy: understanding the relationship between complex structure and gene delivery pathways at the molecular level. Current Medicinal Chemistry 11(2): 133-149 (2004).
Fath, S. et al., Multiparameter RNA and Codon Optimization: A Standardized Tool to Assess and Enhance Autologous Mammalian Gene Expression, PLoS One, 6(3):e17596 (2011).
Fechter, P. and Brownlee, G. G., Recognition of mRNA cap structures by viral and cellular proteins, Journal of General Virology, 86:1239-1249 (2005).
Felgner, P.L. and Ringold, G.M., Cationic liposome-mediated transfection, Nature, 337(6205):387-388 (1989).
Felgner, P.L. et al., Lipofection: A Highly Efficient, Lipid-Mediated DNA-Transfection Procedure, Proc. Natl. Acad., 84:7413-7417 (1987).
Fenske, D.B. and Cullis, P., Liposomal nanomedicines. Expert Opinion on Drug Delivery 5(1):25-44 (2008).
Fernandez, V. et al., Cross Flow Filtration of RNA Extracts by Hollow Fiber Membrane, Acta Biotechnologica, 12(1):49-56 (1992).
Ferruti, P.F. and Barbucci, R. , Linear amino polymers: Synthesis, protonation and complex formation. Advances in Polymer Science 58:55-92 (1984).
Ferruti, P.F. et al., A novel modification of poly(l-lysine) leading to a soluble cationic polymer with reduced toxicity and with potential as a transfection agent. Macromolecular Chemistry and Physics 199:2565-2575 (1998).
Fire, A. et al., Potent and specific genetic interference by double-stranded RNA in Caenorhabditis elegans. Nature 391(6669):806-811 (1998).
Fischer, D. et al., Effect of poly(ethylene imine) molecular weight and pegylation on organ distribution and pharmacokinetics; of polyplexes with oligodeoxynucleotides in mice, Drug Metabolism and Disposition, 32(9):983-992 (2004).
Fumoto, S. et al., Targeted Gene Delivery: Importance of Administration Routes, Novel Gene Therapy Approaches, 3-31 (2013).
Furgeson, D.Y. et al., Modified linear polyethylenimine-cholesterol conjugates for DNA complexation. Bioconjugate Chemistry 14(4):840-847 (2003).
Furgeson, D.Y. et al., Novel water insoluble lipoparticulates for gene delivery. Pharmaceutical Research 19(4): 382-390 (2002).
Furuichi et al., Advances in Virus Research 55 : 135 (Year: 2000).
Furuichi, et al., "Viral And Cellular mRNA Capping: Past and Prospects", Advances in Virus Research, vol. 55, 175-184 (2000).
Galipon, J. et al., Stress-induced lncRNAs evade nuclear degradation and enter the translational machinery, Genes to Cells, 18(5):353-368 (2013).
Gao, X. and Huang, L., A novel cationic liposome reagent for efficient transfection of mammalian cells, Biochem. Biophys. Res. Comm., 179(1): 280-285 (1991).
Garbuzenko, O.B. et al., Intratracheal Versus Intravenous Liposomal Delivery of siRNA, Antisense Oligonucleotides and Anticancer Drug, Pharmaceutical Research, 26(2):382-394 (2009).
Genbank, Print-Outs for mRNA sequences of *Arabidopsis thaliana* ACT1, TUB2, PTB1, and PR 1, and Photinus pyralis PpyLuc1 genes.
Geraerts, M. et al., Upscaling of lentiviral vector production by tangential flow filtration, Journal of Gene Medicine, 7(10):1299-1310 (2005).
Godbey, W.T. et al., Size matters: molecular weight affects the efficiency of poly(ethylenimine) as a gene delivery vehicle. Journal of Biomedical Materials Research 45(3):268-275 (1998).
Gonzalez, H. et al., New class of polymers for the delivery of macromolecular therapeutics. Bioconjugate Chemistry 10(6):1068-1074 (1999).
Gonzalez-Aseguinolaza, G. et al., Gene therapy of liver diseases: A 2011 perspective, Clinics and Research in Hepatology and Gastroenterology, 35(11):699-708 (2011).
Gordon, N. Ornithine transcarbamylase deficiency: a urea cycle defect, European Journal of Paediatric Neurology, 7:115-121 (2003).
Grayson, A.C.R. et al., Biophysical and structural characterization of polyethylenimine-mediated siRNA delivery in vitro. Pharmaceutical Research 23(8): 1868-1876 (2006).
Grudzien, E. et al., Novel cap analogs for in vitro synthesis of mRNAs with high translational efficiency, RNA Biology, 10(9):1479-1487 (2004).
Grudzien-Nogalska et al., "Phosphorothioate cap analogs stabilize mRNA and increase translational efficiency in mammalian cells," RNA. 13:1745-1755 (2007).
Grunlan, M.A. et al., Synthesis of 1,9-bis[glycidyloxypropyl]penta(1'H, 1'H, 2'H, 2'H-perfluoroalkylmethylsiloxane)s and copolymerization with piperazine. Polymer 45:2517-2523 (2004).
Gupta, U. et al., A review of in vitro-in vivo investigations on dendrimers: the novel nanoscopic drug carriers. Nanomedicine: Nanotechnology, Biology, and Medicine 2(2):66-73 (2006).
Guttman, M. et al., Chromatin signature reveals over a thousand highly conserved large non-coding RNAs in mammals, Nature, 458:223-227 (2009).
Haensler, J. and Szoka, F., Polyamidoamine cascade polymers mediate efficient transfection of cells in culture. Bioconjugate Chemistry 4(5):372-379 (1993).
Harada-Shiba, M et al., Polyion complex micelles as vectors in gene therapy—pharmacokinetics and in vivo; gene transfer, Gene Therapy, 9(6):407-414 (2002).
Haskins M., Gene Therapy for Lysosomal Storage Disorders (LDSs) in Large Animal Models, ILAR J., 50(2):112-121 (2009).
Hata, A. et al., Isolation and Characterization of the Human Ornithine Transcarbamylase Gene: Structure of the 5'-End Region, Journal of Biochemistry, 100:717-725 (1986).
Hecker, J. et al., Advances in Self-Limited Gene Expression of Protective Intracellular Proteins In-Vivo in Rat Brain Using mRNA / Cationic Lipid Complexes, Anesthesia and Analgesia, 86(2S):346S (1994).
Heidenreich, O. et al., High Activity and Stability of Hammerhead Ribozymes Containing 2'- Modified Pyrimidine Nucleosides and Phosphorothioates, The Journal of Biological Chemistry, 269(3):2131-2138 (1994).
Henkin, R. I. et al., Inhaled Insulin—Intrapulmonary, intranasal, and other routes of administration: Mechanisms of action, Nutrition, 26: 33-39 (2010).
Hess, P. R. et al., Vaccination with mRNAs Encoding Tumor-Associated Antigens and Granulocyte-Macrophage Colony-Stimulating Factor Efficiently Primes CTL Responses, but is Insufficient to Overcome Tolerance to a Model Tumor/Self Antigen, Cancer Immunology, Immunotherapy:CII, 55(6): 672-683 (2006).
Heyes, J. et al., Cationic Lipid Saturation Influences Intracellular Delivery of Encapsulated Nucleic Acids, J. Controlled Release, 107:276-287 (2005).
Higman, M.A. et al., The mRNA (Guanine-7-)methyltransferase Domain of the Vaccinia Virus mRNA Capping Enzyme, The Journal of Biological Chemistry, 269(21):14974-14981 (1994).
Hill, I.R.C. et al., In vitro cytotoxicity of poly(amidoamine)s: relevance to DNA delivery. Biochimica et Biophysica Acta 1427: 161-174 (1999).
Hill, J.G et al., Enantioselective Epoxidation of Allylic Alcohols: (2S,3S)-3-Propyloxiranemethanol. Organic Syntheses Collection 7: 461 (1990) and 63: 66 (1985).
Hillery, A.M. et al., Drug Delivery and Targeting for Pharmacists and Pharmaceutical Scientists, Taylor and Francis (2005).
Hoerr, I. et al., In Vivo Application of RNA Leads to Induction of Specific Cytotoxic T Lymphocytes and Antibodies, European Journal of Immunology, 30(1):1-7 (2000).
Hoerr, "Stabilized Messenger RNA (RNActiveTM) as a Tool for Innovative Gene Delivery," Tissue Engineering. 13:886-887, (2007).
Hofland, H.E.J et al., Formation of stable cationic lipid/DNA complexes for gene transfer. Proceedings of the National Academy of Sciences of the USA 93 (14): 7305-7309 (1996).

(56) References Cited

OTHER PUBLICATIONS

*Homo sapiens* galactosidase, alpha (GLA) mRNA, NCBI Reference Sequence NM_000169.1, Modification Date: Nov. 17, 2006.
Hook and Schagat, Purify RNA transcribed in vitro using the Pure Yield™ RNA Midiprep System—Promega Corporation (2011).
Hope, M.J. et al., Cationic Lipids, Phosphatidylethanolamine and the Intracellular Delivery of Polymeric, Nucleic Acid-Based Drugs. Molecular Membrane Technology 15:1-14 (1998).
Hope, M.J. et al., Reduction of Liposome Size and Preparation of Unilamellar Vesicles by Extrusion Techniques, In: Liposome Technology, 1:123-139 (1993).
Hornung, V. et al., Quantitative expression of toll-like receptor 1-10 mRNA in cellular subsets of human peripheral blood mononuclear cells and sensitivity to CpG oligodeoxynucleotides. The Journal of Immunology 168: 4531-4537 (2002).
Horwich, A.L. et al., Structure and Expression of a Complementary DNA for the Nuclear Coded Precursor of Human Mitochondrial Ornithine Transcarbamylase, Science, 224(4653):1068-1074 (1984).
Horwich, A.L. et al., Targeting of Pre-Ornithine Transcarbamylase to Mitochondria: Definition of Critical Regions and Residues in the Leader Peptide, Cell, 44:451-459 (1986).
Howard, K.A. Delivery of RNA interference therapeutics using polycation-based nanoparticles. Advanced Drug Delivery Reviews 61: 710-720 (2009).
Huang, Z. et al., Thiocholesterol-Based Lipids for Ordered Assembly of Bioresponsive Gene Carriers, Molecular Therapy, 11(3):409-417 (2005).
Huttenhofer, A. and Noller, H., Footprinting mRNA-ribosome complexes with chemical probes, The EMBO Journal, 13(16):3892-3901 (1994).
Incani, V. et al., Lipid and hydrophobic modification of cationic carriers on route to superior gene vectors. Soft Matter 6: 2124-2138 (2010).
International Preliminary Report on Patentability for PCT/US2010/058457, 12 pages (dated Jun. 14, 2012).
International Search Report for PCT/US2010/058457, 4 pages (dated May 6, 2011).
International Search Report for PCT/US2011/062459, 3 pages (dated Apr. 11, 2012).
International Search Report for PCT/US2012/041663, 4 pages (dated Oct. 8, 2012).
International Search Report for PCT/US2012/041724, 5 pages (dated Oct. 25, 2012).
International Search Report for PCT/US2013/034602, 2 pages (dated Jun. 17, 2013).
International Search Report for PCT/US2013/034604, 4 pages (dated Jun. 17, 2013).
International Search Report for PCT/US2013/044769, 4 pages (dated Nov. 12, 2013).
International Search Report for PCT/US2013/044771, 6 pages (dated Nov. 1, 2013).
International Search Report for PCT/US2013/073672, 6 pages (dated Mar. 3, 2014).
International Search Report for PCT/US2014/027422, 5 pages (dated Jul. 31, 2014).
International Search Report for PCT/US2014/027585, 3 pages (dated Jul. 14, 2014).
International Search Report for PCT/US2014/027602, 6 pages (dated Jul. 28, 2014).
International Search Report for PCT/US2014/027717, 5 pages (dated Jul. 16, 2014).
International Search Report for PCT/US2014/028330, 5 pages (dated Jul. 22, 2014).
International Search Report for PCT/US2014/028441, 6 pages (dated Jul. 22, 2014).
International Search Report for PCT/US2014/028498, 5 pages (dated Jul. 28, 2014).
International Search Report for PCT/US2014/061786, 6 pages (dated Feb. 6, 2015).
International Search Report for PCT/US2014/061793, 4 pages (dated Feb. 6, 2015).
International Search Report for PCT/US2014/061830, 5 pages (dated Feb. 4, 2015).
International Search Report for PCT/US2014/061841, 6 pages (dated Feb. 24, 2015).
International Search Report for PCT/US2015/21403 (4 pages) dated Jun. 15, 2015.
Jakobsen, K. et al., Purification of MRNA Directly From Crude Plant Tissues in 15 Minutes Using Magnetic Oligo DT Microspheres, Nucleic Acids Research, 18(12):3669 (1990).
Jani, B., et al., "In vitro Transcription and Capping of Gaussia Luciferase mRNA Followed by Hela Cell Transfection," J. Vis. Exp. (61), e3702, DOI: 10.3791/3702 (2012), 7 pages.
Jeffs, L.B. et al., A scalable, extrusion-free method for efficient liposomal encapsulation of plasmid DNA, Pharmacol. Res., 22(3): 362-372 (2005).
Jiang, G. et al., Hyaluronic acid-polyethyleneimine conjugate for target specific intracellular delivery of siRNA. Biopolymers 89 (7): 635-642 (2008).
Jiang, M. et al., Electrochemically controlled release of lipid/DNA complexes: a new tool for synthetic gene delivery system. Electrochemistry Communications (6): 576-582 (2004).
Jiang, S. and Cao, Z., Ultralow-fouling, functionalizable, and hydrolyzable zwitterionic materials and their derivatives for biological applications. Advanced Materials 22(9):920-932 (2010).
Jolck, R.I. et al., Solid-phase synthesis of PEGylated lipopeptides using click chemistry. Bioconjugate Chemistry 21(5):807-810 (2010).
Jon, S. et al., Degradable poly(amino alcohol esters) as potential DNA vectors with low cytotoxicity. Biomacromolecules 4(6):1759-1762 (2003).
Jones, G. et al., Duplex- and Triplex-Forming Properties of 4'-Thio-Modified Oligodeoxynucleotides, Bioorganic & Medicinal Chemistry Letters, 7(10):1275-1278 (1997).
Kabanov, A.V. and Kabanov, V.A., DNA complexes with polycations for the delivery of genetic material into cells. Bioconjugate Chemistry 6(1): 7-20 (1995).
Kahn et al., "Purification of Plasmid DNA by Tangential Flow Filtration", Biotech. Bioeng., 69(1):101-06 (2000).
Kamath, S. et al., Surface chemistry influences implant-mediated host tissue responses. Journal of Biomedical Materials Research A 86(3):617-626 (2007).
Kariko, K. et al., In vivo protein expression from mRNA delivered into adult rat brain, Journal of Neuroscience Methods, 105:77-86 (2001).
Kariko, K. et al., Incorporation of Pseudouridine Into mRNA Yields Superior Nonimmunogenic Vector With Increased Translational Capacity and Biological Stability, Molecular Therapy, 16(11): 1833-1840 (2008).
Kariko et al., "Generating the optimal mRNA for therapy: HPLC purification eliminates immune activation and improves translation of nucleoside-modified, protein-encoding mRNA", Nucleic Acids Research, pp. 1-10 (2011).
Kasuya, T. et al., In Vivo Delivery of Bionanocapsules Displaying *Phaseolus vulgaris* Agglutinin-L₄ Isolectin to Malignant Tumors Overexpressing N-Acetylglucosaminyltransferase V, Human Gene Therapy, 19:887-895 (2008).
Kaur, N. et al., A delineation of diketopiperazine self-assembly processes: understanding the molecular events involved in Nepsilon-(fumaroyl)diketopiperazine of L-Lys (FDKP) interactions. Molecular Pharmaceutics 5(2):294-315 (2007).
Kaur, T. et al., Addressing the Challenge: Current and Future Directions in Ovarian Cancer Therapy, Current Gene Therapy, 9: 434-458 (2009).
Keith et al., "Continuous Culture System for Production of Biopolymer Levan Using Erwinia herbicola" Biotech. Bioeng. 38:557-60 (1991).
Kiew, L.V. et al., Effect of antisense oligodeoxynucleotides for ICAM-1 on renal ischaemia-reperfusion injury in the anaesthetized rat, The Journal of Physiology, 557(3):981-989 (2004).
Kim, S.H. et al., Comparative evaluation of target-specific GFP gene silencing efficiencies for antisense ODN, synthetic siRNA, and siRNA plasmid complexed with PEI-PEG-FOL conjugate. Bioconjugate Chemistry 17(1): 241-244 (2006).

(56) References Cited

OTHER PUBLICATIONS

Kim, T. et al., Synthesis of biodegradable cross-linked poly(beta-amino ester) for gene delivery and its modification, inducing enhanced transfection efficiency and stepwise degradation. Bioconjugate Chemistry 16(5):1140-1148 (2005).

Klibanov, A.L. et al., Amphipathic polyethyleneglycols effectively prolong the circulation time of liposomes, FEBS, 268(1): 235-237 (1990).

Kober, L. et al., Optimized Signal Peptides for the Development of High Expressing CHO Cell Lines, Biotechnol. Bioeng., 110:1164-1173 (2012).

Kodama, K. et al., The Features and Shortcomings for Gene Delivery of Current Non-Viral Carriers, Current Medicinal Chemistry, 13: 2155-2161 (2006).

Kormann, M.S.D. et al., Expression of therapeutic proteins after delivery of chemically modified mRNA in mice, Nature Biotechnology, 29(2):154-157 (2011).

Kozak, M. An analysis of 5'-noncoding sequences from 699 vertebrate messenger RNAs, Nucleic Acid Research, 15(20):8125-8148 (1987).

Krieg et al., "Functional messenger RNAs are produced by SP6 in vitro transcript of cloned cDNAs" Nucleic Acids Research 12(18):7057-70 (1984).

Krieg, P.A. et al., In vitro RNA synthesis with SP6 RNA polymerase, Methods in Enzymology, 155:397-415 (1987).

Kvasnica, M. et al., Platinum(II) complexes with steroidal esters of L-methionine and L-histidine: Synthesis, characterization and cytotoxic activity, Bioorganic & Medicinal Chemistry, 16:3704-3713 (2008).

Lam, J.K.W et al., Pulmonary delivery of therapeutic siRNA, Advanced Drug Delivery Reviews (2011).

Lasic, D.D. et al., Gelation of liposome interior. A novel method for drug encapsulation, FEBS Letters, 312(2-3):255-258 (1992).

Lasic, D.D. Novel applications of liposomes, Trends in Biotechnology, 16:307-321 (1998).

Lee et al., "A Polynucleotide Segment Rich in Adenylic Acid in the Rapidly-Labeled Polyribosomal RNA Component of Mouse Sarcoma 180 Ascited Cells" PNAS 68 (6): 1331 (Jun. 1971).

Lee et al., "Tiny abortive initiation transcripts exert antitermination activity on an RNA hairpin-dependent intrinsic terminator", Nucleic Acids Research, 38(18): 6045-53 (2010).

Lee, S. et al., Stability and cellular uptake of polymerized siRNA (poly-siRNA)/polyethylenimine (PEI) complexes for efficient gene silencing. Journal of Controlled Release 141: 339-346 (2010).

Levy and Jomitz, "Types of Filtration," Adv Biochem Engin/Biotechnol 98:1-26 (2006).

Li, L. et al., Preparation and Gene Delivery of Alkaline Amino Acids-Based Cationic Liposomes, Archives of Pharmaceutical Research, 31(7):924-931 (2008).

Li, S. et al., In vivo gene transfer via intravenous administration of cationic lipid-protamine-DNA (LPD) complexes, Gene Therapy, 4:891-900 (1997).

Li, W. et al., Lipid-based Nanoparticles for Nucleic Acid Delivery, Pharmaceutical Research, 24(3):438-449 (2007).

Liebhaber, S.A. et al., Translation inhibition by an mRNA coding region secondary structure is determined by its proximity to the AUG initiation codon, Journal of Molecular Biology, 226(3):609-621 (1992).

Lim, Y. et al., A self-destroying polycationic polymer: biodegradable poly(4-hydroxy-1-proline ester). Journal of American Chemical Society 121: 5633-5639 (1999).

Lindgren, V. et al., Human Ornithine Transcarbamylase Locus Mapped to Band Xp21.1 Near the Duchenne Muscular Dystrophy Locus, Science, 226(2675):698-700 (1984).

Liu, X. et al., COStar: a D-star Lite-based Dynamic Search Algorithm for Codon Optimization, Journal of Theoretical Biology, 344:19-30 (2014).

Liu, Y. and Huang, L., Designer Lipids Advance Systematic siRNA Delivery, Molecular Therapy, 18(4):669-670 (2010).

Liu, Y. et al., Factors influencing the efficiency of cationic liposome-mediated intravenous gene delivery, Nature Biotechnology, 15:167-173 (1997).

Lo, K-M et al., High level expression and secretion of Fc-X fusion proteins in mammalian cells, Protein Engineering, 11(6):495-500 (1998).

Lorenzi, J. C. C. et al., Intranasal Vaccination with Messenger RNA as a New Approach in Gene Therapy: Use Against Tuberculosis, BMC Biotechnology, 10(77):1-11 (2010).

Love, K.T. et al., Lipid-like materials for low-dose, in vivo gene silencing, PNAS, 107(5):1864-1869 (2010).

Lu, D. et al., Optimization of methods to achieve mRNA-mediated transfection of tumor cells in vitro and in vivo employing cationic liposome vectors, Cancer Gene Therapy, 1(4):245-252 (1994).

Lukyanov, A.N. and Torchilin, V.P., Micelles from lipid derivatives of water-soluble polymers as delivery systems for poorly soluble drugs. Advanced Drug Delivery Reviews 56: 1273-1289 (2004).

Luo, D. and Saltzman, M., Synthetic DNA delivery systems. Nature Biotechnology 18: 33-37. Review (2000).

Lynn, D.M. and Langer, R., Degradable Poly(β-amino esters) :? Synthesis, Characterization, and Self-Assembly with Plasmid DNA. Journal of American Chemical Society 122(44): 10761-10768 (2000).

Lynn, D.M. et al., Accelerated discovery of synthetic transfection vectors: parallel synthesis and screening of a degradable polymer library. Journal of American Chemical Society 123 (33): 8155-8156 (2001).

Lynn, D.M. et al., pH-Responsive Polymer Microspheres: Rapid Release of Encapsulated Material within the Range of Intracellular pH. Angewandte Chemie International Edition 40(9): 1707-1710 (2001).

Ma, M. et al., Development of Cationic Polymer Coatings to Regulate Foreign Body Responses. Advanced Healthcare Materials 23: H189-H194. Reviews (2011).

Maclachlan, I., Lipid nanoparticle-mediated delivery of messenger RNA, 1st International mRNA Health Conference; Tubingen Germany, (Oct. 24, 2013) Retrieved from the Internet: URL: <http://files.shareholder.com/downloads/ABEA-50QJTB/2628241206x0x699789/47543d12-db34-4e6e-88a9-f3ae5d97b1d2/MacLachlan_mRNA_Conf_2013>.

Maeda-Mamiya, R. et al., In vivo gene delivery by cationic tetraamino; fullerene. Proceedings of National Academy of Sciences U S A, 107(12):5339-5344 (2010).

Malone, R.W., et al., Cationic liposome-mediated RNA transfection, PNAS, 86:6077-6081 (1989).

Mammal, http://en.wikipedia.org/wiki/Mammal, 2007, Pearson Education, NY, NY, Author unkown (Source: The international union for conservation of nature and natural resources), 2 pages, (Retrieved Aug. 2, 2014).

Mansour, H.M. et al., Nanomedicine in pulmonary delivery, International Journal of Nanomedicine, 4:299-319 (2009).

Margus, H. et al., Cell-penetrating peptides as versatile vehicles for oligonucleotide delivery. Molecular Therapy 20 (3): 525-533 (2012).

Martell, A.E. and Chaberek, S., The Preparation and the Properties of Some N,N'-Disubstituted-ethylenediaminedipropionic Acids. Journal of the American Chemical Society 72: 5357-5361 (1950).

Martin et al., "Tailing and 3'-end labeling of RNA with yeast poly(A) polymerase and carious nucleotides", RNA 4:226-30 (1998).

Martinon, F. et al., Induction of Virus-Specific Cytotoxic T Lymphocytes in Vivo by Liposome-Entrapped mRNA, European Journal of Immunology, 23(7):1719-1722 (1993).

Mathiowitz, E. and Langer, R., Polyanhydride microspheres as drug carriers I. Hot-melt microencapsulation. Journal of Controlled Release 5: 13-22 (1987).

Mathiowitz, E. et al., Novel microcapsules for delivery systems. Reactive Polymers 6: 275-283 (1987).

Mathiowitz, E. et al., Polyanhydride microspheres as drug carriers II. Microencapsulation by solvent removal. Journal of Applied Polymer Sciences 35: 755-774 (1988).

Mccracken, S. et al., 5'-Capping Enzymes are Targeted to Pre-MRNA by Binding to the Phosphorylated Carboxy-Terminal Domain of RNA Polymerase II, Genes and Development, 22(24):3306-3318 (1997).

(56) References Cited

OTHER PUBLICATIONS

Mcivor, R. S., Therapeutic Delivery of mRNA: The Medium is the Message, Molecular Therapy, 19(5):822-823 (2011).
Melton, D.A. et al., Efficient in vitro synthesis of biologically active RNA and RNA hybridization probes from; plasmids containing a bacteriophage SP6 promoter, Nucleic Acids Research, 12(18):7035-7056 (1984).
Melton et al., "Efficient in vitro synthesis of biologically active RNA hybridization probes from plasmids containing a bacteriophage SP6 promoter" Nucleic Acids Research 12 (18): 7037-7070 (1984).
Mendelsohn, J.D. et al., Rational design of cytophilic and cytophobic polyelectrolyte multilayer thin films. Biomacromolecules 4(1): 96-106 (2003).
Merkel, O.M. and Kissel, T., Nonviral Pulmonary Delivery of siRNA, Accounts of Chemical Research, 45(7):961-970 (2012).
Merten, O. et al., Large-Scale Manufacture and Characterization of a Lentiviral Vector Produced for Clinical Ex Vivo Gene Therapy Application, Human Gene Therapy, 22(3):343-356 (2011).
Miller, A. Cationic Liposomes for Gene Therapy. Angewandte Chemie International Edition 37: 1768-1785 (1998).
Monia, B.P. et al., Evaluation of 2'-Modified Oligonucleotides Containing 2'-Deoxy Gaps as Antisense Inhibitors of Gene Expression, The Journal of Biological Chemistry, 268(19):14514-14522 (1993).
Morrissey, D.V. et al., Potent and Persistent in vivo Anti-HBV Activity of Chemically Modified siRNAs, Nat. Biotechnol., 23(8): 1003-1007 (2005).
NANODROP Technical Support Bulletin T009, May 2007.
Narang, A.S. et al., Cationic lipids with increased DNA binding affinity for nonviral gene transfer in dividing and nondividing cells. Bioconjugate Chemistry 16(1): 156-168 (2005).
Novagen, "Bug Buster Protein Extraction Protocol/Reagent", User Protocol TB245 Rev. E 0304, pp. 1-8.
Navarro, G. et al., Phospholipid-polyethylenimine conjugate-based micelle-like nanoparticles for SiRNA delivery. Drug Delivery and Translational Research 1: 25-33 (2011).
Neamnark, A. et al., Aliphatic lipid substitution on 2 kDa polyethylenimine improves plasmid delivery and transgene expression. Molecular Pharmaceutics 6(6): 1798-1815 (2009).
Ng, J. et al., LincRNAs join the pluripotency alliance, Nature Genetics, 42:1035-1036 (2010).
Nguyen, D.N. et al., A novel high-throughput cell-based method for integrated quantification of type I interferons and in vitro screening of immunostimulatory RNA drug delivery. Biotechnology and Bioengineering 103(4): 664-675 (2009).
Nguyen, D.N. et al., Drug delivery-mediated control of RNA immunostimulation. Molecular Therapy 17(9): 1555-1562 (2009).
Nojima, T. et al., The Interaction between Cap-binding Complex and RNA Export Factor is Required for Intronless mRNA Export, Journal of Biological Chemistry, 282(21):15645-15651 (2007).
Nori, A. et al., Tat-conjugated synthetic macromolecules facilitate cytoplasmic drug delivery to human ovarian carcinoma cells, Bioconj. Chem., 14(1): 44-50 (2003).
Okumura, K. et al., Bax mRNA therapy using cationic liposomes for human malignant melanoma, The Journal of Gene Medicine, 10:910-917 (2008).
Otsuka, Y. et al., Identification of a Cytoplasmic Complex That Adds a Cap onto 5'-Monophosphate RNA, Molecular and Cellular Biology, 29(8):2155-2167 (2009).
Ozer, A., Alternative applications for drug delivery: nasal and pulmonary routes, Nanomaterials and Nanosystems for Biomedical Applications, M.R. Mozafari (ed.): 99-112 (2007).
Painter, H. et al., Topical Delivery of mRNA to the Murine Lung and Nasal Epithelium, Molecular Therapy, 9:S187 (2004).
Painter, H., An Investigation of mRNA as a Gene Transfer Agent, Oxford University GeneMedicine, Abstract Only, 1 page (2007).
Parrish, D.A. and Mathias, L.J., Five- and six-membered ring opening of pyroglutamic diketopiperazine. Journal of Organic Chemistry 67(6): 1820-1826 (2002).

Pardi et al., "In vitro transcription of long RNA containing modified nucleosides", *Methods in Molecular Biology*. vol. 969:Chapter 2 (2013).
Pascolo, "Vaccination with Messenger RNA (mRNA)," Handbook Experimental Pharmacology. 183:221-235 (2008).
Patton, J., Market Trends in Pulmonary Therapies, Trends and Opportunities, VI: 372-377. (2007).
Paulus, C. and Nevels, M., The Human Cytomegalovirus Major Immediate-Early Proteins as Antagonists of Intrinsic and Innate Antiviral Host Responses, Viruses, 1:760-779 (2009).
Peppas, N.A. et al., Hydrogels in Biology and Medicine: From Molecular Principles to Bionanotechnology. Advanced Materials 18: 1345-1360 (2006).
Philipp, A. et al., Hydrophobically modified oligoethylenimines as highly efficient transfection agents for siRNA delivery. Bioconjugate Chemistry 20(11): 2055-2061 (2009).
Pokroskaya et al., "In Vitro Transcription: Preparative RNA Yields in Analytical Scale Reactions", Analytical Biochemistry 220: 420-23 (1994).
Pons, M. et al., Liposomes obtained by the ethanol injection method, Int. J. Pharm., 95: 51-56. (1993).
Prata, C.A. et al., Lipophilic peptides for gene delivery. Bioconjugate Chemistry 19(2): 418-420 (2008).
Probst, J. et al., Spontaneous cellular uptake of exogenous messenger RNA in vivo is nucleic acid-specific, saturable and ion dependent, Gene Therapy, 14:1175-1180 (2007).
Promega, PolyATtract mRNA Isolation Systems, Instructions for Use of Products Z5200, Z5210, Z2300 and Z5310, Technical Manual (2012).
Putnam, D. Polymers for gene delivery across length scales. Nature Materials 5: 439-451 (2006).
Putnam, D. and Langer, R., Poly(4-hydroxy-1-proline ester): Low-Temperature Polycondensation and Plasmid DNA Complexation. Macromolecules 32(11): 3658-3662 (1999).
Qiagen, Oligotex Handbook, Second Edition (2002).
Rabinovich, P.M. et al., Synthetic Messenger RNA as a Tool for Gene Therapy, Human Gene Therapy, 17:1027-1035 (2006).
Raper, S.E. et al., Developing adenoviral-mediated in vivo gene therapy for ornithine transcarbamylase deficiency, Journal of Inherited Metabolic Disease, 21:119-137 (1998).
Ratajczak, J. et al., Membrane-derived microvesicles: important and underappreciated mediators of cell-to-cell communication, Leukemia, 20:1487-1495 (2006).
Ratner, B.D. and Bryant, S., Biomaterials: where we have been and where we are going. Annual Review of Biomedical Engineering 6: 41-75 (2004).
Reddy, A. et al., The Effect of Labour and Placental Separation on the Shedding of Syncytiotrophoblast Microparticles, Cell-free DNA and mRNA in Normal Pregnancy and Pre-eclampsia, Placenta, 29: 942-949 (2008).
Rejman, J. et al., Characterization and transfection properties of lipoplexes stabilized with novel exchangeable polyethylene glycol-lipid conjugates, Biochimica et Biophysica Acta, 1660:41-52 (2004).
Remington: The Science and Practice of Pharmacy, 21st Edition, Philadelphia, PA. Lippincott Williams & Wilkins (2005).
Rosemeyer et al., "Nonradioactive 3'-End-Labeling of RNA Molecules of Different Lengths by Terminal Deoxynucleotidyltransferase", Analytical Biochemistry, 224:446-9 (1995).
Rosenecker, J. et al., Gene Therapy for Cystic Fibrosis Lung Disease: Current Status and Future Perspectives, Curr. Opin. Mol. Ther., 8:439-445 (2006).
Rosenecker, J. et al., Interaction of Bronchoalveolar Lavage Fluid with Polyplexes and Lipoplexes: Analysing the Role of Proteins and Glycoproteins, J. Gene. Med., 5:49-60 (2003).
Ross et al., "In Vitro Synthesis of DNA Complementary to Purified Rabbit Globin mRNA", PNAS, 69(1): 264-8 (1972).
Rowe, S.M. et al., Cystic Fibrosis, New Engl. J. Med. 352:1992-2001 (2005).
Ryng, S. et al., Synthesis and structure elucidation of 5-aminomethinimino-3-methyl-4-isoxazolecarboxylic acid phenylamides and their immunological activity. Arch. Pharm. Pharm. Med. Chem 330(11):319-26 (1997).

(56) References Cited

OTHER PUBLICATIONS

Sahay, G. et al., Endocytosis of nanomedicines. Journal of Controlled Release 145: 182-195 (2010).
Sakiyama-Elbert, S.E. and Hubbell, J.A., Functional Biomaterials: Design of Novel Biomaterials. Annual Review of Materials Research 31: 183-201 (2001).
Schwartz et al., "Introduction to Tangential Flow Filtration for Laboratoty and Process Development Applications", Pall Corporation, 13 Pages downloaded from the internet on Aug. 3, 2017.
Schnierle, B.S. et al., Cap-specific mRNA (nucleoside-O2'-)-methyltransferase and poly(A) polymerase stimulatory activities of vaccinia virus are mediated by a single protein, Proceedings of the National Academy of Sciences, 89:2897-2901 (1992).
Schreier, H., The new frontier: gene and oligonucleotide therapy, Pharmaceutica Acta Helvetiae, 68(3):145-159 (1994).
Schwartz and Seeley, "Introduction to Tangential Flow Filtration for laboratory and Process Development Applications", Pall Scientific & Technical Report. PN 33213, pp. 1-12 (2002).
Semple, S.C. et al., Rational design of cationic lipids for siRNA delivery, Nature Biotechnology, 28(2): 172-176 (2010).
Shchori E., Poly(secondary Amine)s from Diacrylates and Diamines. Journal of Polymer Science 21(6):413-15 (1983).
Sherwood, R.F. Advanced drug delivery reviews: enzyme prodrug therapy, Adv. Drug Del. Rev., 22: 269-288 (1996).
Shimada, A. et al., Translocation Pathway of the Intratracheally Instilled Ultrafine Particles from the Lung into the Blood Circulation in the Mouse, Toxicologic Pathology, 34:949-957 (2006).
Siegwart, D.J. et al., Combinatorial synthesis of chemically diverse core-shell nanoparticles for intracellular delivery. Proceedings of the National Academy of the Sciences of the USA 108(32):12996-123001 (2011).
Smisterova, J. et al., Molecular Shape of the Cationic Lipid Controls the Structure of Cationic Lipid/Dioleylphosphatidylethanolamine-DNA Complexes and the Efficiency of Gene Delivery, The Journal of Biological Chemistry, 276(50):47615-47622 (2001).
Stern, L. et al., A novel antitumor prodrug platform designed to be cleaved by the endoprotease legumain, Bioconj. Chem., 20: 500-510 (2009).
Su, X. et al., Cytosolic Delivery Mediated Via Electrostatic Surface Binding of mRNA To Degradable Lipid-Coated Polymeric Nanoparticles, Polymer Preprints, 51(2):668-669 (2010).
Su, X. et al., In Vitro and in Vivo mRNA Delivery Using Lipid-Enveloped pH-Responsive Polymer Nanoparticles, Molecular Pharmaceutics, 8(3):774-787 (2011).
Suri, M. et al., Genetics for Pediatricians, Remedica Publishing, (2005).
Szoka, F. and Papahadjopoulos, D., Comparative properties and methods of preparation of lipid vesicles (liposomes). Annual Review of Biophysics Bioengineering 9: 467-508 (1980).
Tagawa, M. et al., Gene expression and active virus replication in the liver after injection of duck hepatitis B virus DNA into the peripheral vein of ducklings, Journal of Hepatology, 24:328-334 (1996).
Takahashi, Y. et al., Development of safe and effective nonviral gene therapy by eliminating CpG motifs from plasmid DNA vector, Frontiers in Bioscience, S4: 133-141 (2012).
Tan, S. et al., Engineering Nanocarriers for siRNA Delivery. Small 7(7): 841-856 (2011).
Tang, F. and Hughes, J. et al., Introduction of a Disulfide Bond into a Cationic Lipid Enhances Transgene Expression of Plasmid DNA, Biochemical and Biophysical Research Communications, 242(1):141-145 (1998).
Tang, M.X. et al., In vitro gene delivery by degraded polyamidoamine dendrimers. Bioconjugate Chemistry 7(6): 703-714 (1996).
Tarcha, P.J. et al., Synthesis and characterization of chemically condensed oligoethylenimine containing beta-aminopropionamide linkages for siRNA delivery. Biomaterials 28: 3731-3740 (2007).
Tavernier, G. et al., mRNA as gene therapeutic: How to control protein expression, Journal of Controlled Release, 150:238-247 (2011).

Third Party Preissuance Submission Under 37 CFR § 1.290 (Oct. 25, 2013).
Thomas, C. E. et al., Progress and problems with the use of viral vectors for gene therapy, Nature Reviews/Genetics, 4: 346-358 (2003).
Thompson, P.E. et al., Antiamebic action of 5-chloro-7-diethylaminomethyl-8-quinolinol and of other substituted 8-quinolinols in vitro and in experimental animals. American Journal of Tropical Medicine and Hygiene 2(4): 224-248 (1955).
Toki, B.E. et al., Protease-mediated fragmentation of p-amidobenzyl ethers: a new strategy for the activation of anticancer prodrugs, J. Org. Chem., 67(6): 1866-1872 (2002).
Tranchant, I. et al., Physicochemical optimisation of plasmid delivery by cationic lipids. Journal of Gene Medicine 6: S24-S35 (2004).
Tsui, N.B. et al., Stability of endogenous and added RNA in blood specimens, serum, and plasma, Clinical Chemistry, 48(10):1647-1653 (2002).
Tsvetkov, D.E. et al., Neoglycoconjugates based on dendrimeric poly(aminoamides). Russian Journal of Bioorganic Chemistry 28(6): 470-486 (2002).
Tuschl, T. et al., Targeted mRNA degradation by double-stranded RNA in vitro, Genes and Development, 13(24):3191-3197 (1999).
Uani, B., et al., "In vitro Transcription and Capping of Gaussia Luciferase mRNA Followed by Hela Cell Transfection;" U. Vis. Exp. (61), e3702, DOI: 10.3791/3702 (2012), 7 pages.
Urban-Klein, B. et al., RNAi-mediated gene-targeting through systemic application of polyethylenimine (PEI)-complexed siRNA in vivo. Gene Therapy 12(5): 461-466 (2005).
Van Balen, G.P. et al., Liposome/water lipophilicity: methods, information content, and pharmaceutical applications. Medicinal Research Reviews 24(3): 299-324 (2004).
Van De Wetering, P. et al., Structure-activity relationships of water-soluble cationic methacrylate/methacrylamide polymers for nonviral gene delivery. Bioconjugate Chemistry 10(4): 589-597 (1999).
Van Der Gun, B.T.F. et al., Serum insensitive, intranuclear protein delivery by the multipurpose cationic lipid Saint-2, Journal of Controlled Release, 123:228-238 (2007).
Van Tendeloo, V.F.I. et al., mRNA-based gene transfer as a tool for gene and cell therapy, Current Opinion in Molecular Therapeutics, 9(5):423-431 (2007).
Vandenbroucke, R.E. et al., Prolonged gene silencing in hepatoma cells and primary hepatocytes after small interfering RNA delivery with biodegradable poly(beta-amino esters). Journal of Gene Medicine 10: 783-794 (2008).
Varambally, S et al., Genomic Loss of microRNA-101 Leads to Overexpression of Histone Methyltransferase EZH2 in Cancer, Science, 322:1695-1699 (2008).
Veronese, F.M. et al., PEG-doxorubicin conjugates: influence of polymer structure on drug release, in vitro cytotoxicity, biodistribution, and antitumor activity, Bioconj. Chem., 16(4): 775-784 (2005).
Viecelli, H. et al., Gene Therapy for Hepatic Diseases Using Non-Viral Minicircle-DNA Vector, Journal of Inherited Metabolic Disease, 35(1):S144 (2012).
Viecelli, H. et al., Gene therapy for liver diseases using non-viral minicircle-DNA vector, Human Gene Therapy, 23(10):A145 (2012).
Viecelli, H. et al., Gene therapy for liver diseases using non-viral minicircle-DNA vector, Molecular Therapy, 21(1):S136 (2013).
Vomelova, I. et al., Methods of RNA Purification. All Ways (Should) Lead to Rome, Folia Biologica, 55(6):242-251 (2009).
Von Harpe et al., Characterization of commercially available and synthesized polyethylenimines for gene delivery. Journal of Controlled Release 69(2):309-322 (2000).
Voss et al., "A novel, non-radioactive eukaryotic in vitro transcription assay for sensitive quantification of RNA polymerase II activity," BMC Molecular Biology 15:7 1-14, (2014).
Walde, P. et al., Preparation of Vesicles (Liposomes). Encyclopedia of Nanoscience and Nanotechnology. Nalwa, ed. American Scientific Publishers, Los Angeles 9:43-79 (2004).
Wang, H. et al., N-acetylgalactosamine functionalized mixed micellar nanoparticles for targeted delivery of siRNA to liver, Journal of Controlled Release, 166(2):106-114 (2013).

(56) References Cited

OTHER PUBLICATIONS

Wang, Y. et al., Systemic delivery of modified mRNA encoding herpes simplex virus 1 thymidine kinase for targeted cancer gene therapy, Molecular Therapy, 21(2):358-367 (2013).
Webb, M. et al., Sphinogomyeline-cholesterol liposomes significantly enhance the pharmacokinetic and therapeutic properties of vincristine in murine and human tumour models, British Journal of Cancer, 72(4):896-904 (1995).
Weill et al., Nature Structural & Cellular Biology 19(6) : 577 (Year: 2012).
Weill, et al., Translational Control by Changes in Poly(A) Tail Length: Recycling mRNAs, Nature Structural & Molecular Biology, 19, 577-585 (2012).
Werth, S. et al., A low molecular weight fraction of polyethylenimine (PEI) displays increased transfection efficiency of DNA and siRNA in fresh or lyophilized complexes. Journal of Controlled Release 112: 257-270 (2006).
Wetzer, B. et al., Reducible cationic lipids for gene transfer, Biochem. J., 356:747-756 (2001).
White, J.E. et al., Poly(hydroxyaminoethers): A New Family of Epoxy-Based Thermoplastics. Advanced Materials 12(23): 1791-1800 (2000).
White, J.E. et al., Step-growth polymerization of 10,11-epoxyundecanoic acid. Synthesis and properties of a new hydroxy-functionalized thermopastic polyester. Advanced Materials 48: 3990-3998 (2007).
Whitehead, K.A. et al., Knocking down barriers: advances in siRNA delivery. Nature Reviews Drug Discovery 8(2): 129-139 (2009).
Wiehe, J.M. et al., mRNA-mediated gene delivery into human progenitor cells promotes highly efficient protein expression, Journal of Cellular and Molecular Medicine, 11(3):521-530 (2007).
Williams, D. et al., A simple, highly efficient method for heterologous expression in mammalian primary neurons using cationic lipid-mediated mRNA transfection, Frontiers in Neuroscience, 4(181):1-20 (2010).
Written Opinion for PCT/US2010/058457, 14 pages (dated May 6, 2011).
Written Opinion for PCT/US2011/062459, 9 pages (dated Apr. 11, 2012).
Written Opinion for PCT/US2012/041663, 7 pages (dated Oct. 8, 2012).
Written Opinion for PCT/US2012/041724, 11 pages (dated Oct. 25, 2012).
Written Opinion for PCT/US2013/034602, 4 pages (dated Jun. 17, 2013).
Written Opinion for PCT/US2013/034604, 9 pages (dated Jun. 17, 2013).
Written Opinion for PCT/US2013/044769, 8 pages (dated Nov. 12, 2013).
Written Opinion for PCT/US2013/044771, 7 pages (dated Nov. 1, 2013).
Written Opinion for PCT/US2013/073672, 7 pages (dated Mar. 3, 2014).
Written Opinion for PCT/US2014/027422, 6 pages (dated Jul. 31, 2014).
Written Opinion for PCT/US2014/027602, 7 pages (dated Jul. 28, 2014).
Written Opinion for PCT/US2014/027717, 5 pages (dated Jul. 16, 2014).
Written Opinion for PCT/US2014/028330, 7 pages (dated Jul. 22, 2014).
Written Opinion for PCT/US2014/028441, 6 pages (dated Jul. 22, 2014).
Written Opinion for PCT/US2014/028498, 6 pages (dated Jul. 28, 2014).
Written Opinion for PCT/US2014/061786, 5 pages (dated Feb. 6, 2015).
Written Opinion for PCT/US2014/061793, 4 pages (dated Feb. 6, 2015).
Written Opinion for PCT/US2014/061830, 7 pages (dated Feb. 4, 2015).
Written Opinion for PCT/US2015/21403 (7 pages) dated Jun. 15, 2015.
Wu, J. and Zern, M., Modification of liposomes for liver targeting, Journal of Hepatology, 24(6):757-763 (1996).
Wu, J. et al., Cationic lipid polymerization as a novel approach for constructing new DNA delivery agents. Bioconjugate Chemistry 12(2): 251-257 (2001).
Wurdinger, T. et al., A secreted luciferase for ex-vivo monitoring of in vivo processes, Nat. Methods, 5(2):171-173 (2008).
Wurm F.M., Review: Production of recombinant protein therapeutics in cultivated mammalian cells. Nature Biotechnology 22 (11): 1393 (Nov. 2004).
Yaffe et al., "LogSpin: a simple, economical and fast method for RNA isolation from infected or healthy plants and other eukaryotic tissues," BMC Research Notes. 5:45 (2012).
Yamamoto, A. et al., Current prospects for mRNA gene delivery, European Journal of Pharmaceutics and Biopharmaceutics, 71(3): 484-489 (2009).
Yamamoto, Y. et al., Important Role of the Proline Residue in the Signal Sequence that Directs the Secretion of Human Lysozyme in *Saccharomyces cerevisiae*, Biochemistry, 28:2728-2732 (1989).
Yasuda, M. et al., Fabry Disease: Novel [alpha]-Galactosidase A 3-terminal Mutations Result in Multiple Transcripts Due to Aberrant 3-End Formation, American Journal of Human Genetics, 73:162-173 (2003).
Ye, X. et al., Nucleic Acids, Protein Synthesis, and Molecular Genetics: Prolonged Metabolic Correction in Adult Ornithine Transcarbamylase-deficient Mice with Adenoviral Vectors, The Journal of Biological Chemistry, 271:3639-3646 (1996).
Yokoe, H. et al., Spatial dynamics of GFP-tagged proteins investigated by local fluorescence enhancement, Nature Biotechnology, 14(10):1252-1256 (1996).
Yoneda et al., A cell-penetrating peptidic GRP78 ligand for tumor cell-specific prodrug therapy, Bioorg. Med. Chem. Lett., 18(5): 1632-1636 (2008).
Yoshioka, Y. and Calvert, P., Epoxy-based Electroactive Polymer Gels. Experimental Mechanics 42(4): 404-408 (2002).
You et al., "Cosedimentation od PEA Root Polysomes with the Cytoskeleton", Cell Biology International Reports, 16(7): 663-73 (1992).
Zagridullin, P.H. et al., Monobasic amines. II. Cycloalkylation and hydroxyalkylation of cyclic and acyclic di- and polyamines. Journal of Organic Chemistry 26(1):184-88. Russian (1990).
Zaugg, H.E. et al., 3-Carboxy-2,5-piperazinedione and Derivatives. Journal of American Chemical Society 78(11):2626-2631 (1956).
Zauner, W. et al., Polylysine-based transfection systems utilizing receptor-mediated delivery. Advanced Drug Delivery Reviews 30(1-3):97-113(1998).
Zintchenko, A. et al., Simple modifications of branched PEI lead to highly efficient siRNA carriers with low toxicity. Bioconjugate Chemistry 19(7):1448-1455 (2008).
Zou, S. et al., Lipid-mediated delivery of RNA is more efficient than delivery of DNA in non-dividing cells, International Journal of Pharmaceutics, 389(1-2):232-243 (2010).

\* cited by examiner

```
SEQUENCE LISTING

Sequence total quantity: 6
SEQ ID NO: 1            moltype = RNA   length = 4443
FEATURE                 Location/Qualifiers
misc_feature            1..4443
                        note = Synthetic polynucleotide
source                  1..4443
                        mol_type = other RNA
                        organism = synthetic construct
SEQUENCE: 1
atgcagcggt cccgctcga aaaggccagt gtcgtgtcca aactcttctt ctcatggact    60
cggcctatcc ttagaaaggg gtatcggcag aggcttgagt tgtctgacat ctaccagatc   120
ccctcggtag attcggcgga taacctctcg gagaagctcg aacgggaatg ggaccgcgaa   180
ctcgcgtcta agaaaaaccc gaagctcatc aacgcactga gaaggtgctt cttctggcgg   240
ttcatgttct acggtatctt cttgtatctc ggggaggtca caaaagcagt ccaaccctg    300
ttgttgggtc gcattatcgc ctcgtacgac cccgataaca aagaagaacg gagcatcgcg   360
atctacctcg ggatcggact gtgtttgctt ttcatcgtca gaacacttt gttgcatcca   420
gcaatcttcg gcctccatca catcggtatg cagatgcgaa tcgctatgtt tagcttgatc   480
tacaaaaaga cactgaaact ctcgtcgcgg gtgttggata agatttccat cggtcagttg   540
gtgtccctgc ttagtaataa cctcaacaaa ttcgatgagg gactggcgct ggcacatttc   600
gtgtggattg ccccgttgca agtcgccctt ttgatgggcc ttatttggga gctgttgcag   660
gcatctgcct tttgtggcct gggatttctg attgtgttgg cattgtttca ggctgggctt   720
gggcggatga tgatgaagta tcgcgaccag agagcgggta aaatctcgga agactcgtc    780
atcacttcgg aaatgatcga aaacatccga tcggtcaaag cctattgctg ggaagaagct   840
atggagaaga tgattgaaaa cctccgccaa actgagctga aactgacccg caaggcggcg   900
tatgtccggt atttcaattc gtcagcgttc ttcttttccg ggttcttcgt tgtctttctc   960
tcggttttgc cttatgcctt gattaagggg attatcctcc gcaagatttt caccacgatt  1020
tcgttctgca ttgtattgcg catggcagtg acacggcaat ttccgtgggc cgtgcagaca  1080
tggtatgact cgcttggagc gatcaacaaa atccaagact tcttgcaaaa gcaagagtac  1140
aagaccctgg agtacaatct tactactacg gaggtagtaa tggagaatgt gacggctttt  1200
tgggaagagg gttttggaga actgtttgag aaagcaaagc agaataacaa caaccgcaag  1260
acctcaaatg gggacgattc cctgtttttc tcgaacttct ccctgctcgg aacacccgtg  1320
ttgaaggaca tcaatttcaa gattgagagg ggacagcttc tcgcggtagc gggaagcact  1380
ggtgcggaa aaactagcct cttgatggtg attatggggg agcttgagcc cagcgagggg  1440
aagattaaac actccgggcg tatctcattc tgtagccagt tttcatggat catgcccgga  1500
accattaaag agaacatcat tttcggagta tcctatgatg agtaccgata cagatcgtc   1560
attaaggcgt gccagttgga agaggacatt tctaagttcg ccgagaagga taacatcgtc  1620
ttgggagaag ggggtattac attgtcggga gggcagcgag cgcggatcag cctcgcgaga  1680
gcggtataca aagatgcaga tttgtatctg cttgattcac cgtttggata cctcgactga  1740
ttgacagaaa aagaaatctt cgagtcgtgc gtgtgtaaac ttatgctaa taagacgaga   1800
atcctggtga catcaaaaat ggaacacctt aagaaggcgg acaagatcct gatcctccac  1860
gaaggatcgt cctactttta cggcacttc tcagagttgc aaaacttgca gccggacttc   1920
tcaagcaaac tcatggggtg tgactcattc gaccagttca gcgcggaacg gcggaactcg  1980
atcttgacgg aaacgctgca ccgattctcg cttgaggtg atgccccggt atcgtggacg   2040
gagacaaaga agcagtcgtt taagcagaca ggagaatttg gtgagaaaag aagaacagt   2100
atcttgaatc ctattaactc aattcgcaag ttctcaatcg tccagaaaac tccactgcag  2160
atgaatggaa ttgaagagga ttcggacgaa ccctggagc gcaggcttag cctcgtgccg   2220
gattcagagc aagggaggc cattcttccc cggatttcgg tgatttcaac cggacctaca  2280
cttcaggcga ggcgaaggca atccgtgctc aacctcatga cgcattcggt aaaccagggg  2340
caaaacattc accgcaaaac gacggcctca acgagaaaag tgtcacttgc accccaggcg  2400
aatttgactg aactcgacat ctacagccgt aggctttcgc aagaaaccgg acttgagatc  2460
agcgaagaaa tcaatgaaga agatttgaaa gagtgtttct ttgatgacat ggaatcaatc  2520
ccagcggtga aacgtggaa cacatacttg cgttacatca cggtgcacaa gtccttgatt  2580
ttcgtcctca tctggtgtct cgtgatcttt ctcgctgagg tcgcagcgtc acttgtggtc  2640
ctctggctgc ttggtaatac gcccttgcaa gacaaaggca attctacaca ctcaagaaac  2700
aattcctatg ccgtgattat cacttctaca agtctcgtat acgtgtttta catctacgta  2760
ggagtggccg acactctgct cgcgatgggt ttcttccgag gactcccact cgttcacacg  2820
cttatcactg tctccaagat tctccaccat aagatgcttc atagcgtact gcaggctccc  2880
atgtccacct tgaatacgct caaggcggga ggtattttga atcgcttctc aaaagatatt  2940
```

```
gcaatttggg atgaccttct gcccctgacg atcttcgact tcatccagtt gttgctgatc  3000
gtgattgggg ctattgcagt agtcgctgtc ctccagcctt acattttgt  cgcgaccgtt  3060
ccggtgatcg tggcgtttat catgctgcgg gcctatttct tgcagacgtc acagcagctt  3120
aagcaactgg agtctgaagg gaggtcgcct atctttacgc atcttgtgac cagttttgaag 3180
ggattgtgga cgttgcgcgc cttttggcagg cagcccact  ttgaaacact gttccacaaa  3240
gcgctgaatc tccatacggc aaattggttt ttgtatttga gtaccctccg atggtttcag  3300
atgcgcattg agatgatttt tgtgatcttc tttatcgcgg tgactttat  ctccatcttg  3360
accacgggag agggcgaggg acgggtcggt attatcctga cactcgccat gaacattatg  3420
agcacttttgc agtgggcagt gaacagctcg attgatgtgg atagcctgat gaggtccgtt  3480
tcgagggtct ttaagttcat cgacatgccg acggagggaa agcccacaaa aagtacgaaa  3540
ccctataaga atgggcaatt gagtaaggta atgatcatcg agaacagtca cgtgaagaag  3600
gatgacatct ggcctagcgg gggtcagatg accgtgaagg acctgacggc aaaatacacc  3660
gagggaggga acgcaatcct tgaaaacatc tcgttcagca ttagccccgg tcagcgtgtg  3720
gggttgctcg ggaggaccgg gtcaggaaaa tcgacgttgc tgtcggcctt cttgagactt  3780
ctgaatacag agggtgagat ccagatcgac ggcgtttcgt gggatagcat caccttgcag  3840
cagtggcgga aagcgtttgg agtaatcccc caaaaggtct ttatctttag cggaaccttc  3900
cgaaagaatc tcgatcctta tgaacagtgg tcagatcaag agatttggaa agtcgcggac  3960
gaggttggcc ttcggagtgt aatcgagcag tttccgggaa aactcgactt tgtccttgta  4020
gatgggggat gcgtcctgtc gcatgggcac aagcagctca tgtcctggc  gcgatccgtc  4080
ctctctaaag cgaaaattct tctcttggat gaaccttcgg cccatctgga cccggtaacg  4140
tatcagatca tcagaaggac acttaagcag gcgtttgccg actgcacggt gattctctgt  4200
gagcatcgta tcgaggccat cgtcgaatgc cagcaatttc ttgtcatcga agagaataag  4260
gtccgccagt acgactccat ccagaagctg cttaatgaga gatcattgtt ccggcaggcc  4320
atttcaccat ccgataggt  gaaacttttt ccacacagaa attcgtcgaa gtgcaagtcc  4380
aaaccgcaga tcgcggcctt gaaagaagag actgaagaag aagttcaaga cacgcgtctt  4440
taa                                                                4443

SEQ ID NO: 2            moltype = RNA   length = 1653
FEATURE                 Location/Qualifiers
misc_feature            1..1653
                        note = Synthetic polynucleotide
source                  1..1653
                        mol_type = other RNA
                        organism = synthetic construct
SEQUENCE: 2
atggaagatg ccaaaaacat taagaagggc ccagcgccat tctacccact cgaagacggg  60
accgccggcg agcagctgca caaagccatg aagcgctacg ccctggtgcc cggcaccatc  120
gcctttaccg acgcacatat cgaggtggac attacctacg ccgagtactt cgagatgagc  180
gttcgctgg  cagaagctat gaagcgctat gggctgaata caaaccatcg gatcgtggtg  240
tgcagcgaga atagcttgca gttcttcatg cccgtgttgg gtgccctgtt catcggtgtg  300
gctgtggccc cagctaacga catctacaac gagcgcgagc tgctgaacag catgggcatc  360
agccagccca ccgtcgtatt cgtgagcaag aaagggctgc aaaagatcct caacgtgcaa  420
aagaagctac cgatcataca aaagatcatc atcatggata caagaccga  ctaccagggc  480
ttccaaagca tgtacacctt cgtgacttcc catttgccac ccggcttcaa cgagtacgac  540
ttcgtgcccg agagcttcga ccgggacaaa accatcgccc tgatcatgaa cagtagtggc  600
agtaccggat tgcccaaggg cgtagcccta cgcaccgca  ccgcttgtgt ccgattcagt  660
catgcccgcg accccatctt cggcaaccag atcatcccg  acaccgctat cctcagcgtg  720
gtgccatttc accacggctt cggcatgttc accacgctgg gctacttgat ctgcggcttt  780
cgggtcgtgc tcatgtaccg cttcgaggag gagctattct tgcgcagctt gcaagactat  840
aagattcaat ctgccctgct ggtgccaca  ctatttagct tcttcgctaa gagcactctc  900
atcgacaagt acgacctaag caacttgcac gagatcgcca gcggcggggc gccgctcagc  960
aaggaggtag gtgaggccgt ggccaaacgc ttccacctac caggcatccg ccagggctac  1020
ggcctgacag aaacaaccag cgccattctg atcacccccg aagggacga  caagcctggc  1080
gcagtaggca aggtggtgcc cttcttcgag gctaaggtgg tggacttgga caccggtaag  1140
acactgggtg taaccagcg  cggcgagctg tgcgtccgtg gccccatgat catgagcggc  1200
tacgttaaca accccgaggc tacaaacgct ctcatcgaca aggacggctg gctgcacagc  1260
ggcgacatcg cctactggga cgaggacgag cacttcttca tcgtggaccg gctgaagagc  1320
ctgatcaaat acaagggcta ccaggtagcc ccagccgaac tggagagcat cctgctgcaa  1380
caccccaaca tcttcgacgc cggggtcgcc ggcctgcccg acgacgatgc cggcgagctg  1440
cccgccgcag tcgtcgtgct ggaacacggt aaaaccatga ccgagaagga tcggtggac   1500
tatgtggcca gccaggttac aaccgccaag aagctgcgcg gtggtgttgt gttcgtggac  1560
gaggtgccta aggactgac  cggcaagttg gacgcccgca agatccgcga gattctcatt  1620
aaggccaaga agggcggcaa gatcgccgtg taa                                1653

SEQ ID NO: 3            moltype = RNA   length = 1239
FEATURE                 Location/Qualifiers
misc_feature            1..1239
                        note = Synthetic polynucleotide
source                  1..1239
                        mol_type = other RNA
                        organism = synthetic construct
SEQUENCE: 3
atgagcagca agggcagcgt ggtgctggcc tacagcggcg gcctggacac cagctgcatc  60
ctggtgtggc tgaaggagca gggctacgac gtgatcgcct acctggccaa catcggccag  120
aaggaggact cgaggaggc  ccgcaagaag gccctgaagc tgggcgccaa gaaggtgttc  180
atcgaggacg tgaccgcga  gttcgtggag gagttcatct ggcccgccat ccagagcagc  240
gccctgtacg aggaccgcta cctgctgggc accagcctgg cccgcccctg catcgcccgc  300
aagcaggtgg agatcgccca gcgcgagggc gccaagtacg tgagccacgg cgccaccggc  360
aagggcaacg accaggtgcg cttcgagctg agctgctaca gcctggcccc ccagatcaag  420
```

```
gtgatcgccc cctggcgcat gcccgagttc tacaaccgct tcaagggccg caacgacctg   480
atggagtacg ccaagcagca cggcatcccc atccccgtga cccccaagaa cccctggagc   540
atggacgaga acctgatgca catcagctac gaggccggca tcctggagaa ccccaagaac   600
caggcccccc ccggcctgta caccaagacc caggacccccg ccaaggcccc caacacccccc  660
gacatcctgg agatcgagtt caagaagggc gtgcccgtga aggtgaccaa cgtgaaggac   720
ggcaccaccc accagaccag cctggagctg ttcatgtacc tgaacgaggt ggccggcaag   780
cacggcgtgg gccgcatcga catcgtggag aaccgcttca tcggcatgaa gagccgcggc   840
atctacgaga ccccccgccgg caccatcctg taccacgccc acctggacat cgaggccttc   900
accatggacc gcgaggtgcg caagatcaag cagggcctgg gcctgaagtt cgccgagctg   960
gtgtacaccg gcttctggca cagccccgag tgcgagttcg tgcgccactg catcgccaag  1020
agccaggagc gcgtggaggg caaggtgcag gtgagcgtgc tgaagggcca ggtgtacatc  1080
ctgggccgcg agagcccct gagcctgtac aacgaggagc tggtgagcat gaacgtgcag  1140
ggcgactacg agcccaccga cgccaccggc ttcatcaaca tcaacagcct gcgcctgaag  1200
gagtaccacc gcctgcagag caaggtgacc gccaagtga                         1239

SEQ ID NO: 4               moltype = RNA  length = 140
FEATURE                    Location/Qualifiers
misc_feature               1..140
                           note = Synthetic polynucleotide
source                     1..140
                           mol_type = other RNA
                           organism = synthetic construct
SEQUENCE: 4
ggacagatcg cctggagacg ccatccacgc tgttttgacc tccatagaag acaccgggac    60
cgatccagcc tccgcggccg ggaacggtgc attggaacgc ggattccccg tgccaagagt   120
gactcaccgt ccttgacacg                                               140

SEQ ID NO: 5               moltype = RNA  length = 105
FEATURE                    Location/Qualifiers
misc_feature               1..105
                           note = Synthetic polynucleotide
source                     1..105
                           mol_type = other RNA
                           organism = synthetic construct
SEQUENCE: 5
cgggtggcat ccctgtgacc cctccccagt gcctctcctg gccctggaag ttgccactcc    60
agtgcccacc agccttgtcc taataaaatt aagttgcatc aagct                   105

SEQ ID NO: 6               moltype = RNA  length = 105
FEATURE                    Location/Qualifiers
misc_feature               1..105
                           note = Synthetic polynucleotide
source                     1..105
                           mol_type = other RNA
                           organism = synthetic construct
SEQUENCE: 6
gggtggcatc cctgtgaccc ctccccagtg cctctcctgg ccctggaagt tgccactcca    60
gtgcccacca gccttgtcct aataaaatta agttgcatca aagct                   105
```

METHODS FOR PURIFICATION OF MESSENGER RNA

CROSS-REFERENCE TO RELATED APPLICATIONS

This application is a continuation application of U.S. application Ser. No. 17/344,535, filed on Jun. 10, 2021 which is a continuation application of U.S. application Ser. No. 16/196,664, filed on Nov. 20, 2018, now U.S. Pat. No. 11,059,841, issued on Jul. 13, 2021 which is a continuation application of U.S. application Ser. No. 15/831,252, filed Dec. 4, 2017, now U.S. Pat. No. 10,155,785, issued on Dec. 18, 2018, which is a continuation application of U.S. application Ser. No. 14/696,140, filed on Apr. 24, 2015, now U.S. Pat. No. 9,850,269, issued on Dec. 26, 2017, which claims priority to U.S. Provisional Application Ser. No. 61/984,503, filed Apr. 25, 2014, the disclosure of which is hereby incorporated by reference.

BACKGROUND

Messenger RNA therapy is becoming an increasingly important approach for the treatment of a variety of diseases. Messenger RNA therapy involves administration of messenger RNA (mRNA) into a patient in need of the therapy and production of the protein encoded by the mRNA within the patient body. Thus, there is a great need for large scale production of highly pure and safe mRNA product suitable for therapeutic use.

INCORPORATION BY REFERENCE OF SEQUENCE LISTING

The instant application contains a Sequence Listing which has been filed electronically in XML format and is hereby incorporated by reference in its entirety. Said ASCII copy created on Jul. 5, 2022 is named "MRT-1134US6_ST26.xml" is 16 Kilobytes (KB) in size.

SUMMARY OF THE INVENTION

The present invention provides improved methods for effective purification of messenger RNA (mRNA), in particular, in vitro synthesized mRNA suitable for therapeutic use. The present invention is, in part, based on the surprising discovery that precipitation of mRNA followed by membrane filtration, a highly unusual combination, resulted in unexpectedly successful large scale production of high quality mRNA.

Thus, in one aspect, the present invention provides methods of purifying messenger RNA (mRNA) including the steps of (a) precipitating mRNA from an impure preparation; (b) subjecting the impure preparation comprising precipitated mRNA to a purification process involving membrane filtration such that the precipitated mRNA is captured by a membrane; and (c) eluting the captured precipitated mRNA from the membrane by re-solubilizing the mRNA, thereby resulting in a purified mRNA solution. In some embodiments, a purification process involving membrane filtration suitable for the present invention is tangential flow filtration. In some embodiments, a purification process involving membrane filtration suitable for the present invention is direct flow filtration.

In some embodiments, the step of precipitating mRNA comprises treating the impure preparation with a solution comprising a reagent selected from the group consisting of lithium chloride, sodium chloride, potassium chloride, guanidinium chloride, guanidinium thiocyanate, guanidinium isothiocyanate, ammonium acetate and combinations thereof. In some embodiments, a suitable reagent is guanidinium thiocyanate.

In some embodiments, a solution suitable for mRNA precipitation comprises guanidinium thiocyanate at a concentration of about 1 M or greater, of about 2 M or greater, of about 3 M or greater, of about 4 M or greater, of about 5 M or greater, of about 6 M or greater, of about 7 M or greater, of about 8 M or greater, of about 9 M or greater, or of about 10 M or greater. In some embodiments, a solution suitable for mRNA precipitation comprises guanidinium thiocyanate at a concentration of about 4M. In some such embodiments, a suitable solution further includes sodium lauryl sarcosyl and/or sodium citrate. For example, in certain embodiments, a solution suitable for mRNA precipitation comprises 4M guanidinium thiocyanate, 0.5% sodium lauryl sarcosyl, and 25 mM sodium citrate. In certain embodiments, a solution suitable for mRNA precipitation comprises 4M guanidinium thiocyanate, and 0.5% sodium lauryl sarcosyl. In certain embodiments, a solution suitable for mRNA precipitation comprises 4M guanidinium thiocyanate, and 25 mM sodium citrate.

In some embodiments, the step of precipitating mRNA further comprises a step of treating the impure preparation with absolute ethanol.

In some embodiments, the step of precipitating mRNA further comprises a step of treating the impure preparation with isopropyl alcohol.

In some embodiments, a membrane suitable for the present invention is made of material selected from the group consisting of polyethersulfone (mPES) (not modified), polyethersulfone (mPES) hollow fiber membrane, polyvinylidene fluoride (PVDF), cellulose acetate, nitrocellulose, MCE (mixed cellulose esters), ultra-high MW polyethylene (UPE), polyfluorotetraethylene (PTFE), nylon, and combination thereof.

In some embodiments, a method according to the invention further comprises washing the captured precipitated mRNA before eluting. In some embodiments, the washing step comprises multiple rinse cycles using a wash solution comprising a guanidinium buffer and ethanol, followed by about 70-80% ethanol (e.g., about 70%, 75%, or 80% ethanol). In some embodiments, the multiple rinse cycles suitable for the present invention are at least 5 or more than 5 cycles (e.g., about 5 to 10 cycles or about 5, 6, 7, 8, 9 or 10 cycles).

In some embodiments, the eluting step comprises re-solubilizing the captured precipitated mRNA with RNAse-free water. In some embodiments, the RNAse-free water is re-circulated for about 5-10 minutes (e.g., for about 5, 6, 7, 8, 9 or 10 minutes).

In some embodiments, a method according to the present invention further comprises a step of dialyzing the purified mRNA solution. In some embodiments, the purified mRNA solution is dialyzed with 1 mM sodium citrate using a 100 kDa molecular weight cut-off (MWCO) membrane.

In various embodiments, the present invention may be used to purify mRNA in vitro synthesized from an impure preparation containing an in vitro mRNA synthesis reaction mixture. In some embodiments, the impure preparation comprises prematurely aborted RNA sequences and/or enzyme reagents used in in vitro synthesis.

In some embodiments, the purified mRNA solution contains less than about 5% (e.g., less than about 4.5%, 4%, 3.5%, 3%, 2.5%, 2%, 1.5%, 1%, 0.5%, 0.1%) of prematurely aborted RNA sequences and/or enzyme reagents used in in vitro synthesis. In certain embodiments, the purified mRNA solution contains less than about 1% (e.g., less than about 0.9%, 0.8%, 0.7%, 0.6%, 0.5%) of prematurely aborted RNA sequences and/or enzyme reagents used in in vitro synthesis. In certain embodiments, the purified mRNA solution contains less than about 0.5% (e.g., less than about 0.4%, 0.3%, 0.2%, or 0.1%) of prematurely aborted RNA sequences and/or enzyme reagents used in in vitro synthesis. In some embodiments, the purified mRNA solution contains less than about 0.1% of prematurely aborted RNA sequences and/or enzyme reagents used in in vitro synthesis. In some embodiments, the purified mRNA solution is substantially free of prematurely aborted RNA sequences and/or enzyme reagents used in in vitro synthesis.

In some embodiments, the prematurely aborted RNA sequences and/or enzyme reagents used in in vitro synthesis are measured via silver stain, gel electrophoresis, high-performance liquid chromatography (HPLC), ultra-performance liquid chromatography (UPLC), and/or capillary electrophoresis.

In some embodiments, the prematurely aborted RNA sequences contain less than 15 bases (e.g., less than 14, 13, 12, 11, 10, 9, 8, 7, 6, 5, 4, or 3 bases). In some embodiments, the prematurely aborted RNA sequences contain about 8-15, 8-14, 8-13, 8-12, 8-11, or 8-10 bases.

In some embodiments, the enzyme reagents used in in vitro synthesis comprise T7 RNA polymerase, DNAse I, pyrophosphatase, and/or RNAse inhibitor.

In some embodiments, the mRNA is purified at a scale of or greater than 1 gram, 5 gram, 10 gram, 15 gram, 20 gram, 25 gram, 30 gram, 35 gram, 40 gram, 45 gram, 50 gram, 75 gram, 100 gram, 150 gram, 200 gram, 250 gram, 300 gram, 350 gram, 400 gram, 450 gram, 500 gram, 550 gram, 600 gram, 650 gram, 700 gram, 750 gram, 800 gram, 850 gram, 900 gram, 950 gram, 1 kg, 2.5 kg, 5 kg, 7.5 kg, 10 kg, 25 kg, 50 kg, 75 kg, or 100 kg per batch. As shown in the examples below, a batch comprising purified mRNA in the amount of 10 gram or greater (25 gram or more) can be achieved easily with the methods of the invention.

In some embodiments, the mRNA is purified before a cap and/or tail are added to the mRNA. In some embodiments, the mRNA is purified after a cap and/or tail are added to the mRNA. In some embodiments, the mRNA is purified after a cap is added. In some embodiments, the mRNA is purified both before and after a cap and/or tail are added to the mRNA.

In some embodiments, the mRNA is or greater than about 1 kb, 1.5 kb, 2 kb, 2.5 kb, 3 kb, 3.5 kb, 4 kb, 4.5 kb, 5 kb, 6 kb, 7 kb, 8 kb, 9 kb, 10 kb, 11 kb, 12 kb, 13 kb, 14 kb, 15 kb, or 20 kb in length.

In some embodiments, the mRNA comprises one or more modifications to enhance stability. In some embodiments, the one or more modifications comprise modified nucleotide and/or modified sugar phosphate backbones. In some embodiments, the mRNA is unmodified.

In some embodiments, the purified mRNA has an integrity of or greater than about 95% (e.g., of or greater than about 96%, 97%, 98%, or 99%). In some embodiments, the purified mRNA has an integrity of or greater than about 98%. In some embodiments, the purified mRNA has an integrity of or greater than about 99%.

In some embodiments, the present invention provides a method of purifying messenger RNA (mRNA), comprising (a) precipitating mRNA from an impure preparation; (b) subjecting the impure preparation comprising precipitated mRNA to tangential flow filtration such that the precipitated mRNA is captured by a filtration membrane while impurities are discarded through permeation; and (c) eluting the captured precipitated mRNA by re-solubilizing the precipitated mRNA, resulting in a purified mRNA solution.

In another aspect, the present invention provides a method for manufacturing messenger RNA (mRNA) comprising synthesizing mRNA in vitro; and purifying the in vitro synthesized mRNA using a method described herein.

Among other things, the present invention also provides a messenger RNA (mRNA) purified using a method described herein.

In another aspect, the present invention also provides a batch of purified mRNA comprising 5 gram or more of a single mRNA species suitable for administration to a human subject. In some embodiments, the batch comprises 10 gram of more of a single mRNA species. In some embodiments, the batch comprises 25 gram of more of a single mRNA species. In some embodiments, the batch is substantially free of impurities from an mRNA synthesis process. In some embodiments, the batch is substantially free of prematurely aborted RNA sequences, DNA templates, and/or enzyme reagents used in in vitro synthesis of the single mRNA species. In some embodiments, the purified mRNA contains less than about 5% of enzyme reagents used in in vitro synthesis. In some embodiments, the purified mRNA has an integrity greater than about 95%.

In another aspect, the present invention also provides a composition comprising messenger RNA purified using a method as described herein.

In another aspect, the present invention also provides a composition comprising in vitro synthesized messenger RNA, wherein the composition contains less than 1% of prematurely aborted RNA sequences and/or enzyme reagents used in in vitro synthesis.

In another aspect, the present invention also provides a composition comprising in vitro synthesized messenger RNA (mRNA), wherein the mRNA has an integrity of or greater than 95%.

As used in this application, the terms "about" and "approximately" are used as equivalents. Any numerals used in this application with or without about/approximately are meant to cover any normal fluctuations appreciated by one of ordinary skill in the relevant art.

Other features, objects, and advantages of the present invention are apparent in the detailed description that follows. It should be understood, however, that the detailed description, while indicating embodiments of the present invention, is given by way of illustration only, not limitation. Various changes and modifications within the scope of the invention will become apparent to those skilled in the art from the detailed description.

BRIEF DESCRIPTION OF THE DRAWING

The following figures are for illustration purposes only and not for limitation.

DEFINITIONS

Figure 1:
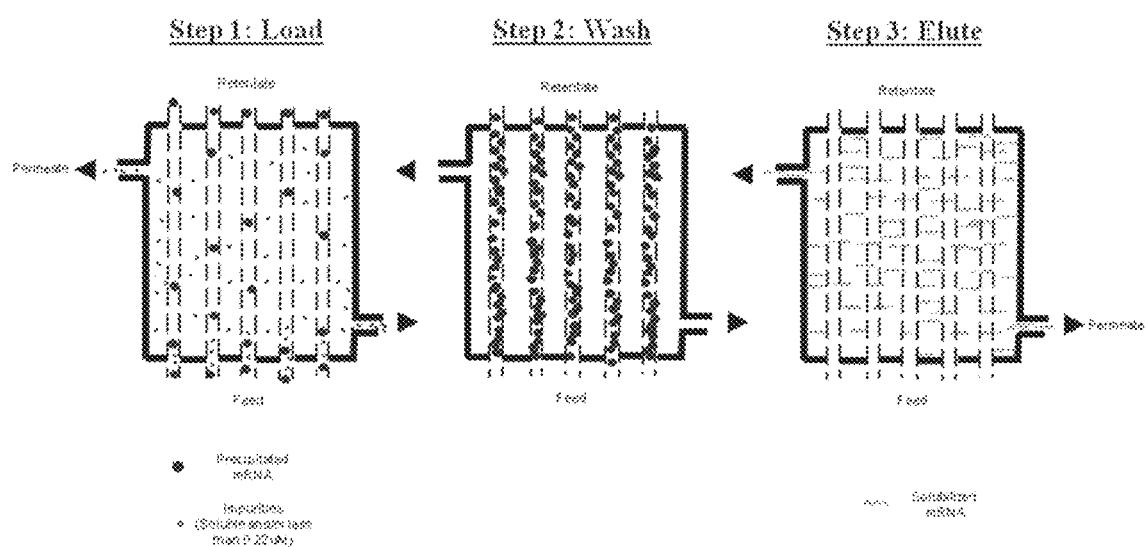
FIG. 1 depicts an exemplary process for large-scale purification of mRNA involving load, wash and elute steps. For example, the precipitated mRNA can be loaded to membranes such that the precipitated mRNA may be captured as retentate while soluble impurities as well as insoluble ones less than 0.22 um are discarded through the permeate. After capture, the solid precipitate is washed with various buffers followed by re-solubilization and elution for a pure messenger RNA product.

In order for the present invention to be more readily understood, certain terms are first defined below. Additional definitions for the following terms and other terms are set forth throughout the specification.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Biologically active: As used herein, the phrase "biologically active" refers to a characteristic of any agent that has activity in a biological system, and particularly in an organism. For instance, an agent that, when administered to an organism, has a biological effect on that organism, is considered to be biologically active.

Expression: As used herein, "expression" of a nucleic acid sequence refers to translation of an mRNA into a polypeptide, assembly of multiple polypeptides into an intact protein and/or post-translational modification of a polypeptide or fully assembled protein. In this application, the terms "expression" and "production," and grammatical equivalent, are used inter-changeably.

Functional: As used herein, a "functional" biological molecule is a biological molecule in a form in which it exhibits a property and/or activity by which it is characterized.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

Impurities: As used herein, the term "impurities" refers to substances inside a confined amount of liquid, gas, or solid, which differ from the chemical composition of the target material or compound. Impurities are also referred to as contaminants.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

messenger RNA (mRNA): As used herein, the term "messenger RNA (mRNA)" refers to a polynucleotide that encodes at least one polypeptide. mRNA as used herein encompasses both modified and unmodified RNA. mRNA may contain one or more coding and non-coding regions.

mRNA integrity: As used herein, the term "mRNA integrity" generally refers to the quality of mRNA. In some embodiments, mRNA integrity refers to the percentage of mRNA that is not degraded after a purification process (e.g., tangential flow filtration). mRNA integrity may be determined using methods well known in the art, for example, by RNA agarose gel electrophoresis (e.g., Ausubel et al., John Weley & Sons, Inc., 1997, Current Protocols in Molecular Biology).

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, Q(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre and post natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Prematurely aborted RNA sequences: The term "prematurely aborted RNA sequences", as used herein, refers to incomplete products of an mRNA synthesis reaction (e.g., an in vitro synthesis reaction). For a variety of reasons, RNA polymerases do not always complete transcription of a DNA template; i.e., RNA synthesis terminates prematurely. Possible causes of premature termination of RNA synthesis include quality of the DNA template, polymerase terminator sequences for a particular polymerase present in the template, degraded buffers, temperature, depletion of ribonucleotides, and mRNA secondary structures. Prematurely aborted RNA sequences may be any length that is less than the intended length of the desired transcriptional product. For example, prematurely aborted mRNA sequences may be less than 1000 bases, less than 500 bases, less than 100 bases, less than 50 bases, less than 40 bases, less than 30 bases, less than 20 bases, less than 15 bases, less than 10 bases or fewer.

Salt: As used herein the term "salt" refers to an ionic compound that does or may result from a neutralization reaction between an acid and a base.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Substantially free: As used herein, the term "substantially free" refers to a state in which relatively little or no amount of a substance to be removed (e.g., prematurely aborted RNA sequences) are present. For example, "substantially free of prematurely aborted RNA sequences" means the prematurely aborted RNA sequences are present at a level less than approximately 5%, 4%, 3%, 2%, 1.0%, 0.9%, 0.8%, 0.7%, 0.6%, 0.5%, 0.4%, 0.3%, 0.2%, 0.1% or less (w/w) of the impurity. Alternatively, "substantially free of prematurely aborted RNA sequences" means the prematurely aborted RNA sequences are present at a level less than about 100 ng, 90 ng, 80 ng, 70 ng, 60 ng, 50 ng, 40 ng, 30 ng, 20 ng, 10 ng, 1 ng, 500 pg, 100 pg, 50 pg, 10 pg, or less.

DETAILED DESCRIPTION

The present invention provides, among other things, improved methods for purifying mRNA from an impure preparation (e.g., in vitro synthesis reaction mixture) based on a process involving precipitating mRNA followed by membrane filtration (e.g., tangential flow filtration).

Various aspects of the invention are described in detail in the following sections. The use of sections is not meant to limit the invention. Each section can apply to any aspect of the invention. In this application, the use of "or" means "and/or" unless stated otherwise.

Synthesis of mRNA

The present invention may be used to purify any mRNA. mRNA is typically thought of as the type of RNA that carries information from DNA to the ribosome. The existence of mRNA is typically very brief and includes processing and translation, followed by degradation. Typically, in eukaryotic organisms, mRNA processing comprises the addition of a "cap" on the N-terminal (5') end, and a "tail" on the C-terminal (3') end. A typical cap is a 7-methylguanosine cap, which is a guanosine that is linked through a 5'-5'-triphosphate bond to the first transcribed nucleotide. The presence of the cap is important in providing resistance to nucleases found in most eukaryotic cells. The tail is typically a polyadenylation event whereby a polyadenylyl moiety is added to the 3' end of the mRNA molecule. The presence of this "tail" serves to protect the mRNA from exonuclease degradation. Messenger RNA is translated by the ribosomes into a series of amino acids that make up a protein.

mRNAs according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7 or SP6 RNA polymerase), DNAse I, pyrophosphatase, and/or RNAse inhibitor. The exact conditions will vary according to the specific application. The presence of these reagents is undesirable in the final product according to several embodiments and may thus be referred to as impurities and a preparation containing one or more of these impurities may be referred to as an impure preparation.

According to various embodiments, the present invention may be used to purify in vitro synthesized mRNA of a variety of lengths. In some embodiments, the present invention may be used to purify in vitro synthesized mRNA of or greater than about 1 kb, 1.5 kb, 2 kb, 2.5 kb, 3 kb, 3.5 kb, 4 kb, 4.5 kb, 5 kb 6 kb, 7 kb, 8 kb, 9 kb, 10 kb, 11 kb, 12 kb, 13 kb, 14 kb, 15 kb, or 20 kb in length. In some embodiments, the present invention may be used to purify in vitro synthesized mRNA ranging from about 1-20 kb, about 1-15 kb, about 1-10 kb, about 5-20 kb, about 5-15 kb, about 5-12 kb, about 5-10 kb, about 8-20 kb, or about 8-15 kb in length. For example, typical mRNAs may be about 1 kb to about 5 kb in length. More typically, the mRNA will have a length of about 1 kb to about 3 kb. However, in some embodiments, the mRNA in the composition of the invention is much longer (greater than about 20 kb). In some embodiments, the present invention may be used to purify mRNA containing one or more modifications that typically enhance stability. In some embodiments, one or more modifications are selected from modified nucleotide, modified sugar phosphate backbones, 5' and/or 3' untranslated region. In some embodiments, the present invention may be used to purify in vitro synthesized mRNA that is unmodified.

Typically, mRNAs are modified to enhance stability. Modifications of mRNA can include, for example, modifications of the nucleotides of the RNA. An modified mRNA according to the invention can thus include, for example, backbone modifications, sugar modifications or base modifications. In some embodiments, antibody encoding mRNAs (e.g., heavy chain and light chain encoding mRNAs) may be synthesized from naturally occurring nucleotides and/or nucleotide analogues (modified nucleotides) including, but not limited to, purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethylaminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g. from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosure of which is included here in its full scope by reference.

Typically, mRNA synthesis includes the addition of a "cap" on the N-terminal (5') end, and a "tail" on the C-terminal (3') end. The presence of the cap is important in providing resistance to nucleases found in most eukaryotic cells. The presence of a "tail" serves to protect the mRNA from exonuclease degradation.

Thus, in some embodiments, mRNAs include a 5' cap structure. A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A,G(5')ppp(5')A and G(5')ppp(5')G.

While mRNA provided from in vitro transcription reactions may be desirable in some embodiments, other sources of mRNA are contemplated as within the scope of the invention including wild-type mRNA produced from bacteria, fungi, plants, and/or animals.

In some embodiments, mRNAs include a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

The present invention may be used to purify mRNAs encoding a variety of proteins. Non-limiting examples of purification of mRNAs encoding firefly luciferase, argininosuccinate synthetase, Factor IX, and CFTR, are described in detail in the Examples section.

Typically, the present invention is used to purify a single mRNA species, i.e. the mRNA preparation to be purified contains mRNA derived from a single gene or a single synthesis or expression construct. In contrast, total mRNA purified from a cell contains multiple mRNA species.

A purification process according to the present invention may be carried out during or subsequent to synthesis. For example, mRNA may be purified as described herein before a cap and/or tail are added to the mRNA. In some embodiments, the mRNA is purified after a cap and/or tail are added to the mRNA. In some embodiments, the mRNA is purified after a cap is added. In some embodiments, the mRNA is purified both before and after a cap and/or tail are added to the mRNA. In general, a purification step as described herein may be performed after each step of mRNA synthesis, optionally along with other purification processes, such as dialysis. For example, mRNA may undergo dialysis to remove shortmers after initial synthesis (e.g., with or without a tail) and then be subjected to precipitation and purification as described herein, then after addition of the cap and/or tail, be purified again by precipitation and purification.

Precipitation of mRNA

According to the present invention, mRNA may be precipitated from an impure preparation, such as an in vitro synthesis reaction mixture, using various precipitation methods know in the art. As used herein, the term "precipitation" (or any grammatical equivalent thereof) refers to the formation of a solid in a solution. When used in connection with mRNA, the term "precipitation" refers to the formation of insoluble or solid form of mRNA in a liquid.

Any and all methods suitable for precipitating mRNA may be used to practice the present invention. Typically, mRNA precipitation involves a denaturing condition. As used herein, the term "denaturing condition" refers to any chemical or physical condition that can cause disruption of native confirmation of mRNA. Since the native conformation of a molecule is usually the most water soluble, disrupting the secondary and tertiary structures of a molecule may cause changes in solubility and may result in precipitation of mRNA from solution.

For example, a suitable method of precipitating mRNA from an impure preparation involves treating the impure preparation with a denaturing reagent such that the mRNA precipitates. Exemplary denaturing reagents suitable for the invention include, but are not limited to, lithium chloride, sodium chloride, potassium chloride, guanidinium chloride, guanidinium thiocyanate, guanidinium isothiocyanate, ammonium acetate and combinations thereof. Suitable reagent may be provided in a solid form or in a solution.

As a non-limiting example, guanidinium thiocyanate may be used to precipitate mRNA. Typically, guanidinium thiocyanate may be provided in a solution at a concentration of about 1 M or greater, of about 2 M or greater, of about 3 M or greater, of about 4 M or greater, of about 5 M or greater, of about 6 M or greater, of about 7 M or greater, of about 8 M or greater, of about 9 M or greater, or of about 10 M or greater. In some embodiments, a solution suitable for mRNA precipitation contains guanidinium thiocyanate at a concentration of about 4M.

In addition to denaturing reagent, a suitable solution for mRNA precipitation may include additional salt, surfactant and/or buffering agent. For example, a suitable solution may further include sodium lauryl sarcosyl and/or sodium citrate. As non-limiting examples, a solution suitable for mRNA precipitation may contain 4M guanidinium thiocyanate, 0.5% sodium lauryl sarcosyl, and 25 mM sodium citrate; or 4M guanidinium thiocyanate, and 0.5% sodium lauryl sarcosyl; or 4M guanidinium thiocyanate, and 25 mM sodium citrate.

Typically, it is desirable to incubate the impure preparation with one or more denaturing reagents described herein for a period of time at a desired temperature that permits precipitation of substantial amount of mRNA. For example, the mixture of an impure preparation and a denaturing agent may be incubated at room temperature or ambient temperature for a period of time. Typically, a suitable incubation time is a period of or greater than about 2, 3, 4, 5, 6, 7, 8, 9, 10, 15, 20, 25, 30, 40, 50, or 60 minutes. In some embodiments, a suitable incubation time is a period of or less than about 60, 55, 50, 45, 40, 35, 30, 25, 20, 15, 10, 9, 8, 7, 6, or 5 minutes. In some embodiments, the mixture is incubated for about 5 minutes at room temperature. Typically, "room temperature" or "ambient temperature" refers to a temperature with the range of about 20-25° C., for example, about 20° C., 21° C., 22° C., 23° C., 24° C., or 25° C. In some embodiments, the mixture of an impure preparation and a denaturing agent may also be incubated above room temperature (e.g., about 30-37° C. or in particular, at about 30° C., 31° C., 32° C., 33° C., 34° C., 35° C., 36° C., or 37° C.) or below room temperature (e.g., about 15-20° C. or in particular, at about 15° C., 16° C., 17° C., 18° C., 19° C., or 20° C.). The incubation period may be adjusted based on the incubation temperature. Typically, a higher incubation temperature requires shorter incubation time.

Alternatively or additionally, a solvent may be used to facilitate mRNA precipitation. Suitable exemplary solvent includes, but is not limited to, isopropyl alcohol, acetone, methyl ethyl ketone, methyl isobutyl ketone, ethanol, methanol, denatonium, and combinations thereof. For example, a solvent (e.g., absolute ethanol) may be added to an impure preparation together with a denaturing reagent or after the addition of a denaturing reagent and the incubation as described herein, to further enhance and/or expedite mRNA precipitation. Typically, after the addition of a suitable solvent (e.g., absolute ethanol), the mixture may be incubated at room temperature for another period of time. Typically, a suitable period of incubation time is or greater than about 2, 3, 4, 5, 6, 7, 8, 9, 10, 15, 20, 25, 30, 40, 50, or 60 minutes. In some embodiments, a suitable period of incubation is a period of or less than about 60, 55, 50, 45, 40, 35, 30, 25, 20, 15, 10, 9, 8, 7, 6, or 5 minutes. Typically, the mixture is incubated at room temperature for another about 5 minutes. Temperature above or below room may be used with proper adjustment of incubation time. Alternatively, incubation could occur at 4° C. or −20° C. for precipitation.

Typically, methods described herein result in precipitation of a substantial amount of mRNA from an impure preparation. In some embodiments, methods described herein result in precipitation of at least about 80%, 85%, 90%, 95%, 96%, 97%, 98%, or 99% of total mRNA from an impure preparation. In some embodiments, methods described herein result in precipitation of substantially 100% of total mRNA from an impure preparation.

Membrane Filtration

According to the present invention, an impure preparation containing the precipitated mRNA may be subjected to a purification process involving membrane filtration such that the precipitated mRNA is captured or retained by a membrane. Thus, in some embodiments, an impure preparation is subjected to membrane filtration following precipitation without pre-treatment to remove insolubles.

Various types of membrane filtration may be used to capture or retain precipitated mRNA. Typically, membrane filtration involves separating solids from fluids using one or more interposed permeable membranes. Membrane filtration may also be used to filter particles from a gaseous sample. Generally speaking, there are two major forms of membrane filtration, passive filtration, which proceeds solely due to solution-diffusion, and active filtration, which uses positive pressure or negative pressure (i.e. vacuum) to force the liquid or gas across the membrane.

An exemplary process involving membrane filtration for purifying mRNA is shown in FIG. 1. Typically, such a process involves load, wash and elute steps.

Load

Typically, the load step involves loading the feed (e.g., an impure preparation containing precipitated mRNA) onto a membrane and force it through by positive or negative pressure, leaving retentate captured or retained on the membrane. As used herein, the term "retentate" refers to any non-permeating solute and/or insoluble that is retained by a membrane. According to the present invention, precipitated mRNA is captured by a membrane as retentate. As used herein, the term "membrane" refers to any porous layer or sheet of material. In this application, the term "membrane" is used inter-changeably with filter.

In some embodiments, a suitable membrane has a pore size appropriate for capturing or retaining precipitated mRNA, while letting impurities (including soluble impurities and/or insoluble with size less than the pore size) pass through as permeate. In some embodiments, a suitable membrane has an average pore size of or greater than about 0.10 µm, 0.20 µm, 0.22 µm, 0.24 µm, 0.26 µm, 0.28 µm, 0.30 µm, 0.40 µm, 0.5 µm, or 1.0 µm. In a particular embodiments, a suitable membrane has an average pore size of about 0.22 µm. In some embodiments, appropriate pore size for retaining precipitated mRNA may be determined by the nominal molecular weight limits (NMWL) of the precipitated mRNA, also referred to as the molecular weight cut off (MWCO). Typically, a membrane with pore size less than the NMWL or MWCO of the precipitated mRNA is used. In some embodiments, a membrane with pore size two to six (e.g., 2, 3, 4, 5, or 6) times below the NMWL or MWCO of the precipitated mRNA is used. In some embodiments, a suitable membrane for the present invention may have pore size of or greater than about 100 kilodaltons (kDa), 300 kDa, 500 kDa, 1,000 kDa, 1,500 kDa, 2,000 kDa, 2,500 kDa, 3,000 kDa, 3,500 kDa, 4,000 kDa, 4,500 kDa, 5,000 kDa, 5,500 kDa, 6,000 kDa, 6,500 kDa, 7,000 kDa, 7,500 kDa, 8,000 kDa, 8,500 kDa, 9,000 kDa, 9,500 kDa, or 10,000 kDa.

A suitable membrane for the present invention may be made of any material. Exemplary membrane materials include, but are not limited to, polyethersulfone (mPES) (not modified), polyethersulfone (mPES) hollow fiber membrane, polyvinylidene fluoride (PVDF), cellulose acetate, nitrocellulose, MCE (mixed cellulose esters), ultra-high MW polyethylene (UPE), polyfluorotetraethylene (PTFE), nylon, polysulfone, polyether sulfone, polyacrilonitrile, polypropylene, polyvinyl chloride, and combination thereof.

A suitable membrane for the present invention may have various surface area. In some embodiments, a suitable membrane has a sufficiently large surface area to facilitate large scale production of mRNA. For example, a suitable membrane may have a surface area of or greater than about 2,000 $cm^2$, 2,500 $cm^2$, 3,000 $cm^2$, 3,500 $cm^2$, 4,000 $cm^2$, 4,500 $cm^2$, 5,000 $cm^2$, 7,500 $cm^2$, 10,000 $cm^2$, 5 $m^2$, 10 $m^2$, 12 $m^2$, 15 $m^2$, 20 $m^2$, 24 $m^2$, 25 $m^2$, 30 $m^2$, or 50 m2.

Membrane filtration may be performed in various format to capture precipitated mRNA. In some embodiments, membrane filtration is performed as part of tangential flow filtration (TFF).

Tangential flow filtration (TFF), also referred to as cross-flow filtration, is a type of filtration wherein the material to be filtered is passed tangentially across a filter rather than through it. In TFF, undesired permeate passes through the filter, while the desired retentate (e.g., precipitated mRNA) passes along the filter and is captured or retained on the filter or membrane downstream.

A principal advantage of tangential flow filtration is that non-permeable retentate that may aggregate in and block the filter (sometimes referred to as "filter cake") during traditional "dead-end" filtration, are instead carried along the surface of the filter. This advantage allows tangential flow filtration to be particularly suitable for large scale purification of precipitated mRNA. In some embodiments, a load of mRNA of or greater than about 1 gram, 10 gram, 50 gram, 100 gram, 200 gram, 300 gram, 400 gram, 500 gram, 600 gram, 700 gram, 800 gram, 900 gram, 1 kg, 5 kg, 10 kg, 50 kg, or 100 kg may be applied per batch.

At least three process variables that are important in a typical TFF process: the transmembrane pressure, feed rate, and flow rate of the permeate. The transmembrane pressure is the force that drives fluid through the filter, carrying with it permeable molecules. In some embodiments, the transmembrane pressure is between 1 and 30 pounds per square inch (psi), inclusive.

The feed rate (also known as the crossflow velocity) is the rate of the solution flow through the feed channel and across the filter. The feed rate determines the force that sweeps away molecules that may otherwise clog or foul the filter and thereby restrict filtrate flow. In some embodiments, the feed rate is between 1 and 500 L/minute. In some embodiments, the feed rate is between 50 and 800 mL/minute. In some embodiments, the feed rate is between 50 and 750 mL/minute. In some embodiments, the feed rate is between 50 and 300 mL/minute. In some embodiments, the feed rate is between 50 and 200 mL/minute. In some embodiments, the feed rate is between 75 and 200 mL/minute. In some embodiments, the feed rate is between 100 and 200 mL/minute. In some embodiments, the feed rate is between 125 and 175 mL/minute. In some embodiments, the feed rate is 130 mL/minute. In some embodiments, the feed rate is between 60 mL/min and 220 mL/min. In some embodiments, the feed rate is 60 mL/min or greater. In some embodiments, the feed rate is 100 mL/min or greater. In some embodiments, the feed rate is 150 mL/min or greater. In some embodiments, the feed rate is 200 mL/min or greater. In some embodiments, the feed rate is 220 mL/min or greater.

The flow rate of the permeate is the rate at which the permeate is removed from the system. For a constant feed rate, increasing permeate flow rates can increase the pressure across the filter, leading to enhanced filtration rates while also potentially increasing the risk of filter clogging or fouling. The principles, theory, and devices used for TFF are described in Michaels et al., "Tangential Flow Filtration" in Separations Technology, Pharmaceutical and Biotechnology Applications (W. P. Olson, ed., Interpharm Press, Inc., Buffalo Grove, Ill. 1995). See also U.S. Pat. Nos. 5,256,294 and 5,490,937 for a description of high-performance tangential flow filtration (HP-TFF), which represents an improvement to TFF. In some embodiments, the flow rate is between 1 and 100 L/minute. In some embodiments, the flow rate is between 10 and 100 mL/minute. In some embodiments, the flow rate is between 10 and 90 mL/minute. In some embodiments, the flow rate is between 10 and 80 mL/minute. In some embodiments, the flow rate is between 10 and 70 mL/minute. In some embodiments, the flow rate is between 10 and 60 mL/minute. In some embodiments, the flow rate is between 10 and 50 mL/minute. In some embodiments, the flow rate is between 10 and 40 mL/minute. In some embodiments, the flow rate is between 20 and 40 mL/minute. In some embodiments, the flow rate is 30 mL/minute.

Any combinations of various process variables described herein may be used. In some embodiments, the tangential flow filtration is performed at a feed rate of approximately 100-200 mL/minute (e.g., approximately 100-180 mL/minute, 100-160 mL/minute, 100-140 mL/minute, 110-190 mL/minute, 110-170 mL/minute, or 110-150 mL/minute) and/or a flow rate of approximately 10-50 mL/minute (e.g., approximately 10-40 mL/minute, 10-30 mL/minute, 20-50 mL/minute, or 20-40 mL/minute). In some embodiments, the tangential flow filtration is performed at a feed rate of approximately 100, 110, 120, 130, 140, 150, 160, 170, 180, 190, or 200 mL/minute and/or a flow rate of approximately 10, 20, 30, 40, or 50 mL/minute. In other embodiments, the tangential flow filtration is performed at a feed rate of approximately 500, 750 mL/minute, 1, 2, 3, 4, or 5 L/min and/or a flow rate of approximately 100, 200, 250, 500, 750 mL/minute or 1 L/min.

Wash

Typically, the captured insoluble mRNA may be washed before eluting to get rid of impurities retained on the membrane. In some embodiments, a wash step comprises multiple rinse cycles using one or more wash solutions. For example, a wash step may be carried out by multiple rinse cycles using a guanidinium buffer and ethanol, followed by 70-80% ethanol (e.g., about 70%, 75%, or 80% ethanol). In certain embodiments, the multiple rinse cycles is more than 2, more than 3, more than 4, more than 5, more than 6, more than 7, more than 8, more than 9, or more than 10 cycles.

Elute

Typically, captured or retained mRNA may be eluted by re-solubilizing the precipitated mRNA into a solution. For example, captured mRNA may be eluted with RNAse-free water. In certain embodiments, eluting the captured mRNA involves recirculating the RNAse-free water. For example, the RNAse-free water may be circulated for about 5-30 minutes (e.g., about 5-25 minutes, about 5-20 minutes, or about 5-15 minutes). In particular embodiments, the RNAse-free water is re-circulated for about 5-10 minutes (e.g., for about 5, 6, 7, 8, 9 or 10 minutes).

In some embodiments, re-solubilized mRNA may be dialyzed into a desired formulation at a desired concentration. Various formulations may be used for dialysis. In some embodiments, the purified mRNA solution is dialyzed with 1 mM sodium citrate. In some embodiments, the purified mRNA solution is dialyzed with sodium acetate, ammonium carbonate, ammonium bicarbonate, pyridinium acetate, pyridinium formate, ammonium acetate, urea, potassium chloride, etc. Depending on the size of mRNA of interest, dialysis membranes with appropriate molecular weight cut-off (MWCO) may be used. For example, suitable dialysis membranes may have a MWCO of about 50 kDa, 60 kDa, 70 kDa, 80 kDa, 90 kDa, 100 kDa, 150 kDa, 200 kDa, 250 kDa, 300 kDa, 350 kDa, 400 kDa, 450 kDa, or 500 kDa.

Characterization of Purified mRNA

A particular advantage provided by the present invention is the ability to purify mRNA, in particular, mRNA synthesized in vitro, at a large or commercial scale. For example, in vitro synthesized mRNA may be purified at a scale of or greater than about 1 gram, 10 gram, 50 gram, 100 gram, 200 gram, 300 gram, 400 gram, 500 gram, 600 gram, 700 gram, 800 gram, 900 gram, 1 kg, 5 kg, 10 kg, 50 kg, or 100 kg per batch. In one particular embodiment, in vitro synthesized mRNA may be purified at a scale of 10 gram per batch. In another particular embodiment, in vitro synthesized mRNA may be purified at a scale of 100 gram per batch. In yet another particular embodiment, in vitro synthesized mRNA may be purified at a scale of 1 kg per batch.

In various embodiments, mRNA purified according to the present invention is substantially free of impurities from mRNA synthesis process including, but not limited to, prematurely aborted RNA sequences, DNA templates, and/or enzyme reagents used in in vitro synthesis.

In particular, the present invention removes or eliminates a high degree of prematurely aborted RNA sequences (also known as "shortmers"). In some embodiments, a method according to the invention removes more than about 90%, 95%, 96%, 97%, 98%, 99% or substantially all prematurely aborted RNA sequences. In some embodiments, mRNA purified according to the present invention is substantially free of prematurely aborted RNA sequences. In some embodiments, mRNA purified according to the present invention contains less than about 5% (e.g., less than about 4%, 3%, 2%, or 1%) of prematurely aborted RNA sequences. In some embodiments, mRNA purified according to the present invention contains less than about 1% (e.g., less than about 0.9%, 0.8%, 0.7%, 0.6%, 0.5%, 0.4%, 0.3%, 0.2%, or 0.1%) of prematurely aborted RNA sequences. In some embodiments, mRNA purified according to the present invention contains undetectable prematurely aborted RNA sequences as determined by, e.g., eithidium bromide and/or Coomassie staining. In some embodiments, prematurely aborted RNA sequences comprise less than 15 bases (e.g., less than 14, 13, 12, 11, 10, 9, 8, 7, 6, 5, 4, or 3 bases). In some embodiments, the prematurely aborted RNA sequences contain about 8-15, 8-14, 8-13, 8-12, 8-11, or 8-10 bases.

In some embodiments, a method according to the present invention removes or eliminates a high degree of enzyme reagents used in in vitro synthesis including, but not limited to, T7 RNA polymerase, DNAse I, pyrophosphatase, and/or RNAse inhibitor. In some embodiments, the present invention is particularly effective to remove T7 RNA polymerase. In some embodiments, a method according to the invention removes more than about 90%, 95%, 96%, 97%, 98%, 99% or substantially all enzyme reagents used in in vitro synthesis including. In some embodiments, mRNA purified according to the present invention is substantially free of enzyme reagents used in in vitro synthesis including. In some embodiments, mRNA purified according to the present invention contains less than about 5% (e.g., less than about 4%, 3%, 2%, or 1%) of enzyme reagents used in in vitro synthesis including. In some embodiments, mRNA purified according to the present invention contains less than about 1% (e.g., less than about 0.9%, 0.8%, 0.7%, 0.6%, 0.5%, 0.4%, 0.3%, 0.2%, or 0.1%) of enzyme reagents used in in vitro synthesis including. In some embodiments, mRNA purified according to the present invention contains undetectable enzyme reagents used in in vitro synthesis including as determined by, e.g., ethidium bromide and/or Coomassie staining.

The level of prematurely aborted RNA sequences and/or enzyme reagents in the purified mRNA may be measured using various methods known in the art. For example, the prematurely aborted RNA sequences and/or enzyme reagents used in in vitro synthesis may be measured via silver stain, gel electrophoresis, high-performance liquid chromatography (HPLC), ultra-performance liquid chromatography (UPLC), and/or capillary electrophoresis.

In various embodiments, mRNA purified using a method described herein maintain high degree of integrity. As used herein, the term "mRNA integrity" generally refers to the quality of mRNA after purification. In some embodiments, mRNA integrity refers to the percentage of mRNA that is not degraded after tangential flow filtration. mRNA integrity may be determined using methods well known in the art, for example, by RNA agarose gel electrophoresis (e.g., Ausubel et al., John Weley & Sons, Inc., 1997, Current Protocols in Molecular Biology). In some embodiments, mRNA purified according to the present invention has an integrity greater than about 95% (e.g., greater than about 96%, 97%, 98%, 99% or more). In some embodiments, mRNA purified according to the present invention has an integrity greater than 98%. In some embodiments, mRNA purified according to the present invention has an integrity greater than 99%. In some embodiments, mRNA purified according to the present invention has an integrity of approximately 100%.

Large-scale batch production of mRNA for therapeutic applications

The present invention addresses an urgent need for the large-scale production of purified mRNAs that have the high degree of purity and integrity required for therapeutic applications. Existing methods are typically small in scale and cannot be scaled up to the extent that is required to make commercial production of mRNA that is suitable for administration to a human subject sufficiently cost-effective. In contrast, the methods of the invention are fully scalable as demonstrated in the examples and allow the cost-effective large-scale production of pharmaceutical-grade mRNA.

Each batch of purified mRNA produced in accordance with the invention comprises 5 gram or more of a single mRNA species suitable for administration to a human subject. In some embodiments, a single batch comprises 10 gram or more of a single mRNA species. In a particular embodiment, a single batch comprises 25 gram or more of a single mRNA species.

The method of the invention yields purified mRNA batches that are substantially free of impurities from an mRNA synthesis process. In particular, the batches are substantially free of prematurely aborted RNA sequences, DNA templates, and/or enzyme reagents used in in vitro synthesis of the single mRNA species. For example, a batch of purified mRNA produced in accordance with the invention contains less than about 5% of enzyme reagents used in in vitro synthesis. The purified mRNA in each batch typically has an integrity greater than about 95%.

The mRNA batches produced in accordance with the methods of the invention can be used for to prepare a therapeutic agent, requiring one or more downstream processing step(s). Typically, each mRNA batch will be formulated, e.g. by encapsulating the mRNA into lipid nanoparticles, liposomes, polymer-based polyplexes, etc. that can be administered to a patient. Typical routes of administration, but not exclusively, involve intravenous or pulmonary delivery of the purified mRNA.

EXAMPLES

Example 1. Generation and Purification of Messenger RNA (mRNA)

Messenger RNA Synthesis

Firefly Euciferase (FFL), Argininosuccinate Synthetase (ASS1), and human Cystic Fibrosis Transmembrane Conductance Regulator (CFTR) messenger RNA were synthesized by in vitro transcription from a plasmid DNA template encoding the gene, which was followed by the addition of a 5' cap structure (Cap 1) (Fechter, P.; Brownlee, G. G. "Recognition of mRNA cap structures by viral and cellular proteins" J. Gen. Virology 2005, 86, 1239-1249) and a 3' poly(A) tail of approximately 200 nucleotides in length as determined by gel electrophoresis. 5' and 3' untranslated regions present in each mRNA product are represented as X and Y, respectively and defined as stated (vide infra). The synthesis of the target messenger RNA construct involved a two-step process in which the initial strand consisting of the coding sequence flanked by 5' and 3' untranslated regions is synthesized. This uncapped and untailed construct was purified and processed further via a capping step, followed by a poly-A addition tailing step. A second purification step at the conclusion of the tailing reaction was performed in a similar fashion to the initial purification process.

Exemplary Codon-Optimized Cystic Fibrosis Transmembrane Conductance Regulator (CFTR) mRNA Construct Design:

$X_1$-SEQ ID NO: 1-$Y_1$ [SEQ ID NO: 1]

```
AUGCAGCGGUCCCCGCUCGAAAAGGCCAGUGUCGUGUCCAAACUCUUCUUCUCAU
GGACUCGGCCUAUCCUUAGAAAGGGGUAUCGGCAGAGGCUUGAGUUGUCUGACA
UCUACCAGAUCCCCUCGGUAGAUUCGGCGGAUAACCUCUCGGAGAAGCUCGAACG
GGAAUGGGACCGCGAACUCGCGUCUAAGAAAAACCCGAAGCUCAUCAACGCACUG
AGAAGGUGCUUCUUCUGGCGGUUCAUGUUCUACGGUAUCUUCUUGUAUCUCGGG
GAGGUCACAAAAGCAGUCCAACCCCUGUUGUUGGGUCGCAUUAUCGCCUCGUACG
ACCCCGAUAACAAAGAAGAACGGAGCAUCGCGAUCUACCUCGGGAUCGGACUGUG
UUUGCUUUUCAUCGUCAGAACACUUUUGUUGCAUCCAGCAAUCUUCGGCCUCCAU
CACAUCGGUAUGCAGAUGCGAAUCGCUAUGUUUAGCUUGAUCUACAAAAAGACA
CUGAAACUCUCGUCGCGGGUGUUGGAUAAGAUUUCCAUCGGUCAGUUGGUGUCC
CUGCUUAGUAAUAACCUCAACAAAUUCGAUGAGGGACUGGCGCUGGCACAUUUC
GUGUGGAUUGCCCCGUUGCAAGUCGCCCUUUUGAUGGGCCUUAUUUGGGAGCUG
UUGCAGGCAUCUGCCUUUUGUGGCCUGGGAUUUCUGAUUGUGUUGGCAUUGUUU
CAGGCUGGGCUUGGGCGGAUGAUGAUGAAGUAUCGCGACCAGAGAGCGGGUAAA
AUCUCGGAAAGACUCGUCAUCACUUCGGAAAUGAUCGAAAACAUCCAGUCGGUCA
AAGCCUAUUGCUGGGAAGAAGCUAUGGAGAAGAUGAUUGAAAACCUCCGCCAAA
CUGAGCUGAAACUGACCCGCAAGGCGGCGUAUGUCCGGUAUUUCAAUUCGUCAGC
GUUCUUCUUUUCCGGGUUCUUCGUUGUCUUUCUCUCGGUUUUGCCUUAUGCCUUG
AUUAAGGGGAUUAUCCUCCGCAAGAUUUUCACCACGAUUUCGUUCUGCAUUGUA
UUGCGCAUGGCAGUGACACGGCAAUUUCCGUGGGCCGUGCAGACAUGGUAUGAC
UCGCUUGGAGCGAUCAACAAAAUCCAAGACUUCUUGCAAAAGCAAGAGUACAAG
ACCCUGGAGUACAAUCUUACUACUACGGAGGUAGUAAUGGAGAAUGUGACGGCU
UUUUGGGAAGAGGGUUUUGGAGAACUGUUUGAGAAAGCAAAGCAGAAUAACAAC
AACCGCAAGACCUCAAAUGGGGACGAUUCCCUGUUUUUCUCGAACUUCUCCCUGC
UCGGAACACCCGUGUUGAAGGACAUCAAUUUCAAGAUUGAGAGGGGACAGCUUC
UCGCGGUAGCGGGAAGCACUGGUGCGGGAAAAACUAGCCUCUUGAUGGUGAUUA
UGGGGGAGCUUGAGCCCAGCGAGGGGAAGAUUAAACACUCCGGGCGUAUCUCAU
UCUGUAGCCAGUUUUCAUGGAUCAUGCCCGGAACCAUUAAAGAACAUCAUUU
UCGGAGUAUCCUAUGAUGAGUACCGAUACAGAUCGGUCAUUAAGGCGUGCCAGU
```

-continued

```
UGGAAGAGGACAUUUCUAAGUUCGCCGAGAAGGAUAACAUCGUCUUGGGAGAAG

GGGGUAUUACAUUGUCGGGAGGGCAGCGAGCGCGGAUCAGCCUCGCGAGAGCGG

UAUACAAAGAUGCAGAUUUGUAUCUGCUUGAUUCACCGUUUGGAUACCUCGACG

UAUUGACAGAAAAAGAAAUCUUCGAGUCGUGCGUGUGUAAACUUAUGGCUAAUA

AGACGAGAAUCCUGGUGACAUCAAAAAUGGAACACCUUAAGAAGGCGGACAAGA

UCCUGAUCCUCCACGAAGGAUCGUCCUACUUUUACGGCACUUUCUCAGAGUUGCA

AAACUUGCAGCCGGACUUCUCAAGCAAACUCAUGGGGUGUGACUCAUUCGACCAG

UUCAGCGCGGAACGGCGGAACUCGAUCUUGACGGAAACGCUGCACCGAUUCUCGC

UUGAGGGUGAUGCCCCGGUAUCGUGGACCGAGACAAAGAAGCAGUCGUUUAAGC

AGACAGGAGAAUUUGGUGAGAAAAGAAAGAACAGUAUCUUGAAUCCUAUUAACU

CAAUUCGCAAGUUCUCAAUCGUCCAGAAAACUCCACUGCAGAUGAAUGGAAUUG

AAGAGGAUUCGGACGAACCCCUGGAGCGCAGGCUUAGCCUCGUGCCGGAUUCAGA

GCAAGGGGAGGCCAUUCUUCCCCGGAUUUCGGUGAUUUCAACCGGACCUACACUU

CAGGCGAGGCGAAGGCAAUCCGUGCUCAACCUCAUGACGCAUUCGGUAAACCAGG

GGCAAAACAUUCACCGCAAAACGACGGCCUCAACGAGAAAAGUGUCACUUGCACC

CCAGGCGAAUUUGACUGAACUCGACAUCUACAGCCGUAGGCUUUCGCAAGAAACC

GGACUUGAGAUCAGCGAAGAAAUCAAUGAAGAAGAUUUGAAAGAGUGUUUCUUU

GAUGACAUGGAAUCAAUCCCAGCGGUGACAACGUGGAACACAUACUUGCGUUAC

AUCACGGUGCACAAGUCCUUGAUUUUCGUCCUCAUCUGGUGUCUCGUGAUCUUUC

UCGCUGAGGUCGCAGCGUCACUUGUGGUCCUCUGGCUGCUUGGUAAUACGCCCUU

GCAAGACAAAGGCAAUUCUACACACUCAAGAAACAAUUCCUAUGCCGUGAUUAUC

ACUUCUACAAGCUCGUAUUACGUGUUUUACAUCUACGUAGGAGUGGCCGACACUC

UGCUCGCGAUGGGUUUCUUCCGAGGACUCCCACUCGUUCACACGCUUAUCACUGU

CUCCAAGAUUCUCCACCAUAAGAUGCUUCAUAGCGUACUGCAGGCUCCCAUGUCC

ACCUUGAAUACGCUCAAGGCGGGAGGUAUUUUGAAUCGCUUCUCAAAAGAUAUU

GCAAUUUUGGAUGACCUUCUGCCCCUGACGAUCUUCGACUUCAUCCAGUUGUUGC

UGAUCGUGAUUGGGGCUAUUGCAGUAGUCGCUGUCCUCCAGCCUUACAUUUUUG

UCGCGACCGUUCCGGUGAUCGUGGCGUUUAUCAUGCUGCGGGCCUAUUUCUUGCA

GACGUCACAGCAGCUUAAGCAACUGGAGUCUGAAGGGAGGUCGCCUAUCUUUAC

GCAUCUUGUGACCAGUUUGAAGGGAUUGUGGACGUUGCGCGCCUUUGGCAGGCA

GCCCUACUUUGAAACACUGUUCCACAAAGCGCUGAAUCUCCAUACGGCAAAUUGG

UUUUUGUAUUUGAGUACCCUCCGAUGGUUUCAGAUGCGCAUUGAGAUGAUUUUU

GUGAUCUUCUUUAUCGCGGUGACUUUUAUCUCCAUCUUGACCACGGGAGAGGGC

GAGGGACGGGUCGGUAUUAUCCUGACACUCGCCAUGAACAUUAUGAGCACUUUG

CAGUGGGCAGUGAACAGCUCGAUUGAUGUGGAUAGCCUGAUGAGGUCCGUUUCG

AGGGUCUUUAAGUUCAUCGACAUGCCGACGGAGGGAAAGCCCACAAAAAGUACG

AAACCCUAUAAGAAUGGGCAAUUGAGUAAGGUAAUGAUCAUCGAGAACAGUCAC

GUGAAGAAGGAUGACAUCUGGCCUAGCGGGGGUCAGAUGACCGUGAAGGACCUG

ACGGCAAAAUACACCGAGGGAGGGAACGCAAUCCUUGAAAACAUCUCGUUCAGCA

UUAGCCCCGGUCAGCGUGUGGGGUUGCUCGGGAGGACCGGGUCAGGAAAAUCGA
```

-continued

CGUUGCUGUCGGCCUUCUUGAGACUUCUGAAUACAGAGGGUGAGAUCCAGAUCG

ACGGCGUUUCGUGGGAUAGCAUCACCUUGCAGCAGUGGCGGAAAGCGUUUGGAG

UAAUCCCCAAAAGGUCUUUAUCUUUAGCGGAACCUUCCGAAAGAAUCUCGAUCC

UUAUGAACAGUGGUCAGAUCAAGAGAUUUGGAAAGUCGCGGACGAGGUUGGCCU

UCGGAGUGUAAUCGAGCAGUUUCCGGGAAAACUCGACUUUGUCCUUGUAGAUGG

GGGAUGCGUCCUGUCGCAUGGGCACAAGCAGCUCAUGUGCCUGGCGCGAUCCGUC

CUCUCUAAAGCGAAAAUUCUUCUCUUGGAUGAACCUUCGGCCCAUCUGGACCCGG

UAACGUAUCAGAUCAUCAGAAGGACACUUAAGCAGGCGUUUGCCGACUGCACGG

UGAUUCUCUGUGAGCAUCGUAUCGAGGCCAUGCUCGAAUGCCAGCAAUUUCUUG

UCAUCGAAGAGAAUAAGGUCCGCCAGUACGACUCCAUCCAGAAGCUGCUUAAUGA

GAGAUCAUUGUUCCGGCAGGCGAUUUCACCAUCCGAUAGGGUGAAACUUUUUCC

ACACAGAAAUUCGUCGAAGUGCAAGUCCAAACCGCAGAUCGCGGCCUUGAAAGAA

GAGACUGAAGAAGAAGUUCAAGACACGCGUCUUUAA

Exemplary Codon-Optimized Firefly Luciferase (FFL) mRNA
Construct design:
$X_1$-SEQ ID NO: 2-$Y_1$

[SEQ ID NO: 2]

AUGGAAGAUGCCAAAAACAUUAAGAAGGGCCCAGCGCCAUUCUACCCACUCGAAG

ACGGGACCGCCGGCGAGCAGCUGCACAAAGCCAUGAAGCGCUACGCCCUGGUGCC

CGGCACCAUCGCCUUUACCGACGCACAUAUCGAGGUGGACAUUACCUACGCCGAG

UACUUCGAGAUGAGCGUUCGGCUGGCAGAAGCUAUGAAGCGCUAUGGGCUGAAU

ACAAACCAUCGGAUCGUGGUGUGCAGCGAGAAUAGCUUGCAGUUCUUCAUGCCCG

UGUUGGGUGCCCUGUUCAUCGGUGUGGCUGUGGCCCCAGCUAACGACAUCUACAA

CGAGCGCGAGCUGCUGAACAGCAUGGGCAUCAGCCAGCCCACCGUCGUAUUCGUG

AGCAAGAAGGGCUGCAAAAGAUCCUCAACGUGCAAAAGAAGCUACCGAUCAUA

CAAAAGAUCAUCAUCAUGGAUAGCAAGACCGACUACCAGGGCUUCCAAAGCAUGU

ACACCUUCGUGACUUCCCAUUUGCCACCCGGCUUCAACGAGUACGACUUCGUGCC

CGAGAGCUUCGACCGGGACAAAACCAUCGCCCUGAUCAUGAACAGUAGUGGCAGU

ACCGGAUUGCCCAAGGGCGUAGCCCUACCGCACCGCACCGCUUGUGUCCGAUUCA

GUCAUGCCCGCGACCCCAUCUUCGGCAACCAGAUCAUCCCCGACACCGCUAUCCU

CAGCGUGGUGCCAUUUCACCACGGCUUCGGCAUGUUCACCACGCUGGGCUACUUG

AUCUGCGGCUUUCGGGUCGUGCUCAUGUACCGCUUCGAGGAGGAGCUAUUCUUGC

GCAGCUUGCAAGACUAUAAGAUUCAAUCUGCCCUGCUGGUGCCCACACUAUUUAG

CUUCUUCGCUAAGAGCACUCUCAUCGACAAGUACGACCUAAGCAACUUGCACGAG

AUCGCCAGCGGCGGGGCGCCGCUCAGCAAGGAGGUAGGUGAGGCCGUGGCCAAAC

GCUUCCACCUACCAGGCAUCCGCCAGGGCUACGGCCUGACAGAAACAACCAGCGC

CAUUCUGAUCACCCCCGAAGGGGACGACAAGCCUGGCGCAGUAGGCAAGGUGGUG

CCCUUCUUCGAGGCUAAGGUGGUGGACUUGGACACCGGUAAGACACUGGGUGUG

AACCAGCGCGGCGAGCUGUGCGUCCGUGGCCCCAUGAUCAUGAGCGGCUACGUUA

ACAACCCCGAGGCUACAAACGCUCUCAUCGACAAGGACGGCUGGCUGCACAGCGG

CGACAUCGCCUACUGGGACGAGGACGAGCACUUCUUCAUCGUGGACCGGCUGAAG

AGCCUGAUCAAAUACAAGGGCUACCAGGUAGCCCCAGCCGAACUGGAGAGCAUCC

UGCUGCAACACCCCAACAUCUUCGACGCCGGGGUCGCCGGCCUGCCCGACGACGA

UGCCGGCGAGCUGCCCGCCGCAGUCGUCGUGCUGGAACACGGUAAAACCAUGACC

GAGAAGGAGAUCGUGGACUAUGUGGCCAGCCAGGUUACAACCGCCAAGAAGCUG

CGCGGUGGUGUUGUGUUCGUGGACGAGGUGCCUAAAGGACUGACCGGCAAGUUG

GACGCCCGCAAGAUCCGCGAGAUUCUCAUUAAGGCCAAGAAGGGCGGCAAGAUCG

CCGUGUAA

Exemplary Codon-Optimized Human Argininosuccinate Synthetase (ASS1) mRNA Construct design:
X₁-SEQ ID NO: 3-Y₂

[SEQ ID NO: 3]

AUGAGCAGCAAGGGCAGCGUGGUGCUGGCCUACAGCGGCGGCCUGGACACCAGCU

GCAUCCUGGUGUGGCUGAAGGAGCAGGGCUACGACGUGAUCGCCUACCUGGCCAA

CAUCGGCCAGAAGGAGGACUUCGAGGAGGCCCGCAAGAAGGCCCUGAAGCUGGGC

GCCAAGAAGGUGUUCAUCGAGGACGUGAGCCGCGAGUUCGUGGAGGAGUUCAUC

UGGCCCGCCAUCCAGAGCAGCGCCCUGUACGAGGACCGCUACCUGCUGGGCACCA

GCCUGGCCCGCCCCUGCAUCGCCCGCAAGCAGGUGGAGAUCGCCCAGCGCGAGGG

CGCCAAGUACGUGAGCCACGGCGCCACCGGCAAGGGCAACGACCAGGUGCGCUUC

GAGCUGAGCUGCUACAGCCUGGCCCCCCAGAUCAAGGUGAUCGCCCCCUGGCGCA

UGCCCGAGUUCUACAACCGCUUCAAGGGCCGCAACGACCUGAUGGAGUACGCCAA

GCAGCACGGCAUCCCCAUCCCCGUGACCCCCAAGAACCCCUGGAGCAUGGACGAG

AACCUGAUGCACAUCAGCUACGAGGCCGGCAUCCUGGAGAACCCCAAGAACCAGG

CCCCCCCCGGCCUGUACACCAAGACCCAGGACCCCGCCAAGGCCCCCAACACCCCC

GACAUCCUGGAGAUCGAGUUCAAGAAGGGCGUGCCCGUGAAGGUGACCAACGUG

AAGGACGGCACCACCCACCAGACCAGCCUGGAGCUGUUCAUGUACCUGAACGAGG

UGGCCGGCAAGCACGGCGUGGGCCGCAUCGACAUCGUGGAGAACCGCUUCAUCGG

CAUGAAGAGCCGCGGCAUCUACGAGACCCCCGCCGGCACCAUCCUGUACCACGCC

CACCUGGACAUCGAGGCCUUCACCAUGGACCGCGAGGUGCGCAAGAUCAAGCAGG

GCCUGGGCCUGAAGUUCGCCGAGCUGGUGUACACCGGCUUCUGGCACAGCCCCGA

GUGCGAGUUCGUGCGCCACUGCAUCGCCAAGAGCCAGGAGCGCGUGGAGGGCAAG

GUGCAGGUGAGCGUGCUGAAGGGCCAGGUGUACAUCCUGGGCCGCGAGAGCCCCC

UGAGCCUGUACAACGAGGAGCUGGUGAGCAUGAACGUGCAGGGCGACUACGAGC

CCACCGACGCCACCGGCUUCAUCAACAUCAACAGCCUGCGCCUGAAGGAGUACCA

CCGCCUGCAGAGCAAGGUGACCGCCAAGUGA

5' and 3' UTR Sequences
X₁ =

[SEQ ID NO: 4]

GGACAGAUCGCCUGGAGACGCCAUCCACGCUGUUUUGACCUCCAUAGAAGACACC

GGGACCGAUCCAGCCUCCGCGGCCGGGAACGGUGCAUUGGAACGCGGAUUCCCCG

UGCCAAGAGUGACUCACCGUCCUUGACACG

Y₁ =

[SEQ ID NO: 5]

CGGGUGGCAUCCCUGUGACCCCUCCCCAGUGCCUCUCCUGGCCCUGGAAGUUGCC

ACUCCAGUGCCCACCAGCCUUGUCCUAAUAAAAUUAAGUUGCAUCAAGCU

Y₂ =

[SEQ ID NO: 6]

GGGUGGCAUCCCUGUGACCCCUCCCCAGUGCCUCUCCUGGCCCUGGAAGUUGCCA

CUCCAGUGCCCACCAGCCUUGUCCUAAUAAAAUUAAGUUGCAUCAAAGCU

Synthesis of mRNA

In each of the examples below, the synthesis of mRNA was conducted under complete RNAse-free conditions. All tubes, vials, pipette tips, pipettes, buffers, etc. were required to be nuclease-free, unless explicitly stated otherwise.

In the following examples, unless otherwise described, mRNA was synthesized via in vitro transcription from a linearized DNA template. To produce the desired mRNA pre-cursor (IVT) construct, a mixture of ~8 mg of linearized DNA, rNTPs (7.25 mM), DTT (10 mM), T7 RNA polymerase, RNAse Inhibitor, Pyrophosphatase and reaction buffer (10×, 800 mM Hepes (pH 8.0), 20 mM Spermidine, 250 mM MgCfr, pH 7.7) was prepared with RNase-free water to a final volume of 180 mL. The reaction mixture is incubated at 37° C. for a range of time between 20 minutes-60 minutes. Upon completion, the mixture is treated with DNase I for an additional 15 minutes and quenched accordingly.

Addition of 5' Cap and 3' Tail

The purified mRNA product from the aforementioned IVT step (and possibly initial TFF filtration as well) was denatured at 65° C. for 10 minutes. Separately, portions of GTP (1.0 mM), S-adenosyl methionine, RNAse inhibitor, 2'-O-Methyltransferase and guanylyl transferase are mixed together with reaction buffer (10×, 500 mM Tris-HCl (pH 8.0), 60 mM KCl, 12.5 mM MgCl2) to a final concentration of 1.6 L. Upon denaturation, the mRNA was cooled on ice and then added to the reaction mixture. The combined solution was incubated for a range of time at 37° C. for 25-90 minutes. Upon completion, aliquots of ATP (2.0 mM), PolyA Polymerase and tailing reaction buffer (10×, 500 mM Tris-HCl (pH 8.0), 2.5 M NaCl, 100 mM MgCl2) were added and the total reaction mixture was further incubated at 37° C. for a range of time from 20-45 minutes. Upon completion, the final reaction mixture was quenched and purified accordingly.

Purification of mRNA

Precipitation of mRNA

Messenger RNA can be precipitated using a variety of methods. For example, the use of lithium chloride, potassium chloride, guanidinium chloride, guanidinium thiocyanate, guanidinium isothiocyanate, ammonium acetate and other salts afford efficient precipitation of mRNA from the reaction mixture.

Tangential Flow Filtration

In the following examples, unless otherwise described, the tangential flow filtration (TFF) system consisted of a filtration membrane and a peristaltic pump (Spectrum system) with tangential circulation of the fluid across the membrane at a feed rate of ~130 mL/min with a 30 mL/min flow rate for the permeate. The TFF membrane employed was a MidiKros 500 kDa mPES 115 cm$^2$ (Spectrum Labs). Before use, the filter cartridge was washed with nuclease free water and further cleaned with 0.2 N NaOH. Finally the system was cleaned with nuclease free water until the pH of permeate and retentate reached a pH ~6. Isolation of mRNA via TFF can be accomplished as depicted in FIG. 1.

Purification of Firefly Luciferase mRNA

In a representative example of mRNA purification, a 1 gram batch of firefly luciferase (FFL) mRNA was transcribed via in vitro methods to produce the aforementioned intermediate construct with no cap and no polyA tail. This reaction maintained a total volume of ~180 mL and was quenched upon completion by the addition of DNAse I (~9.0 KU). The resulting solution was treated with a homogeneous solution of 4 M guanidinium thiocyanate, 0.5% sodium lauryl sarcosyl, and 25 mM sodium citrate (1500 mL), bringing the total volume to 1.68 L. The resultant mixture was kept at ambient temperature for ~5 minutes followed by further treatment of 1.1 L of absolute ethanol. The mRNA slowly precipitated and the suspension was kept at ambient temperature for ~5 minutes. Upon completion, the entire heterogeneous suspension was pumped through a filtration membrane using tangential flow filtration (TFF).

In this example, modified polyethersulfone (mPES) hollow fiber membranes were employed with a surface area of 2600 cm$^2$. The resulting heterogenous mixture (post-precipitation) was pumped through the filter system at a flow rate of 750 mL/min for approximately 8 min in portions. Upon completion, the resulting captured precipitate was rinsed with the guanidinium buffer/ethanol combined buffer solution followed by 80% ethanol (500 mL, 750 mL/min) and repeated multiple times (>5×). Once completely washed, the solid mRNA distributed across the membrane was treated with RNAse-free water (250 mL) and re-circulated over 5-10 minutes to ensure dissolution. This process was repeated until there was no more mRNA recovered. Upon completion, the resulting mRNA solution was further dialyzed with 1 mM sodium citrate (pH 6.4) using a 100 KDa MWCO membrane to remove any residual ethanol and obtained a final mRNA product in the proper storage solution. Final concentration was determined via absorption at 260 nm ($\lambda_{max}$). Messenger RNA purity was determined via UV absorption (260/280 ratio) as well as protein gels (silver stain, SYPRO stain, coomassie, etc). Messenger RNA integrity was determined via gel electrophoresis as well as in vitro/in vivo analysis of protein production.

Purification of ASS1 mRNA

In a second representative example of mRNA purification, a 1 gram batch of ASS1 mRNA was transcribed via in vitro methods to produce the aforementioned intermediate construct with no cap and no polyA tail. This reaction maintained a total volume of ~180 mL and was quenched upon completion by the addition of DNAse I (~9.0 KU). The resulting solution was treated with a homogeneous solution of 4 M guanidinium thiocyanate, 0.5% sodium lauryl sarcosyl, and 25 mM sodium citrate (1500 mL), bringing the total volume to 1.68 L. The resultant mixture was kept at ambient temperature for ~5 minutes followed by further treatment of 1.1 L of absolute ethanol. The messenger RNA slowly precipitated and the suspension was kept at ambient temperature for ~5 minutes. Upon completion, the entire heterogeneous suspension was pumped through a filtration membrane using tangential flow filtration (TFF) and isolated as described above.

Purification of CFTR mRNA

In a third representative example of mRNA purification, a 1.5 gram batch of modified CFTR mRNA being transcribed via in vitro methods to produce the aforementioned intermediate construct with no cap and no polyA tail. This reaction maintains a total volume of ~270 mL and is quenched upon completion by the addition of DNAse I (~13.5 KU). The resulting solution was treated with a homogeneous solution of 4 M guanidinium thiocyanate, 0.5% sodium lauryl sarcosyl, and 25 mM sodium citrate (1500 mL), bringing the total volume to 1.77 L. The resultant mixture was kept at ambient temperature for ~5 minutes followed by further treatment of 1.1 L of absolute ethanol. The mRNA slowly precipitated and the suspension was kept at ambient temperature for ~5 minutes. Upon completion, the entire heterogeneous suspension was pumped through a filtration membrane using tangential flow filtration (TFF) and isolated as described above.

Example 2. Analysis of Purified mRNA

Testing for Presence of Enzymes in Purified mRNA
SYPRO Stain Gels

Standard SYPRO-stained protein gels were performed to determine the presence of any residual reagent enzymes present before and after purifications. Gels were run at 200V for 35 minutes.
Silver Stain Gels Silver stains of all mRNA batches and fractions were performed using SilverQuest® (Life Technologies, Catalog #LC6070) using the manufacturer's protocol. Briefly, samples were loaded (with and without treatment of RNAse) and monitored as compared to loaded enzyme control lanes. Gels were run at 200 V for 35 minutes. Exposure time was allotted for 8 minutes.
Assessment of mRNA Integrity Via Agarose Gel Electrophoresis Assays Unless otherwise described, mRNA size and integrity were assessed via gel electrophoresis. Either self-poured 1.0% agarose gel or Invitrogen E-Gel precast 1.2% agarose gels were employed. Messenger RNA was loaded at 1.0-1.5 µg quantities per well. Upon completion, mRNA bands were visualized using ethidium bromide.
In Vitro mRNA Integrity Assays Unless otherwise described, in vitro transfections of firefly luciferase (FFL), argininosuccinate synthetase (ASS1) mRNA, and CFTR mRNA were performed using HEK293T cells. Transfections of one microgram of each mRNA construct were performed in separate wells using lipofectamine. Cells were harvested at select time points (e.g. 4 hour, 8 hour, etc.) and respective protein production was analyzed. For FFL mRNA, cell lysates were analyzed for luciferase production via bioluminescence assays. For ASS1 mRNA, cell lysates were analyzed for ASS1 production via ELISA assays. For CFTR mRNA, cell lysates were analyzed for CFTR production via western blot procedures
Luciferase Assay The bioluminescence assay was conducted using a Promega Luciferase Assay System (Item #E1500). The Luciferase Assay Reagent was prepared by adding 10 mL of Luciferase Assay Buffer to Luciferase Assay Substrate and mix via vortex. 20 µL of homogenate samples were loaded onto a 96-well plate, followed by 20 µL of plate control to each sample. Separately, 120 µL of Luciferase Assay Reagent (prepared as described above) was loaded into each well of a 96-well flat bottomed plate. Each plate was inserted into the appropriate chambers using a Molecular Device Flex Station instrument and the luminescence was measured in relative light units (RLU).
ASS1 ELISA Assay Standard ELISA procedures were followed employing mouse anti-ASS1 2D1-2E12 IgG as the capture antibody with rabbit anti-ASS1 #3285 IgG as the secondary (detection) antibody (Shire Human Genetic Therapies). Horseradish peroxidase (HRP)-conjugated goat anti-rabbit IgG was used for activation of the 3,3',5,5'-tetramethylbenzidine (TMB) substrate solution. The reaction was quenched using 2N $H_2SO_4$ after 20 minutes. Detection was monitored via absorption (450 nm) on a Molecular Device SpectraMax instrument. Untreated mouse serum and organs and human ASS1 protein were used as negative and positive controls, respectively.

CFTR Western Blot Analysis

Western blots were performed on protein samples obtained using immunoprecipitation methods (Dynabeads G). In general, cells or tissue homogenates were processed and treated with Dynabead G pre-bound to anti-human CFTR antibody (R&D Systems, MAB25031). Detection of human CFTR protein was accomplished using Ab570.

Example 3. Purification Results

This example demonstrates that firefly luciferase (FFL) mRNA, argininosuccinate synthetase (ASS1) mRNA and cystic fibrosis transmembrane conductance regulator (CFTR) mRNA have been successfully purified using precipitation followed by tangential flow filtration with removal of enzymatic reagents as well as shortmers. Many typical chaotropic conditions were successfully employed to precipitate the mRNA as listed above.

Figure 2:
FIG. 2 shows an exemplary silver-stained protein gel of modified cystic fibrosis transmembrane conductance regulator (CFTR) mRNA from an initial 1 gram in vitro transcription (IVT) reaction according to provided methods (with three elutions) and control enzymes present in the IVT reaction.
Figure 3:
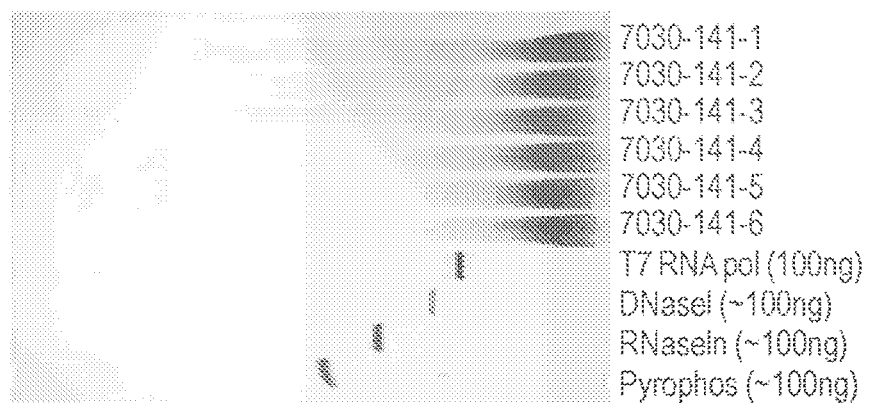
FIG. 3 shows an exemplary silver-stained protein gel of modified CFTR mRNA from an initial 1.5 gram in vitro transcription (IVT) reaction according to provided methods (with six elutions) and control enzymes present in the IVT reaction.
Figure 4:
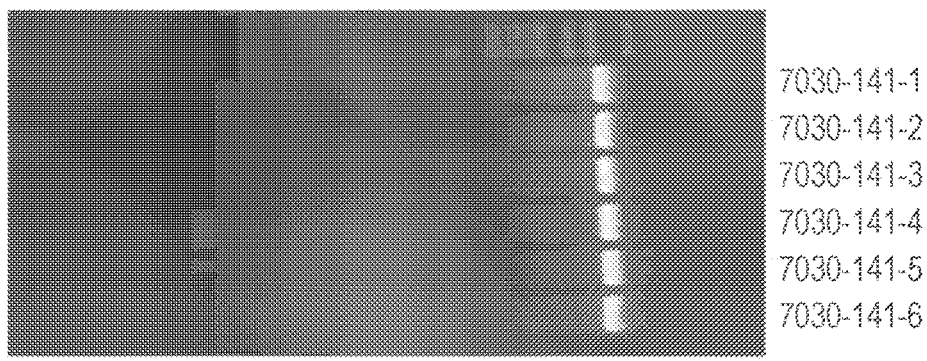
FIG. 4 shows the length of exemplary mRNA in in vitro transcription (IVT) samples of modified CFTR mRNA purified and filtered according to provided methods as shown by agarose gel electrophoresis. Full integrity remained for modified CFTR mRNA post large-scale precipitation.

To demonstrate this success, a large scale production (~1 gram) of modified CFTR mRNA IVT reaction mixture was subjected to 4 M guanidinium buffer solution (described above). The resulting mixture was then treated with absolute ethanol and incubated for five minutes at room temperature. Isolation of the precipitated mRNA was achieved via TFF as described above. FIG. 2 represents a silver stained protein gel that shows the resulting mRNA isolated after TFF employing the aforementioned conditions. There is no detectable enzyme present upon completion (T7 polymerase, DNAse I, pyrophosphatase, RNAse Inhibitor). Lanes 1-3 contained modified CFTR after elution 1 (E1), elution 2 (E2) and elution 3 (E3). Lanes 4-7 contained control enzymes present in the IVT reaction. FIG. 3 represents a silver stained protein gel that shows pure mRNA resulting from a larger scale (1.5 gram batch) precipitation and filtration process showing no residual enzyme. Lanes 1-6 contained mRNA after elutions 1-6. Lanes 7-10 contained control enzymes present in the IVT reaction (T7 polymerase, DNAse I, RNAse Inhibitor, and pyrophosphatase). FIG. 4 demonstrates that the modified CFTR mRNA is fully intact after such purification. It shows the results of agarose (1.0%) gel electrophoresis of modified CFTR mRNA after purification via precipitation and filtration. Lane 1 contained a RiboRuler HR ladder. Lane 2-7 contained modified CFTR mRNA purified via filtration after precipitation.

Figure 5:
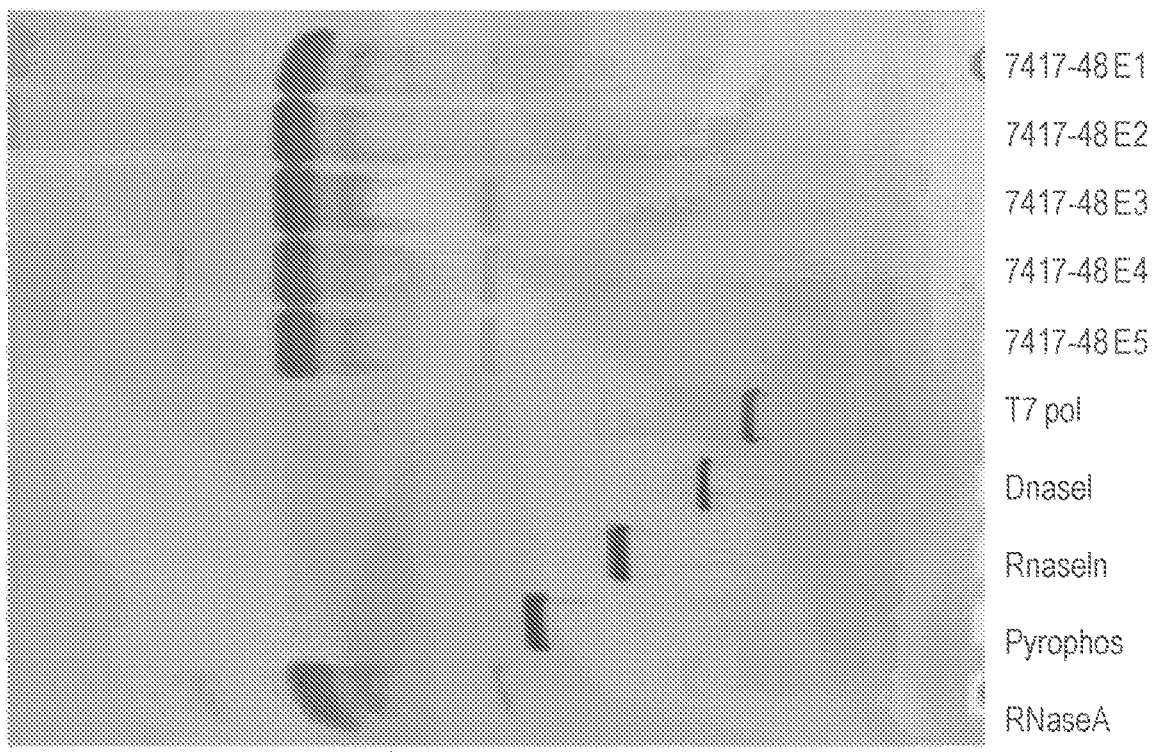
FIG. 5 shows an exemplary silver-stained protein gel of argininosuccinate synthetase (ASS1) mRNA from an initial 1 gram in vitro transcription (IVT) reaction according to provided methods (with five elutions) and control enzymes present in the IVT reaction.
Figure 6:
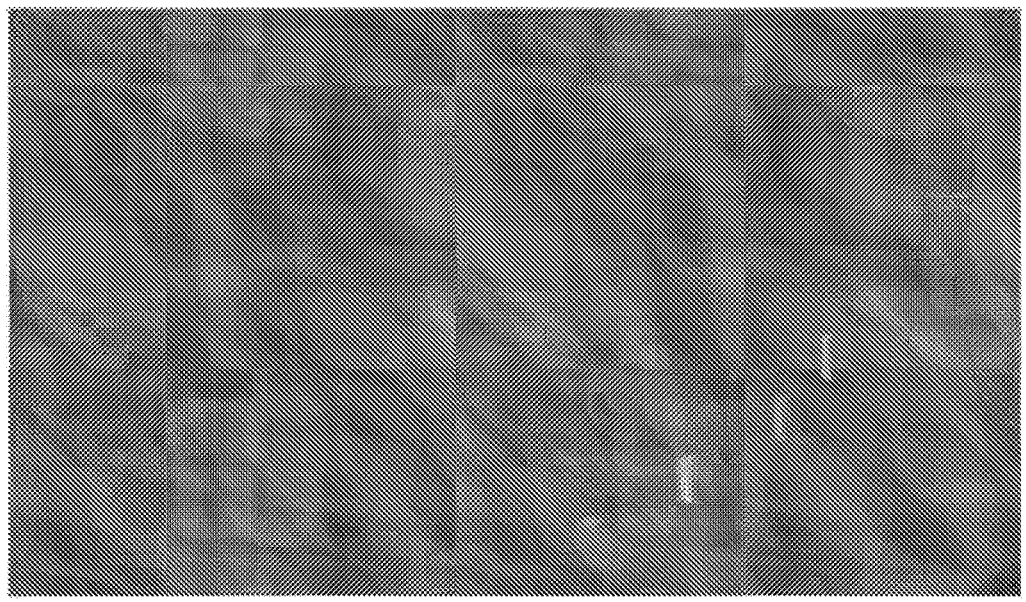
FIG. 6 shows an exemplary SYPRO-stained protein gel of argininosuccinate synthetase (ASS1) mRNA from an initial 1 gram in vitro transcription (IVT) reaction according to provided methods (with five elutions) and control enzymes present in the IVT reaction.
Figure 7:
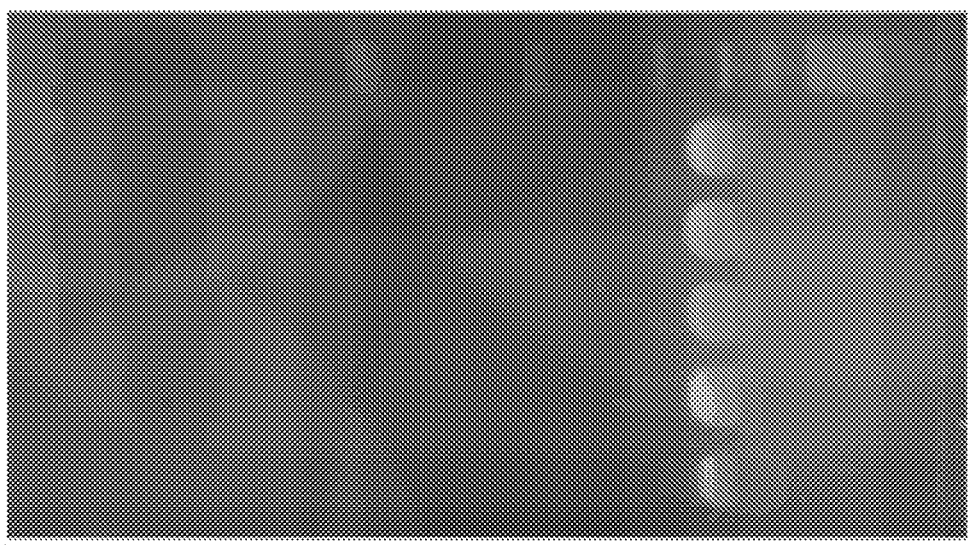
FIG. 7 shows the length of exemplary mRNA in in vitro transcription (IVT) samples of ASS1 mRNA purified and filtered according to provided methods as shown by agarose gel electrophoresis. Full integrity remained for ASS1 mRNA post large-scale precipitation.

This process is widely applicable to multiple different mRNA constructs. For example, a second mRNA construct was synthesized and purified using this method. In this instance, argininosuccinate synthetase (ASS1) mRNA was produced and precipitated using methods described above. The solid precipitate was loaded onto the TFF system and isolated according to the process described. FIG. 5 represents a silver-stain analysis of the resulting isolated ASS1 mRNA showing no residual enzyme present (T7 polymerase, DNAse I, RNAse inhibitor, pyrophosphatase). Lanes 1-5 contained mRNA after elutions 1-5. Lanes 6-9 contained control enzymes present in the IVT reaction. Lane 10 contained RNase A as a control because mRNA samples were pre-treated with RNAse A prior to loading. As demonstrated in FIG. 5, no enzymes were present after extensive exposure to silver stain development. This was further confirmed using SYPRO staining for residual enzymes as shown in FIG. 6. Using this method, one can again demonstrate the purity of the ASS1 mRNA as isolated using this process. Lanes 1-5 contained mRNA after elutions 1-5. Lanes 6-9 contained control enzymes present in the IVT reaction. In addition to this, RNA gel electrophoresis showed that the ASS1 mRNA integrity was maintained with full length ASS1 mRNA fully intact after this process (FIG. 7). In FIG. 7, Lane 1 contained a RiboRuler HR ladder and lanes 2-6 contained ASS1 mRNA after elutions 1-5.

Figure 8:
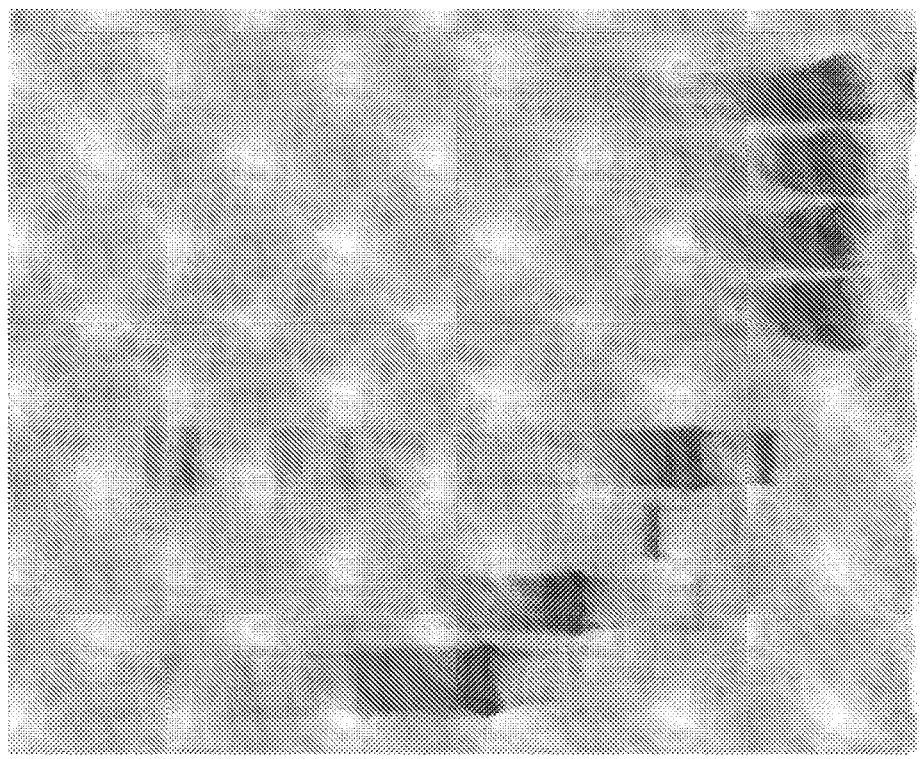
FIG. 8 shows an exemplary silver-stained protein gel of firefly luciferase (FFL) mRNA from an initial in vitro transcription (IVT) reaction according to provided methods (with either a single or double precipitation) and control enzymes present in the IVT reaction.
Figure 9:
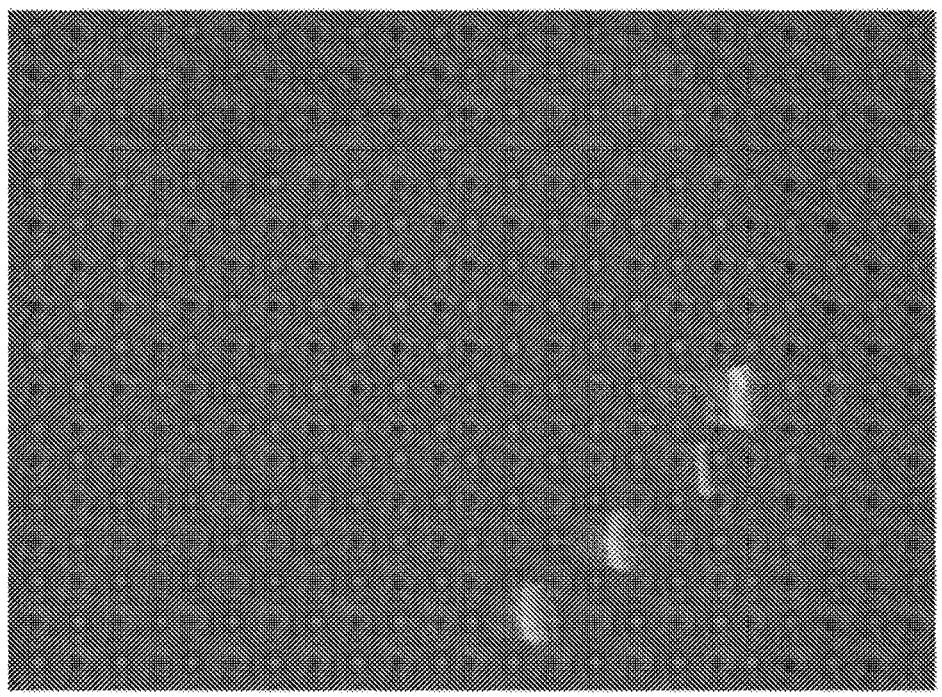
FIG. 9 shows an exemplary SYPRO-stained protein gel of firefly luciferase (FFL) mRNA from an initial in vitro transcription (IVT) reaction according to provided methods (with either a single or double precipitation) and control enzymes present in the IVT reaction.
Figure 10:
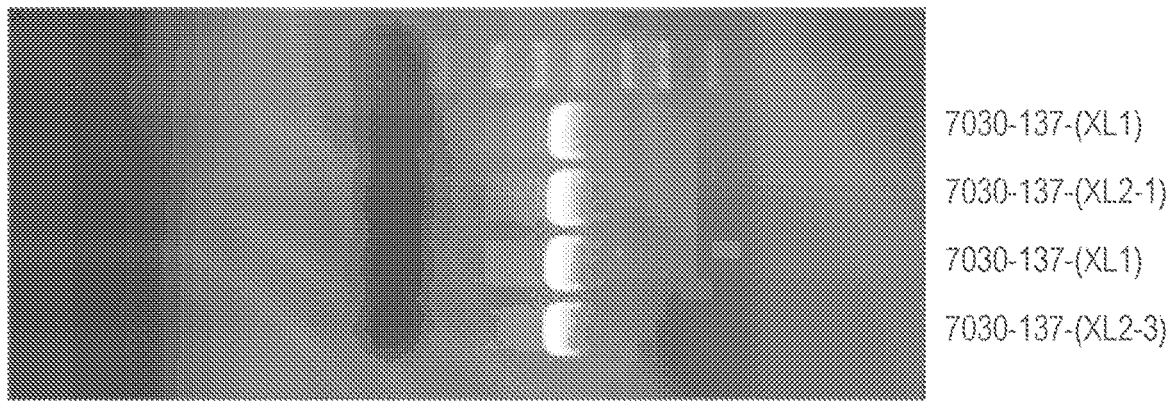
FIG. 10 shows the length of exemplary mRNA in in vitro transcription (IVT) samples of firefly luciferase (FFL) mRNA purified and filtered according to provided methods as shown by agarose gel electrophoresis. Full integrity remained for FFL mRNA post large-scale precipitation and re-precipitation.

To further demonstrate that this purification technique is widely applicable to multiple different mRNA constructs, FFL mRNA was synthesized and purified using this method. The mRNA was precipitated using 4 M guanidinium buffer system and filtered. FIG. 8 represents a silver-stain analysis of the resulting isolated FFL mRNA showing no residual enzyme present. Lanes 1-4 contained FFL mRNA purified via a single precipitation (XL1) or a double precipitation (XL2), with lanes 2-4 containing different elutions from the second precipitation recovery. Lanes 6-9 contained control enzymes present in the IVT reaction. As demonstrated in FIG. 8, no enzymes were present after extensive exposure to silver stain development. Further, one can see that a single precipitation appears to be sufficient in removing all of the unwanted residual enzyme. This was further confirmed using SYPRO staining for residual enzymes as shown in FIG. 9. Using this method, one can again demonstrate the purity of the FFL mRNA isolated using this process. In FIG. 9, lanes 1-4 contained FFL mRNA purified via a single precipitation (XL1) or a double precipitation (XL2), with lanes 2-4 containing different elutions from the second precipitation recovery. Lanes 6-9 contained control enzymes present in the IVT reaction. In addition to this, RNA gel electrophoresis showed that the FFL mRNA integrity was maintained with full length FFL mRNA fully intact after this process (FIG. 10). Further, the mRNA shows no difference after multiple re-precipitations. In FIG. 10, lane 1 contained a RiboRuler HR ladder and lanes 2-5 contained FFL mRNA purified via a single precipitation (XL1) or a double precipitation (XL2).

Figure 11:
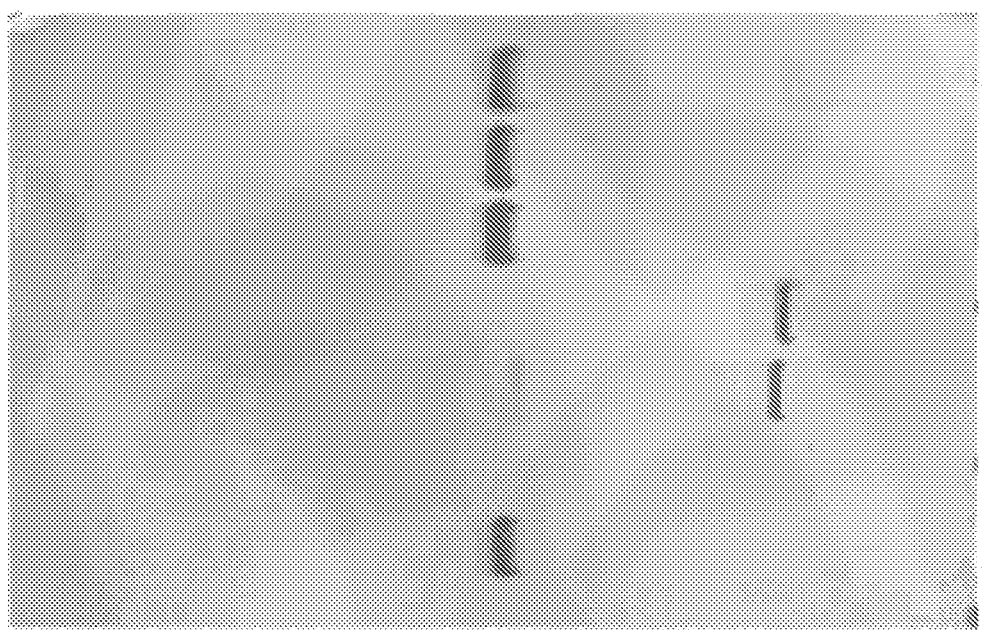
FIG. 11 shows an exemplary silver-stained protein gel of argininosuccinate synthetase (ASS1) mRNA from a final capping and tailing reaction (with three elutions) and control enzymes present in the capping and tailing reactions.
Figure 12:
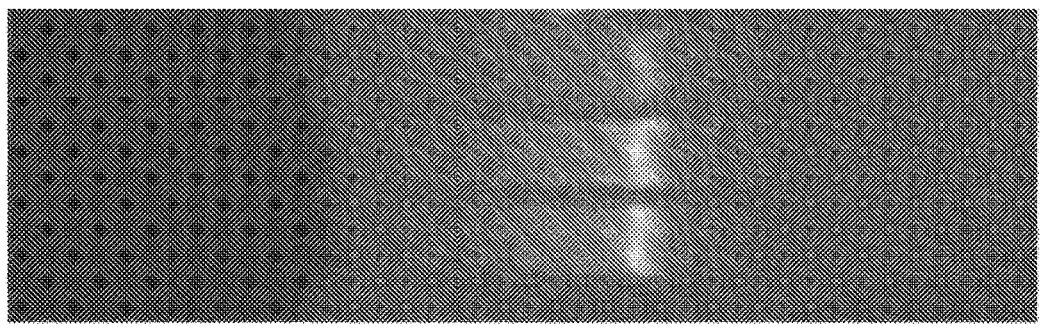
FIG. 12 shows the length of exemplary final ASS1 mRNA purified and filtered according to provided methods as shown by agarose gel electrophoresis. Full integrity remained for ASS1 mRNA post large-scale precipitation and re-precipitation.

Upon subjecting this isolated mRNA further to afford a capped and tailed final product, TFF methods were employed further to purify the final target mRNA. FIG. 11 demonstrates that precipitation, followed by capture and elution using tangential flow filtration, resulted in a successfully pure final mRNA product. In FIG. 11, lanes 1-3 contained ASS1 mRNA from a cap/tail reaction purified via a single precipitation (E1-3=elution 1-3). Lanes 4-6 contained key control enzymes present in both reaction steps. Lane 7 contained an RNase I control because mRNA samples were pre-treated with RNAse I prior to loading. In addition to this, RNA gel electrophoresis showed that the FFL mRNA integrity was maintained with full length FFL mRNA fully intact after this process (FIG. 12). In FIG. 12, lanes 1-3 contained capped and tailed ASS1 mRNA.

While such characterization affords information with respect to purity and mRNA size/integrity, a true measure of mRNA quality further lies within its ability to produce the desired protein. Therefore, a comparison of each of the isolated FFL mRNA constructs (TFF vs. spin-column) was made. Each of the three constructs listed below were transfected into HEK293T cells and the corresponding FFL protein production was assessed via FFL protein activity in the form of FFL luminescence upon exposure to luciferin (vida supra). Cells were harvested 24 hours post-transfection.

Figure 13:
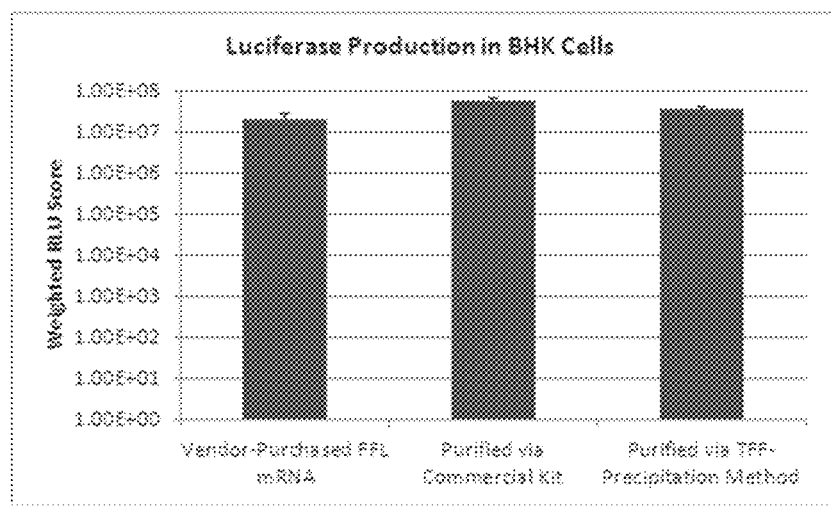
FIG. 13 shows exemplary luminescence observed within cell lysates of FFL mRNA treated HEK293T cells. Cells were harvested 24 hours post-transfection. A comparison of vendor derived mRNA versus spin-column purified mRNA (commercial kit) versus precipitation-TFF purified FFL mRNA translational ability is represented.

FFL Constructs:
1. FFL mRNA purchased from an outside vendor
2. FFL mRNA purified via commercial kit
3. FFL mRNA purified via precipitation-TFF method A comparison of luminescence output of FFL protein produced from each is represented in FIG. 13. The integrity of the TFF-purified FFL mRNA was maintained throughout the precipitation and tangential flow filtration process under the conditions described.

Figure 14:
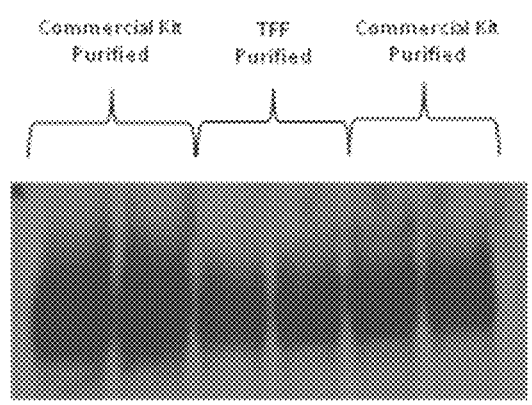
FIG. 14 shows exemplary CFTR protein levels observed within cell lysates of hCFTR mRNA-transfected HEK293T cells. Cells were harvested 24 hours post-transfection. A comparison of TFF purified mRNA versus spin-column (commercial kit) hCFTR mRNA translational ability is represented.

Further, successful detection of human CFTR protein was achieved from transfection of hCFTR mRNA isolated using the aforementioned process. FIG. 14 shows successful production of human CFTR protein after transfection of hCFTR mRNA purified via either commercial kits or the aforementioned TFF-based precipitation method. Visualization of this "C-band" for CFTR protein, which is indicative of a full length, properly trafficked CFTR protein, supports the full integrity and active nature of the isolated mRNA via such conditions. This process is further easily scalable. For example, a separate mRNA construct was synthesized and purified at the 5 gram scale using this method. In this instance, argininosuccinate synthetase (ASS1) mRNA was produced and precipitated using methods described above. The solid precipitate was loaded onto the TFF system and isolated according to the process described.

Figure 15:
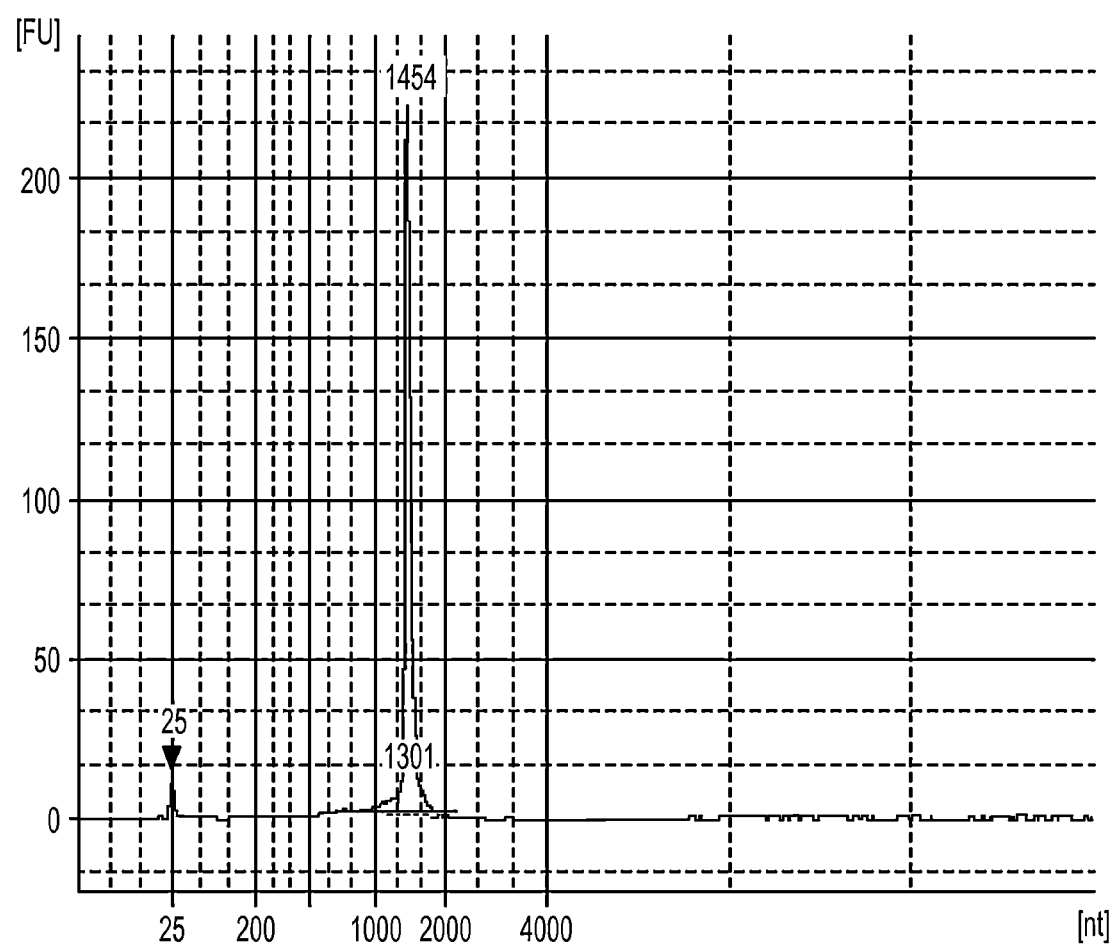
FIG. 15 shows the length of an exemplary mRNA from an in vitro transcription (IVT) sample of argininosuccinate synthetase (ASS1) mRNA purified and filtered according to provided methods. Full integrity remained for ASS1 mRNA post large-scale (5G) precipitation.
Figure 16:
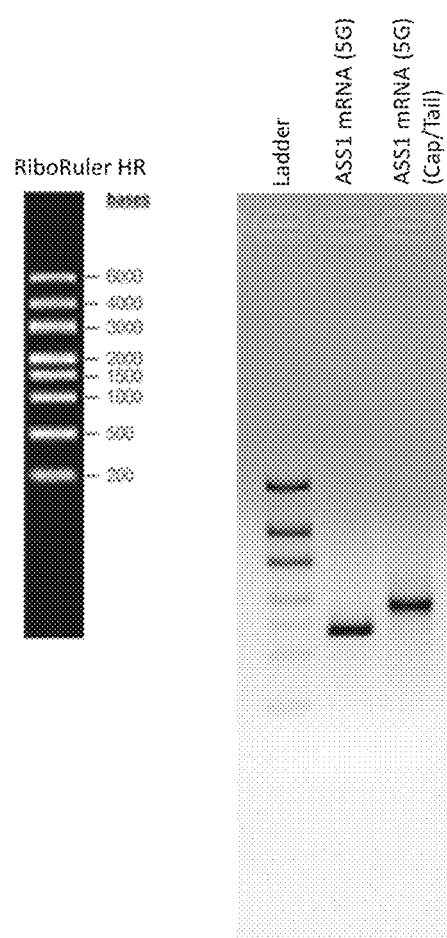
FIG. 16 shows the length of an exemplary mRNA from an in vitro transcription (IVT) sample of argininosuccinate synthetase (ASS1) mRNA (pre- and post-capped/tailed) purified and filtered according to provided methods. Full integrity remained for ASS1 mRNA post large-scale (5G) precipitation.

Integrity of the manufactured mRNA drug substance was demonstrated using two separate methods. FIG. 15 shows the length of an exemplary mRNA from an in vitro transcription (IVT) sample of argininosuccinate synthetase (ASS1) mRNA purified and filtered according to provided methods. mRNA length was demonstrated via agarose gel-on-a-chip electrophoresis. Intact and full length mRNA was confirmed using gel electrophoresis (FIG. 16) for both the IVT pre-cursor as well as the final capped and tailed construct. Full integrity remained for ASS1 mRNA post large-scale (5G) precipitation.

Figure 17:
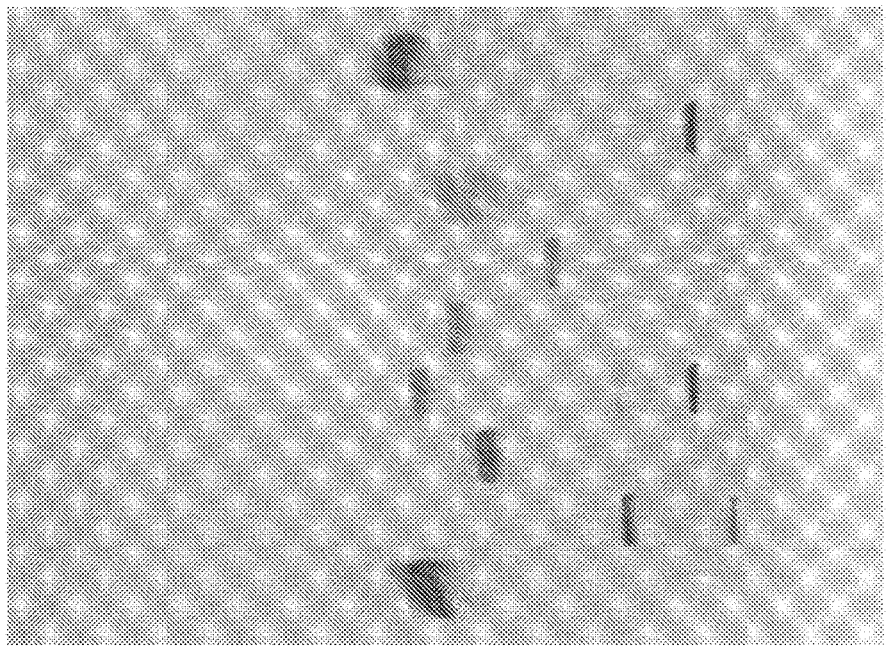
FIG. 17 shows an exemplary silver-stained protein gel of argininosuccinate synthetase (ASS1) mRNA after final purification (5G) according to provided methods as well as control enzymes present in the reaction.

As demonstrated previously, FIG. 17 shows that precipitation, followed by capture and elution using tangential flow filtration, resulted in a successfully pure final mRNA product. Lane 1 contained ASS1 mRNA from a cap/tail reaction purified via a single precipitation. Lanes 2-8 contained key control enzymes present in both reaction steps. Lane 9 contained an RNase I control because mRNA samples were pre-treated with RNAse I prior to loading. Such a silver stain method demonstrates that no residual enzymes are present.

Figure 18:
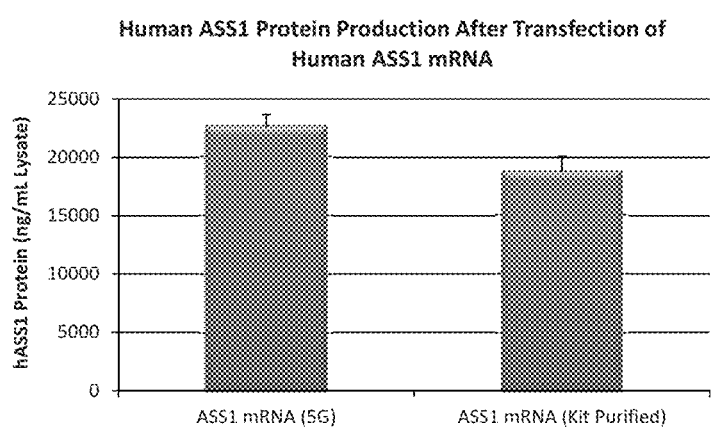
FIG. 18 shows exemplary human ASS1 protein production observed within cell lysates of ASS1 mRNA treated HEK293T cells. Cells were harvested 24 hours post-transfection. A comparison of spin-column purified mRNA (commercial kit) versus precipitation-TFF purified ASS1 mRNA (5G) translational ability is represented.

While such characterization affords information with respect to purity and mRNA size/integrity, a true measure of mRNA quality further lies within its ability to produce the desired protein. Therefore, a comparison of the isolated ASS1 mRNA constructs (TFF vs. spin-column) was made (FIG. 18). Each of the constructs listed below were transfected into HEK293T cells and the corresponding ASS1 protein production was assessed via ELISA methods. Cells were harvested ~18 hours post-transfection.

Figure 19:
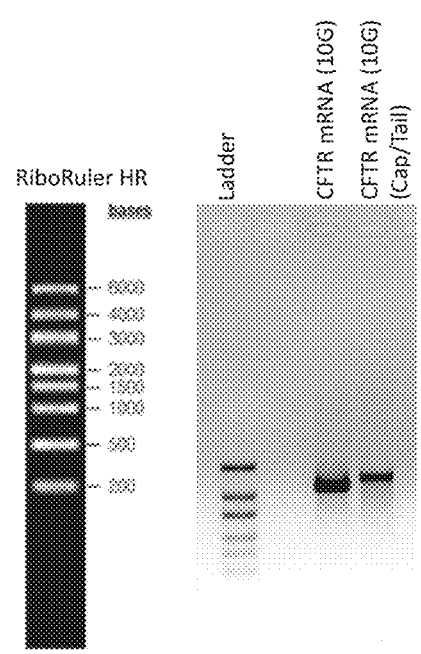
FIG. 19 shows the length of an exemplary mRNA in in vitro transcription (IVT) sample of cystic fibrosis transmembrane conductance regulator (CFTR) mRNA (pre- and post-capped/tailed) purified and filtered according to provided methods as shown by agarose gel electrophoresis. Full integrity remained for CFTR mRNA post large-scale (10G) precipitation.

A further demonstration of scalability was achieved with synthesis and purification of CFTR mRNA at the 10 gram scale using this method. In this instance, cystic fibrosis transmembrane conductance regulator (CFTR) mRNA was produced and precipitated using methods described above. The solid precipitate was loaded onto the TFF system and isolated according to the process described. Integrity of the manufactured mRNA drug substance was demonstrated using agarose gel electrophoresis. Intact and full length mRNA was confirmed (FIG. 19) for both the IVT pre-cursor as well as the final capped and tailed construct. Full integrity remained for CFTR mRNA post large-scale (10G) precipitation.

Figure 20:
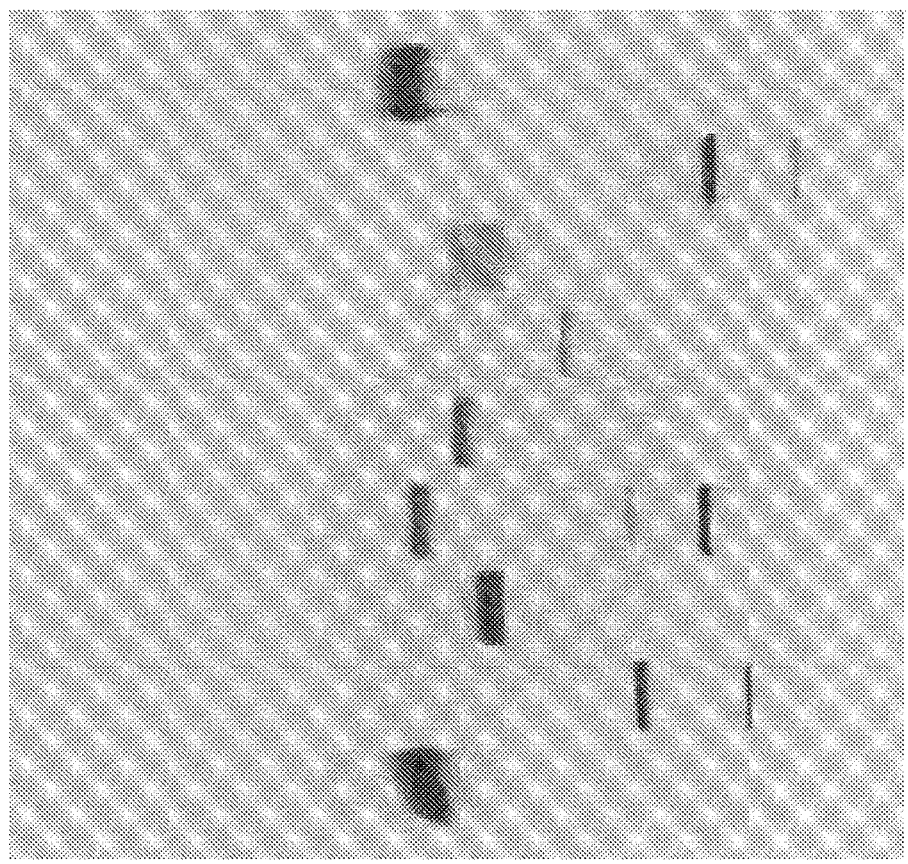
FIG. 20 shows an exemplary silver-stained protein gel of cystic fibrosis transmembrane conductance regulator (CFTR) mRNA after final purification (10G) according to provided methods as well as control enzymes present in the reaction.

Again, purity of the manufactured product at the 10 gram scale was demonstrated via silver stain as shown in FIG. 20. Lane 1 contains CFTR mRNA from a cap/tail reaction purified via a single precipitation. Lanes 2-8 contained key control enzymes present in both reaction steps. Lane 9 contained an RNase I control because mRNA samples were pre-treated with RNAse I prior to loading. Such a silver stain method demonstrates that no residual enzymes are present.

Figure 21:
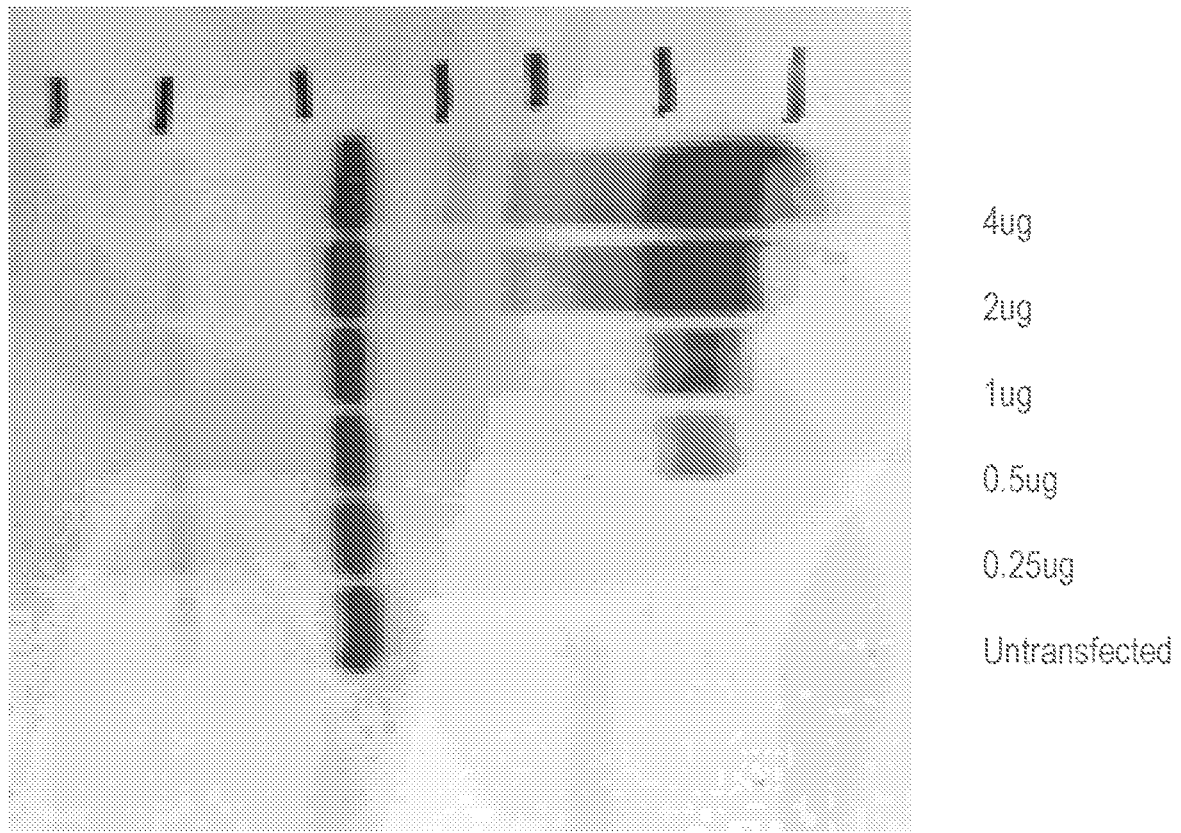
FIG. 21 shows exemplary CFTR protein levels observed within cell lysates of hCFTR mRNA-transfected HEK293T cells from a large scale production and purification. Cells were harvested 24 hours post-transfection.

As described above, such characterization affords information with respect to purity and mRNA size/integrity, however a true measure of mRNA quality further lies within its ability to produce the desired protein. Therefore, various amounts of CFTR mRNA were transfected into HEK293T cells and the corresponding CFTR protein production was assessed via western blot methods (FIG. 21). Cells were harvested ~18 hours post-transfection.

In another embodiment, further demonstration of scalability was achieved with synthesis and purification of ASS1 mRNA at the 25 gram scale using this method. In this instance, argininosuccinate synthetase (ASS1) mRNA was produced and precipitated using methods described above.

Figure 22:
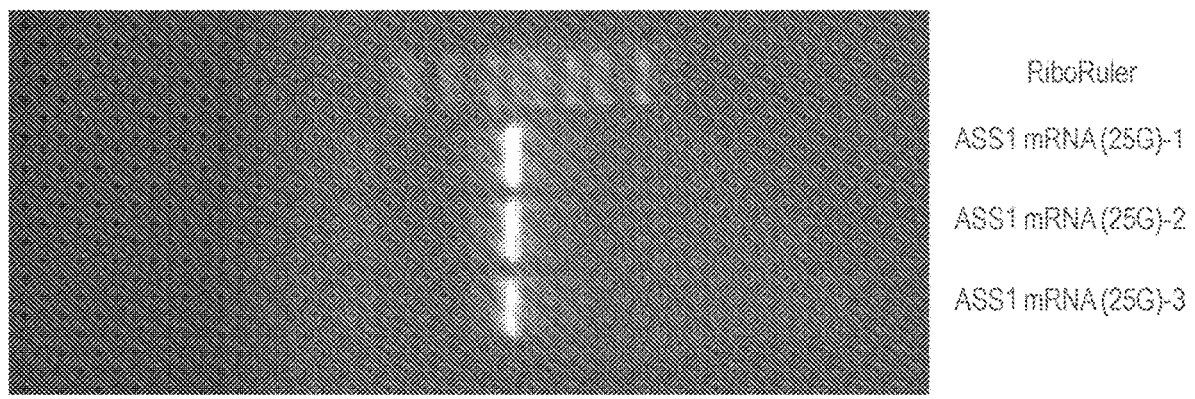
FIG. 22 shows the length of an exemplary mRNA in in vitro transcription (IVT) sample of argininosuccinate synthetase (ASS1) mRNA at 25G scale production. Full integrity remained for ASS1 mRNA post large-scale (25G) isolation.

The solid precipitate was loaded onto the TFF system and isolated according to the process described. Integrity of the manufactured mRNA drug substance was demonstrated using agarose gel electrophoresis. Intact and full length mRNA was confirmed (FIG. 22) for ASS1 mRNA post large-scale (25G) precipitation.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:

1. A method of purifying messenger RNA (mRNA), comprising
    (a) precipitating mRNA;
    (b) treating the precipitated mRNA to a membrane filtration process; and
    (c) eluting the precipitated mRNA from the membrane by re-solubilizing the mRNA;
    wherein the membrane filtration process is tangential flow filtration, and wherein the method further comprises a step of dialyzing the purified mRNA solution.

2. The method of claim 1, wherein the membrane used for the membrane filtration is selected from the group consisting of polyethersulfone (mPES) (not modified), polyethersulfone (mPES) hollow fiber membrane, polyvinylidene fluoride (PVDF), cellulose acetate, nitrocellulose, MCE (mixed cellulose esters), ultra-high MW polyethylene (UPE), polyfluorotetraethylene (PTFE), nylon, polysulfone, polyether sulfone, polyacrilonitrile, polypropylene, polyvinyl chloride, and combinations thereof.

3. The method of claim 1, wherein the precipitated mRNA is captured by a membrane having a surface area greater than 2,000 cm$^2$.

4. The method of claim 1, wherein the precipitating mRNA comprises treating mRNA with a denaturing agent, salt, surfactant or solvent suitable for precipitating the mRNA.

5. The method of claim 4, wherein the denaturing agent is selected from the group consisting of lithium chloride, potassium chloride, guanidinium chloride, guanidinium thiocyanate, guanidinium isothiocyanate, ammonium acetate and combinations thereof.

6. The method of claim 5, wherein the denaturing agent is guanidinium thiocyanate.

7. The method of claim 5, wherein the precipitating comprises treating with 4M guanidinium thiocyanate, and 0.5% sodium lauryl sarcosyl and/or 25 mM sodium citrate.

8. The method of claim 4, wherein the solvent suitable for precipitating the mRNA is absolute ethanol or isopropyl alcohol.

9. The method of claim 8, wherein the solvent is absolute ethanol.

10. The method of claim 1, wherein the method further comprises a step of washing the precipitated mRNA before eluting.

11. The method of claim 10, wherein the washing step comprises multiple rinse cycles using a wash solution comprising a guanidinium buffer and ethanol, followed by about 70-80% ethanol.

12. The method of claim 11, wherein the multiple rinse cycles are more than 5 cycles.

13. The method of claim 1, wherein the eluting step comprises re-solubilizing the captured precipitated mRNA with RNAse-free water.

14. The method of claim 1, wherein the purified mRNA solution is dialyzed with 1 mM sodium citrate using a 100 kDa molecular weight cut-off (MWCO) membrane.

15. The method of claim 1, wherein the mRNA is purified at a scale of or greater than 1 gram, 5 gram, 10 gram, 100 gram, 1 kg, 10 kg, or 100 kg per batch.

16. A method of manufacturing mRNA comprising purifying the in vitro synthesized mRNA according to the method of claim 1.

\* \* \* \* \*